(12) United States Patent
Kobayashi et al.

(10) Patent No.: US 10,584,116 B2
(45) Date of Patent: Mar. 10, 2020

(54) HETEROCYCLIC SULFONAMIDE DERIVATIVE AND MEDICINE CONTAINING SAME

(71) Applicant: EA Pharma Co., Ltd., Tokyo (JP)

(72) Inventors: Kaori Kobayashi, Kawasaki (JP);
Tamotsu Suzuki, Kawasaki (JP);
Tatsuya Okuzumi, Kawasaki (JP)

(73) Assignee: EA Pharma Co., Ltd., Tokyo (JP)

( * ) Notice: Subject to any disclaimer, the term of this patent is extended or adjusted under 35 U.S.C. 154(b) by 0 days.

(21) Appl. No.: 16/054,077

(22) Filed: Aug. 3, 2018

(65) Prior Publication Data
US 2019/0023699 A1 Jan. 24, 2019

Related U.S. Application Data

(63) Continuation of application No. PCT/JP2017/004134, filed on Feb. 3, 2017.

(30) Foreign Application Priority Data

Feb. 5, 2016 (JP) .................................. 2016-021358

(51) Int. Cl.
*C07D 405/14* (2006.01)
*A61P 25/00* (2006.01)

(52) U.S. Cl.
CPC ............ *C07D 405/14* (2013.01); *A61P 25/00* (2018.01)

(58) Field of Classification Search
None
See application file for complete search history.

(56) References Cited

U.S. PATENT DOCUMENTS

| | | |
|---|---|---|
| 8,614,201 B2 | 12/2013 | Berthelot et al. |
| 9,562,043 B2 | 2/2017 | Suzuki et al. |
| 2008/0081818 A1 | 4/2008 | Abe et al. |
| 2012/0083474 A1 | 4/2012 | Berthelot et al. |
| 2014/0329796 A1 | 11/2014 | Suzuki et al. |
| 2015/0197509 A1 | 7/2015 | Brotherton-Pleiss et al. |
| 2015/0284375 A1 | 10/2015 | Kobayashi et al. |
| 2016/0024009 A1 | 1/2016 | Fruttarolo et al. |
| 2016/0221945 A1 | 8/2016 | Chen et al. |
| 2016/0264567 A1 | 9/2016 | Yuen et al. |
| 2016/0332999 A1 | 11/2016 | Kobayashi et al. |
| 2018/0162844 A1 | 6/2018 | Kobayashi et al. |

FOREIGN PATENT DOCUMENTS

| | | |
|---|---|---|
| EP | 2 520 566 A1 | 11/2012 |
| JP | 2015-535836 A | 12/2015 |
| WO | WO 2007/119889 A1 | 10/2007 |
| WO | WO 2010/141805 A1 | 12/2010 |
| WO | WO 2013/108857 A1 | 7/2013 |
| WO | WO 2014/098098 A1 | 6/2014 |
| WO | WO 2014/135617 A1 | 9/2014 |
| WO | WO 2015/052264 A1 | 4/2015 |
| WO | WO 2015/115507 A1 | 8/2015 |
| WO | WO 2016/128529 A1 | 8/2016 |
| WO | WO 2017/018495 A1 | 2/2017 |

OTHER PUBLICATIONS

Bandell, M., et al., "Noxious Cold Ion Channel TRPA1 is Activated by Pungent Compounds and Bradykinin", Neuron, vol. 41, Mar. 25, 2004, pp. 849-857.
MacPherson, L.J., et al., "Noxious Compounds Activate TRPA1 Ion Channels through Covalent Modification of Cysteines", Nature, Feb. 2007, vol. 445, pp. 541-545.
Trevisani, M., et al., "4-Hydroxynonenal, an Endogenous Aldehyde, Causes Pain and Neurogenic Inflammation through Activation of the Irritant Receptor TRPA1", Proc. Natl. Academy Science U S A., 2007, vol. 104 No. 33, pp. 13519-13524.
Zurborg, S., et al., "Direct Activation of the Ion Channel TRPA1 by $Ca^{2+}$", Nature Neuroscience, 2007, vol. 10 No. 3, pp. 277-279.
Nagata, K., et al., "Nociceptor and Hair Cell Transducer Properties of TRPA1, a Channel for Pain and Hearing", The Journal of Neuroscience, Apr. 20, 2005, vol. 25 No. 16, pp. 4052-4061.
Story, G.M., et al., "ANKTM1, a TRP-like Channel Expressed in Nociceptive Neurons, Is Activated by Cold Temperatures", Cell, Mar. 21, 2003, vol. 112 No. 6, pp. 819-829.
Bautista, D.M., et al., "Pungent Products from Garlic Activate the Sensory Ion Channel TRPA1", Proc Natl Academy Sciences U S A., Aug. 23, 2005, vol. 102 No. 3, pp. 12248-12252.
Obata, K., et al., "TRPA1 induced in Sensory Neurons Contributes to Cold Hyperalgesia after Inflammation and Nerve Injury", Journal of Clinical Investigation, Sep. 2005, vol. 115 No. 9, pp. 2393-2401.
McNamara, C.R., et al., "TRPA1 Mediates Formalin-Induced Pain", Proc Natl Academy Science U S A., Aug. 14, 2007, vol. 104 No. 33, pp. 13525-13530.
Kondo, T., et al., "Role of Transient Receptor Potential A1 in Gastric Nociception", Digestion, 2010, vol. 82 No. 3, pp. 150-155.
Cattaruzza, F., et al., "Transient Receptor Potential Ankyrin-1 has a Major Role in Mediating Visceral Pain in Mice", American Journal Physiol Gastrointest Liver Physiol., 2010, vol. 298 No. 1, pp. G81-G91.

(Continued)

*Primary Examiner* — Kamal A Saeed
(74) *Attorney, Agent, or Firm* — Oblon, McClelland, Maier & Neustadt, L.L.P.

(57) ABSTRACT

Compounds of represented by formula (I):

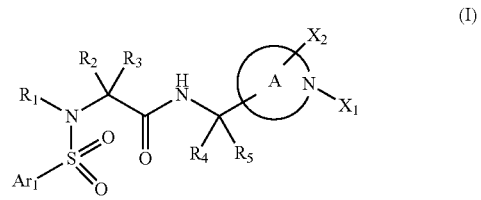

wherein each symbol is defined herein and pharmaceutically acceptable salts thereof exhibit TRPA1 antagonist activity and are useful as TRPA1 antagonists and the prophylaxis or treatment of diseases involving TRPA1.

19 Claims, 1 Drawing Sheet
Specification includes a Sequence Listing.

(56) References Cited

OTHER PUBLICATIONS

Cattaruzza, F., et al., "Transient Receptor Potential Ankyrin-1 Mediates Chronic Pancreatitis Pain in Mice", American Journal Physiol Gastrointest Live Physiol., Jun. 1, 2013; vol. 304 No. 11, pp. G1002-G1012.
Caceres, A.I., et al., "A Sensory Neuronal Ion Channel Essential for Airway Inflammation and Hyperreactivity in Asthma", Proc Natl Academy Sciences U S A., 2009, vol. 106 No. 22, pp. 9099-9104.
Xiao, B., et al., "Scratching the Surface: a Role of Pain-Sensing TRPA1 in Itch", Nature Neuroscience, May 2011, vol. 14 No. 5, pp. 540-542.
Wilson, S.R., et al., "TRPA1 is Required for Histamine-Independent, Mas-Related G Protein-Coupled Receptor-Mediated Itch", Nature Neuroscience, May 2011, vol. 14 No. 5, pp. 595-602 with cover page.
McGaraughty, S., et al., "TRPA1 Modulation of Spontaneous and Mechanically Evoked Firing of Spinal Neurons in Uninjured, Osteoarthritic, and Inflamed Rats", Molecular Pain, Mar. 5, 2010, vol. 6 No. 14, pp. 1-11.
Andersson, K.-E., et al., "The Role of the Transient Receptor Potential (TRP) Superfamily of Cation-Selective Channels in the Management of the Overactive Bladder", BJU International, Oct. 2010, vol. 106 No. 8, pp. 1114-1127.
Nassini, R., et al., "Oxaliplatin Elicits Mechanical and Cold Allodynia in Rodents via TRPA1 Receptor Stimulation", Pain, Jul. 2011, vol. 152 No. 7, pp. 1621-1631.
Materazzi, S., et al., "TRPA1 and TRPV4 mediate paclitaxel-induced peripheral neuropathy in mice via a glutathione-sensitive mechanism", Pflugers Arch.—Eur. J. Physiol, Apr. 2012, vol. 463 No. 4, pp. 561-569.
Trevisan, G., et al., "Novel Therapeutic Strategy to Prevent Chemotherapy-Induced Persistent Sensory Neuropathy by TRPA1 Blockade", Cancer Research, May 15, 2013, vol. 73 No. 10, pp. 3120-3131.
Supplementary European Search Report dated Sep. 16, 2019 issued in corresponding European patent application No. 17747613.2.
Database Chemcats [Online] Chemical Abstract Service Mar. 6, 2015, XP002793606, Database accession No. 1602351403, "Aurora Screening Compounds 2", Feb. 21, 2019.
Database Chemcats [Online] Chemical Abstract Service, Sep. 18, 2008, XP002793607, Database accession No. 1892780912, "Princeton BioMolecular Research Screening Collection", Feb. 1, 2019.
Database Chemcats [Online] Chemical Abstract Service, Sep. 18, 2008, XP002793608, Database accession No. 1306097321 "LabNetwork Compounds", May 30, 2019.
Database Chemcats [Online] Chemical Abstract Service, Sep. 18, 2008, XP002793609, Database accession No. 2092014025, "Ambinter Stock Collection", Oct. 8, 2018.
Database Chemcats [Online] Chemical Abstract Service, Aug. 25, 2006, XP002793610, Database accession No. 1432495342 "LabNetwork Compounds", May 30, 2019.
Database Chemcats [Online] Chemical Abstract Service, Aug. 23, 2006, XP002793611, Database accession No. 1858734877, "Aurora Building Blocks 6", Feb. 21, 2019.
Database Chemcats [Online] Chemical Abstract Service, Aug. 23, 2006, XP002793612, Database accession No. 2099907607 "LabNetwork Compounds", May 30, 2019.
Database Chemcats [Online] Chemical Abstract Service, Aug. 23, 2006, XP002793631, Database accession No. 1664223638, "Aurora Building Blocks 6" Feb. 21, 2019.
Database Chemcats [Online] Chemical Abstract Service, Aug. 23, 2006, XP002793614, Database accession No. 1823080362 "Aurora Screening Compounds I", Feb. 21, 2019.
Database Chemcats [Online] Chemical Abstract Service, Aug. 23, 2006, XP002793613, Database accession No. 1880229540 "Aurora Building Blocks 6 Aurora Building Blocks 6", Feb. 21, 2019.
Database Chemcats [Online] Chemical Abstract Service, Aug. 23, 2006, XP002793615, Database accession No. 1797399617 "LabNetwork Compounds", May 30, 2019.
Database Chemcats [Online] Chemical Abstract Service, Aug. 22, 2006, XP002793616, Database accession No. 0946471119 "Aurora Screening Compounds I", Feb. 21, 2019.
Database Chemcats [Online] Chemical Abstract Service, Aug. 22, 2006, XP002793618, "Aurora Building Blocks 6", Feb. 21, 2019.
Database Chemcats [Online] Chemical Abstract Service, Aug. 22, 2006, XP002793619, Database accession No. 1866041867 "Princeton BioMolecular Research Screening Collection", Feb. 1, 2019.
Database Chemcats [Online] Chemical Abstract Service, Aug. 22, 2006, XP002793617, Database accession No. 2002875739 "LabNetwork Compounds", Aug. 22, 2019.
Database Chemcats [Online] Chemical Abstract Service, Aug. 22, 2006, XP002793621, Database accession No. 1677821799 "Princeton BioMolecular Research Screening Collection", Feb. 1, 2019.
Database Chemcats [Online] Chemical Abstract Service, Aug. 22, 2006, XP002793622, Database accession No. 2014967691 "Aurora Screening Compounds I", Feb. 21, 2019.

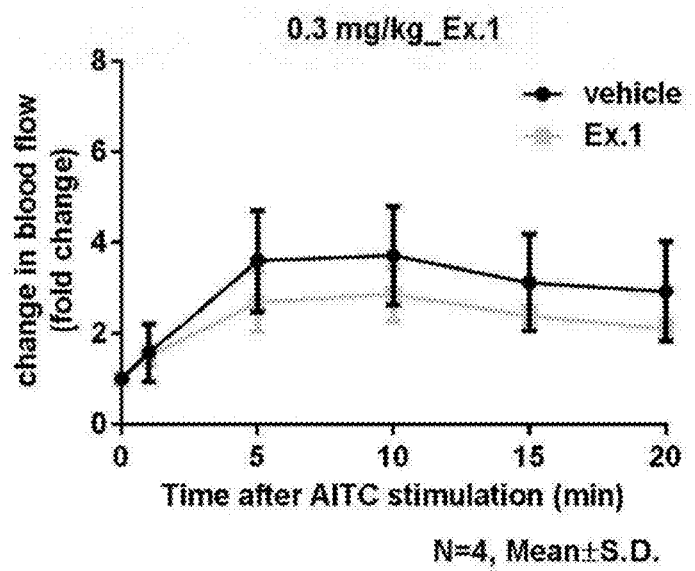
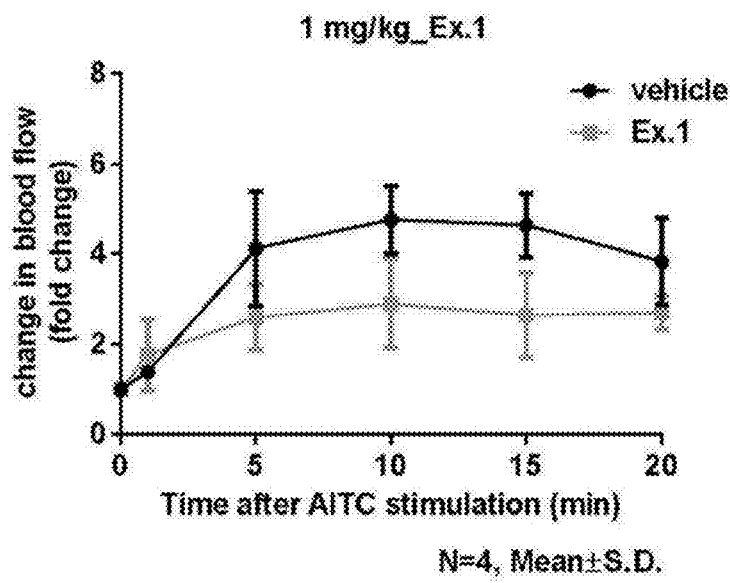
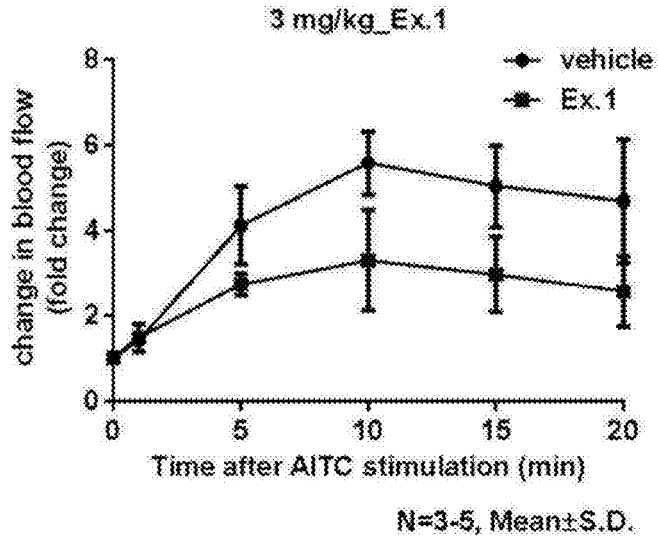

HETEROCYCLIC SULFONAMIDE DERIVATIVE AND MEDICINE CONTAINING SAME

CROSS REFERENCES TO RELATED APPLICATIONS

This application is a continuation of International Patent Application No. PCT/JP2017/004134, filed on Feb. 3, 2017, and claims priority to Japanese Patent Application No. 2016-021358, filed on Feb. 5, 2016, both of which are incorporated herein by reference in their entireties.

BACKGROUND OF THE INVENTION

Field of the Invention

The present invention relates to novel heterocyclic sulfonamide compounds having a transient receptor potential ankyrin 1 (TRPA1) antagonist activity and pharmaceutical compositions containing such a compound, as well as medicaments useful for the prophylaxis or treatment of diseases involving TRPA1.

Discussion of the Background

Transient receptor potential ankyrin 1 (TRPA1) is a non-selective cation channel belonging to the transient receptor potential (TRP) channel superfamily. Like other TRP channel family, it has six transmembrane domains and forms a tetramer consisting of four subunits. TRPA1 is a ligand dependent ion channel, which changes structure by the binding of ligand. As a result, the channel opens to allow intracellular flow of cations such as calcium ion, sodium ion and the like, thereby controlling the membrane potential of the cells. As the TRPA1 ligand, stimulant natural substances (e.g., allylisothiocyanate (AITC), cinnamaldehyde and the like), environmental stimulants (e.g., formalin, acrolein and the like), endogenous substances (e.g., 4-hydroxynonenal and the like) and the like are known (see Bandell M, et al., Neuron. 2004 Mar. 25; 41(6):849-57; Macpherson L J, et al., Nature. 2007 445(7127):541-5; and Trevisani M, et al., Proc Natl Acad Sci USA. 2007 104(33):13519-24, all of which are incorporated herein by reference in their entireties). It is known that the TRPA1 is also activated by cold stimulation, intracellular $Ca^{2+}$ and the like (see Bandell H, et al., Neuron. 2004 Mar. 25; 41(6):849-57, which is incorporated herein by reference in its entirety). Many ligands such as AITC, cinnamaldehyde and the like form a covalent bond with the cysteine residue and the lysine residue at the N-terminal in the cytoplasm, and activate the channel (see Macpherson L J, et al., Nature. 2007 445(7127):541-5, which is incorporated herein by reference in its entirety). In addition, intracellular $Ca^{2+}$ is considered to bind to the N-terminal EF band domain and opens the channel (see Zurborg S, et al., Nat Neurosci. 2007 10(3):277-9, which is incorporated herein by reference in its entirety). TRPA1 has been reported to be highly expressed in the sensory nerves such as spinal cord nerve, vagus nerve, trigeminal nerve and the like. TRPA1 has been reported to be co-expressed with perception•pain-related markers such as TRPV1, calcitonin gene related peptide (CGRP), substance P and the like (see Nagata K, et al., J Neurosci. 2005 25(16):4052-61; Story G M, et al., Cell. 2003 112(6):819-29 and Bautista D M, et al., Proc Natl Acad Sci USA. 2005 102(34):12248-52, all of which are incorporated herein by reference in their entireties).

Therefore, it is considered that, once TRPA1 present in the sensory nerve is activated by various stimulations, channel opening and depolarization of the cellular membrane occur, neuropeptides (CGRP, substance P) are liberated from the nerve ending, and perception such as nociception and the like is transmitted.

In fact, it has been reported that TRPA1 gene knockdown by the gene specific antisense method improves hyperalgesia induced by inflammation and nerve damage in pain model (see Obata K, et al., J Clin Invest. 2005 115(9):2393-401, which is incorporated herein by reference in its entirety). Also, it has been reported that a pain behavior induced by formalin disappears in TRPA1 gene knockout mouse (see McNamara C R, et al., Proc Natl Acad Sci USA. 2007 104(33):13525-30, which is incorporated herein by reference in its entirety). From the above, TRPA1 is considered to play an important role in the nociceptive transmission, and is expected as a treatment target in pain-associated diseases such as nociceptive pain, neuropathic pain and the like.

TRPA1 is known to show high expression in the afferent sensory nerve projected on the gastrointestinal tract such as esophagus, stomach, large intestine and the like. It has been reported that TRPA1 knockdown decreases nociceptive reaction due to extension of stomach (see Kondo T, et al., Digestion. 2010; 82(3):150-5, which is incorporated herein by reference in its entirety), and large intestine hyperalgesia induced by AITC and 2,4,6-trinitrobenzenesulfonic acid (TNBS) is normalized in TRPA1 gene knockout mouse (see Cattaruzza F, et al., Am J Physiol Gastrointest Liver Physiol. 2010 298(1):G81-91, which is incorporated herein by reference in its entirety). From the above, TRPA1 is suggested to play an important role in the perception•nociception transmission in the gastrointestinal tract, and is expected to be effective for the treatment of digestive tract diseases such as functional dyspepsia, irritable bowel syndrome, erosive esophagitis, inflammatory bowel disease (Crohn's disease, ulcerative colitis), pancreatitis and the like (see Cattaruzza F, et al., Am J Physiol Gastrointest Liver Physiol. 2013 Jun. 1; 304(11):G1002-12, which is incorporated herein by reference in its entirety).

Furthermore, TRPA1 plays a key role in the detection of a noxious substance in the trachea. It has been reported that TRPA1 gene knockout suppresses inflammation of the trachea in OVA model (see Caceres A I, et al., Proc Natl Acad Sci USA. 2009 106(22):9099-104, which is incorporated herein by reference in its entirety). Therefore, antagonism of TRPA1 is considered to be also useful for pulmonary diseases such as asthma, chronic coughing, COPD and the like.

As other diseases involving TRPA1, dermatic diseases such as pruritus, atopic dermatitis, burn and the like (see Xiao B, and Patapoutian A., Nat Neurosci. 2011 May; 14(5):540-2; and Wilson S R, et al., Nat Neurosci. 2011 May: 14(5):595-602, both of which are incorporated herein by reference in their entireties), inflammatory diseases such as burn, osteoarthritis and the like (see McGaraughty S, et al., Mol Pain. 2010 Mar. 5; 6:14, which is incorporated herein by reference in its entirety), bladder diseases such as overactive bladder•abnormal urination•cystitis and the like (see Andersson K E, et al., BJU Int. 2010 October; 106(8): 1114-27, which is incorporated herein by reference in its entirety), neurological diseases such as anticancer agent-induced neuropathy and the like (see Nassini R, et al., Pain. 2011 July; 152(7):1621-31; Materazzi S, et al., Pflugers Arch. 2012 April; 463(4):561-9; and Trevisan G, et al., Cancer Res. 2013 May 15; 73(10):3120-31, all of which are incorporated herein by reference in their entireties) and the like are known. Thus, a compound capable of functional regulation of TRPA1 is industrially and therapeutically useful in many aspects. In particular, a compound that antagonizes TRPA1 is highly expected as a new therapeutic drug for pain diseases, digestive tract diseases, lung diseases, dermatic diseases, inflammatory diseases, bladder diseases and neurological diseases in human.

WO 2010/141805, WO 2015/115507, WO 2014/098098, WO 2013/108857, all of which are incorporated herein by reference in their entireties, report TRPA1 antagonists each having the following structure.

WO 2010/141805:

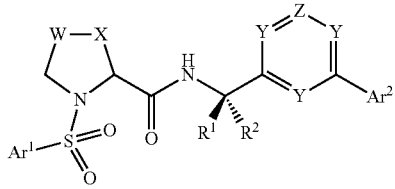

wherein each symbol is as defined in WO 2010/141805.

WO 2015/115507:

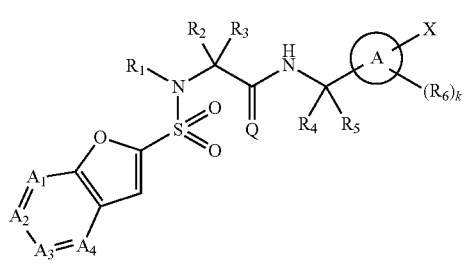

wherein each symbol is as defined in WO 2015/115507

WO 2014/098098:

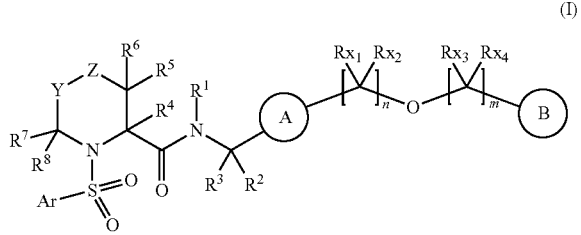

wherein each symbol is as defined in WO 2014/098098.

WO 2013/108857:

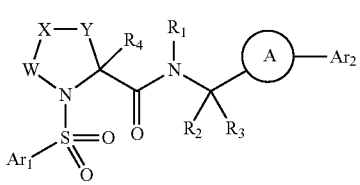

wherein each symbol is as defined in WO 2013/108857.

However, these compounds are structurally different from the compound represented by the formula (I) of the present invention to be described below.

SUMMARY OF THE INVENTION

Accordingly, it is one object of the present invention to provide novel compounds having a transient receptor potential ankyrin 1 (TRPA1) antagonist activity.

It is another object of the present invention to provide novel TRPA1 antagonists.

It is another object of the present invention to provide novel medicaments containing such a compound.

It is another object of the present invention to provide novel methods for the prophylaxis and/or treatment of a disease involving TRPA1.

These and other objects, which will become apparent during the following detailed description, have been achieved by the inventors' discovery that certain particular heterocyclic sulfonamide compounds have a strong TRPA1 antagonist activity, and are useful for the prophylaxis and/or treatment of diseases involving TRPA1 (e.g., pain associated diseases, digestive tract diseases, lung diseases, bladder diseases, inflammatory diseases, dermatic diseases, and neurological diseases.

Thus, the present invention provides the following:

(1) A compound represented by formula (I):

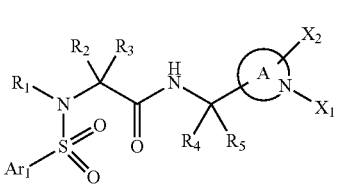

wherein
ring A is a 6-membered, nitrogen-containing heterocycle substituted by 1 or 2 oxo groups;
$Ar_1$ is a $C_{6-10}$ aryl group optionally having substituent(s), a $C_{1-9}$ heteroaryl group optionally having substituent(s), or a $C_{3-7}$ cycloalkyl group optionally having substituent(s);
$R_1$ is hydrogen or a $C_{1-6}$ alkyl group optionally having substituent(s);
$R_2$ is hydrogen, a $C_{1-6}$ alkyl group optionally having substituent(s) or a $C_{2-6}$ alkenyl group optionally having substituent(s);
$R_3$ is hydrogen or a alkyl group;
$R_4$ is hydrogen or a $C_{1-6}$ alkyl group;
$R_5$ is hydrogen or a $C_{1-6}$ alkyl group;
$R_1$ and $R_2$ are optionally joined to form a nitrogen-containing ring optionally having substituent(s);
$R_2$ and $R_3$ are optionally joined to form cycloalkene or cycloalkane;
$R_4$ and $R_5$ are optionally joined to form cycloalkane;
one of $X_1$ and $X_2$ is one kind selected from the following Group A, and the other is an alkyl group optionally having substituent(s) (substituents are optionally joined to form a ring) or a hydrogen atom (provided that when ring A is a ring having a pyridone skeleton, $X_1$ is not a hydrogen atom; and $X_1$ and $X_2$ are not hydrogen atoms at the same time);
wherein Group A is
hydrogen,
-Cy,
—$C(R_{x1}R_{x2})$-Cy, —C(R$_{x1}$R$_{x2}$)—C(R$_{x3}$R$_{x4}$)-Cy,
—C(R$_{x1}$)=C(R$_{x2}$)-Cy,
—O-Cy,
—O—C(R$_{x1}$R$_{x2}$)-Cy,
—C(R$_{x1}$R$_{x2}$)—O-Cy,
—S(O)n-Cy,
—S(O)n-C(R$_{x1}$R$_{x2}$)-Cy,
—C(R$_{x1}$R$_{x2}$)—S(O)n-Cy,
—N(R$_{x5}$)-Cy,
—N(R$_{x5}$)—C(R$_{x3}$R$_{x2}$)-Cy,
—C(R$_{x1}$R$_{x2}$)—N(R$_{x5}$)-Cy,
—C(O)—N(R$_{x5}$)-Cy,
—N(R$_{x5}$)—C(O)-Cy,
—S(O)m-N(R$_{x5}$)-Cy,
—N(R$_{x5}$)—S(O)m-Cy, or
—O—S(O)m-Cy wherein n is an integer of 0 to 2; m is 1 or 2; Cy is a saturated or unsaturated cyclic group optionally having substituent(s) (optionally containing heteroatom(s)); R$_{x1}$, R$_{x2}$, R$_{x3}$, R$_{x4}$, and R$_{x5}$ are the same or different and each is a hydrogen, a C$_{1-6}$ alkyl group optionally having substituent(s) or a C$_{1-6}$ alkoxycarbonyl group optionally having substituent(s), or a pharmaceutically acceptable salt thereof.

(2) The compound of the above-mentioned (1), wherein the 6-membered, nitrogen-containing heterocycle substituted by 1 or 2 oxo groups is selected from the group consisting of oxopyridine, dioxopyridine, oxopyrimidine and dioxopyrimidine, or a pharmaceutically acceptable salt thereof.

(2-1) The compound of the above-mentioned (1), wherein the 6-membered, nitrogen-containing heterocycle substituted by 1 or 2 oxo groups is oxopyridine or dioxopyrimidine, or a pharmaceutically acceptable salt thereof.

(3) The compound of the above-mentioned (1), (2) or (2-1), wherein, in the formula (I), R$_1$ is a hydrogen or a C$_{1-6}$ alkyl group optionally having substituent(s);

R$_2$ is a hydrogen or a C$_{1-6}$ alkyl group optionally having substituent(s);

R$_3$ is a hydrogen;

R$_4$ is a hydrogen or a C$_{1-6}$ alkyl group;

R$_5$ is a hydrogen or a C$_{1-6}$ alkyl group;

R$_1$ and R$_2$ are optionally joined to form a nitrogen containing ring optionally having substituent(s);

X$_1$ is
-Cy,
—C(R$_{x1}$R$_{x2}$)-Cy,
—C(R$_{x1}$R$_{x2}$)—C(R$_{x3}$R$_{x4}$)-Cy,
—C(R$_{x1}$)=C(R$_{x2}$)-Cy,
—O-Cy,
—O—C(R$_{x1}$R$_{x2}$)-Cy,
—C(R$_{x1}$R$_{x2}$)—O-Cy,
—S(O)n-Cy,
—S(O)n-C(R$_{x1}$R$_{x2}$)-Cy,
—C(R$_{x1}$R$_{x2}$)—S(O)n-Cy,
—N(R$_{x5}$)-Cy,
—N(R$_{x5}$)—C(R$_{x1}$R$_{x2}$)-Cy,
—C(R$_{x1}$R$_{x2}$)—N(R$_{x5}$)-Cy,
—C(O)—N(R$_{x5}$)-Cy,
—N(R$_{x5}$)—C(O)-Cy,
—S(O)m-N(R$_{x5}$)-Cy,
—N(R$_{x5}$)—S(O)m-Cy or
—O—S(O)m-Cy; and X$_2$ is an alkyl group optionally having substituent(s) (substituents are optionally joined to form a ring), or a pharmaceutically acceptable salt thereof.

(4) The compound of any of the above-mentioned (1)-(3) and (2-1), wherein R$_1$ and R$_2$ are joined to form a nitrogen-containing ring optionally having substituent(s), or a pharmaceutically acceptable salt thereof.

(5) The compound of any of the above-mentioned (1)-(3) and (2-1), wherein R$_1$ is hydrogen and R$_2$ is a C$_{1-6}$ alkyl group, or a pharmaceutically acceptable salt thereof.

(6) The compound of any of the above-mentioned (1)-(3) and (2-1), wherein a partial structure (a):

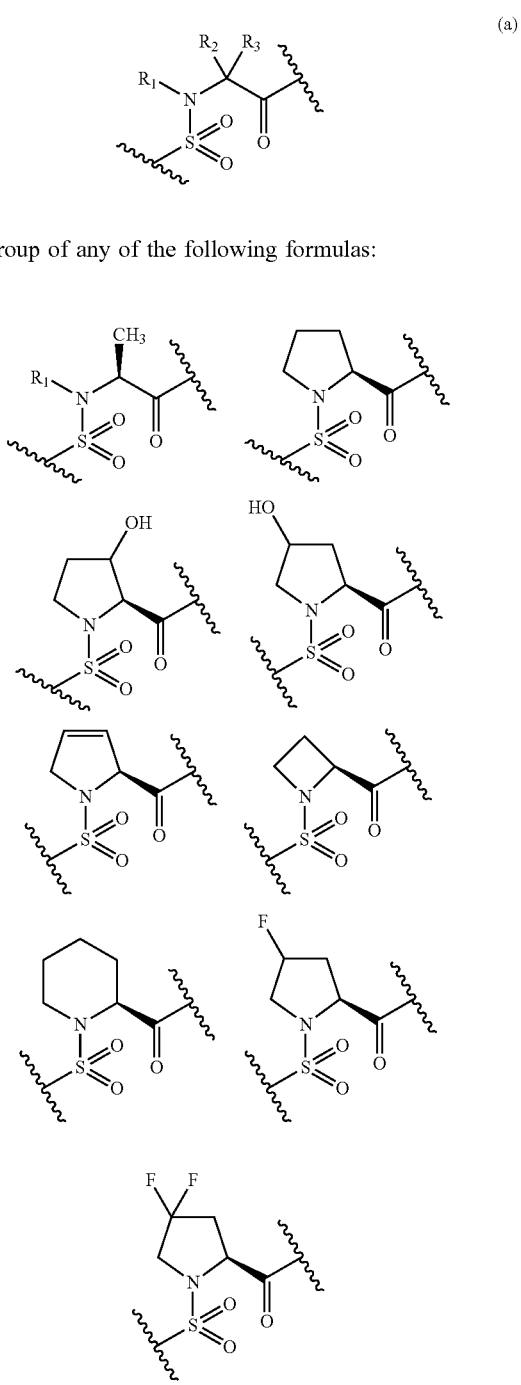

is a group of any of the following formulas:

or a pharmaceutically acceptable salt thereof.

(6-1) The compound of any of the above-mentioned (1)-(3) and (2-1), wherein a partial structure (a):

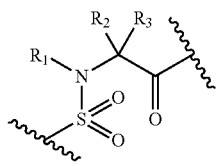
(a)

is a group of any of the following formulas:

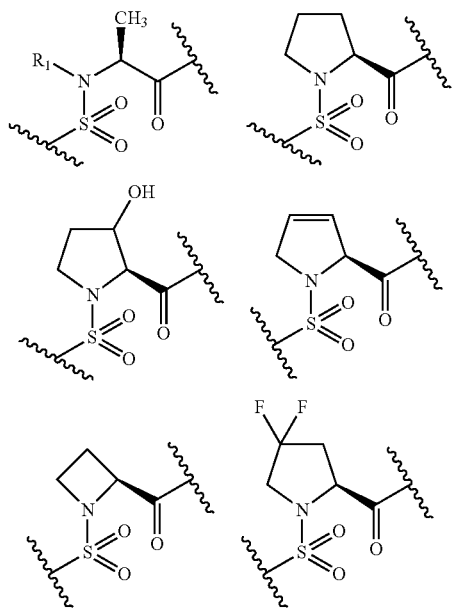

or a pharmaceutically acceptable salt thereof.

(7) The compound of any of the above-mentioned (1)-(3) and (2-1), wherein a partial structure (a):

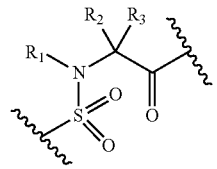
(a)

is a group of any of the following formulas:

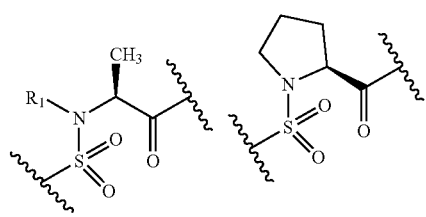

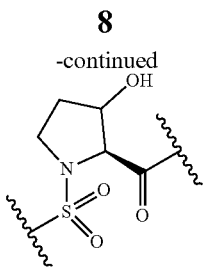

or a pharmaceutically acceptable salt thereof.

(8) The compound of any of the above-mentioned (1)-(7), (2-1) and (6-1), wherein a partial structure (b) containing ring A:

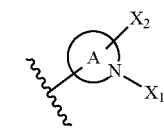
(b)

is a group of any of the following formulas:

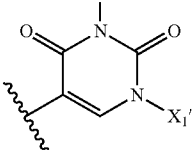
(i)

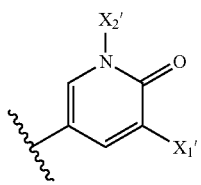
(ii)

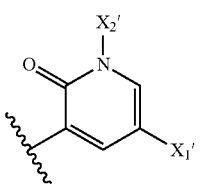
(iii)

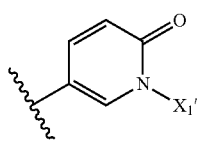
(v)

wherein
$X_1'$ is one kind selected from the following Group B;
wherein Group B is
-Cy,
—$C(R_{x1}R_{x2})$-Cy,
—$C(R_{x1}R_{x2})$—$C(R_{x3}R_{x4})$-Cy,
—$C(R_{x1})$=$C(R_{x2})$-Cy,
—O-Cy,
—O—$C(R_{x1}R_{x2})$-Cy,
—$C(R_{x1}R_{x2})$—O-Cy,
—$S(O)n$-Cy, —S(O)n-C(R$_{x1}$R$_{x2}$)-Cy,
—C(R$_{x1}$R$_{x2}$)—S(O)n-Cy,
—N(R$_{x5}$)-Cy,
—N(R$_{x5}$)—C(R$_{x1}$R$_{x2}$)-Cy,
—C(R$_{x1}$R$_{x2}$)—N(R$_{x5}$)-Cy,
—C(O)—N(R$_{x5}$)-Cy,
—N(R$_{x5}$)—C(O)-Cy,
—S(O)m-N(R$_{x5}$)-Cy,
—N(R$_{x5}$)—S(O)m-Cy, or
—O—S(O)m-Cy wherein n is an integer of 0 to 2; m is 1 or 2; Cy is a saturated or unsaturated cyclic group optionally having substituent(s) (optionally containing heteroatom(s)); R$_{x1}$, R$_{x2}$, R$_{x3}$, R$_{x4}$ and R$_{x5}$ are the same or different and each is a hydrogen, a C$_{1-6}$ alkyl group optionally having substituent(s) or a C$_{1-6}$ alkoxycarbonyl group optionally having substituent(s); and X$_2$' is an alkyl group optionally having substituent(s) (substituents are optionally joined to form a ring), or a pharmaceutically acceptable salt thereof.

(8-1) The compound of any of the above-mentioned (1)-(7), (2-1) and (6-1), wherein a partial structure (b) containing ring A is a group represented by:

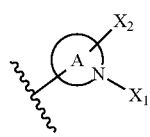

is the following formula (i):

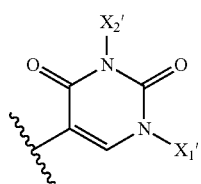

wherein
X$_1$' is one kind selected from the following Group B;
wherein Group B is
-Cy,
—C(R$_{x1}$R$_{x2}$)-Cy,
—C(R$_{x1}$R$_{x2}$)—C(R$_{x3}$R$_{x4}$)-Cy,
—C(R$_{x1}$)═C(R$_{x2}$)-Cy,
—O-Cy,
—O—C(R$_{x1}$R$_{x2}$)-Cy,
—C(R$_{x1}$R$_{x2}$)—O-Cy,
—S(O)n-Cy,
—S(O)n-C(R$_{x1}$R$_{x2}$)-Cy,
—C(R$_{x1}$R$_{x2}$)—S(O)n-Cy,
—N(R$_{x5}$)-Cy,
—N(R$_{x5}$)—C(R$_{x1}$R$_{x2}$)-Cy,
—C(R$_{x1}$R$_{x2}$)—N(R$_{x5}$)-Cy,
—C(O)—N(R$_{x5}$)-Cy,
—N(R$_{x5}$)—C(O)-Cy,
—S(O)m-N(R$_{x5}$)-Cy,
—N(R$_{x5}$)—S(O)m-Cy, and
—O—S(O)m-Cy, wherein n is an integer of 0 to 2; m is 1 or 2; Cy is a saturated or unsaturated cyclic group optionally having substituent(s) (optionally containing heteroatom(s)); R$_{x1}$, R$_{x2}$, R$_{x3}$, R$_{x4}$ and R$_{x5}$ are the same or different and each is a hydrogen, a C$_{1-6}$ alkyl group optionally having substituent(s) or a C$_{1-6}$ alkoxycarbonyl group optionally having substituent(s); and X$_2$' is an alkyl group optionally having substituent(s) (substituents are optionally joined to form a ring), or a pharmaceutically acceptable salt thereof.

(9) The compound of any of the above-mentioned (1)-(8), (2-1), (6-1) and (8-1), wherein Ar$_1$ is a C$_{6-10}$ aryl group having one or more substituents selected from a halogeno group, a halogenoC$_{1-6}$ alkyl group, a halogenoC$_{1-6}$ alkoxy group and a C$_{1-6}$ alkyl group, or a C$_{1-9}$ heteroaryl group having one or more substituents selected from a halogeno group, a halogenoC$_{1-6}$ alkyl group, a halogenoC$_{1-6}$ alkoxy group and a C$_{1-6}$ alkyl group, or a pharmaceutically acceptable salt thereof.

(10) The compound of any of the above-mentioned (8), (8-1) or (9), wherein X$_1$' is -Cy, —O-Cy, —O—CH$_2$-Cy or —CH$_2$—CH$_2$-Cy, or a pharmaceutically acceptable salt thereof.

(11) The compound of the above-mentioned (10), wherein X$_1$' is -Cy, or a pharmaceutically acceptable salt thereof.

(12) The compound of the above-mentioned (10) or (11), wherein Cy is benzene optionally having substituent(s), pyridine optionally having substituent(s), pyrimidine optionally having substituent(s), pyridazine optionally having substituent(s) or pyrazine optionally having substituent(s), or a pharmaceutically acceptable salt thereof.

(12-1) The compound of the above-mentioned (10) or (11), wherein Cy is benzene optionally having substituent(s) or pyridine optionally having substituent(s), or a pharmaceutically acceptable salt thereof.

(13) The compound of the above-mentioned (10) or (11), wherein Cy is a group of any of the following formulas:

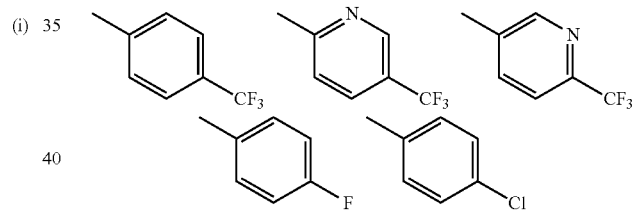

or a pharmaceutically acceptable salt thereof.

(13-1) The compound of the above-mentioned (10) or (11), wherein Cy is a group of any of the following formulas:

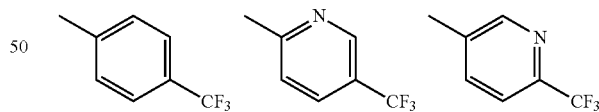

or a pharmaceutically acceptable salt thereof.

(14) The compound of any of the above-mentioned (1)-(13), (2-1) and (6-1), wherein R$_4$ and R$_5$ are hydrogen;
the partial structure (b) containing ring A:

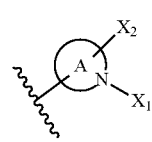

is a group of any of the following formulas:

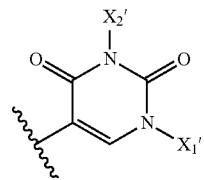
(i)

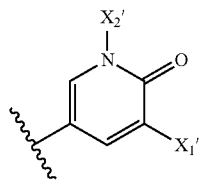
(ii)

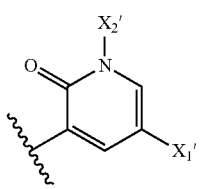
(iii)

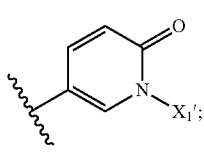
(v)

$X_1'$ is -Cy;
Cy is a group of any of the following formulas:

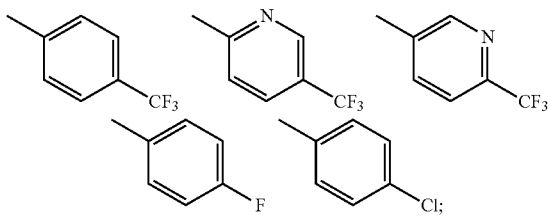

$Ar_1$ is a group of any of the following formulas:

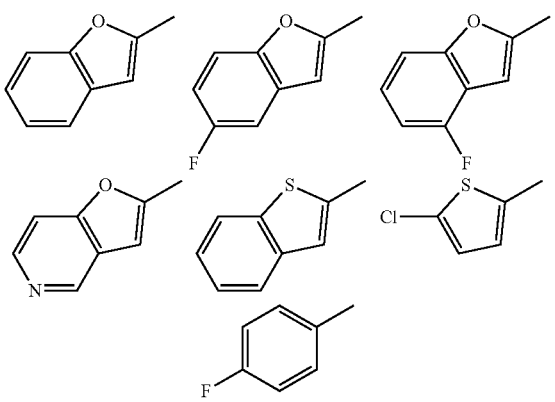

or a pharmaceutically acceptable salt thereof.

(14-1) The compound of any of the above-mentioned (1)-(13), (2-1) and (6-1), wherein $R_4$ and $R_5$ are hydrogens;
the partial structure (b) containing ring A:

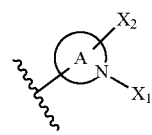
(b)

is a group of any of the following formulas:

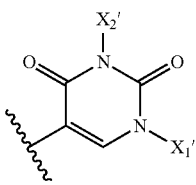
(i)

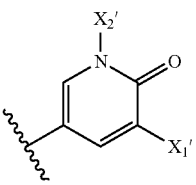
(ii)

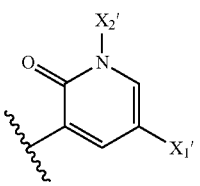
(iii)

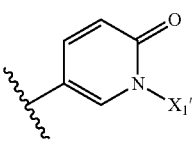
(v)

$X_1'$ is -Cy;
Cy is a group of any of the following formulas:

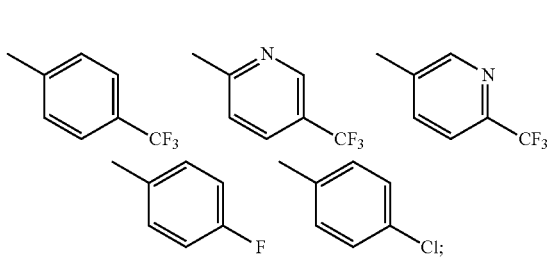

and

Ar₁ is a group of any of the following formulas:

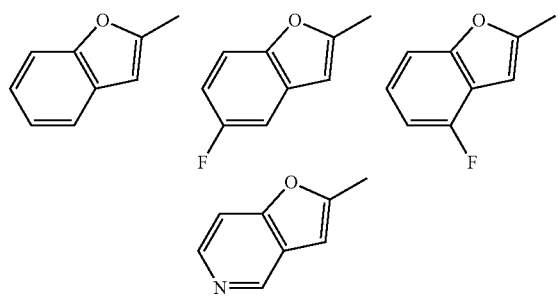

or a pharmaceutically acceptable salt thereof.

(14-2) The compound of any of the above-mentioned (1)-(13), (2-1), (6-1), and (8-1), wherein $R_4$ and $R_5$ are hydrogens;

the partial structure (b) containing ring A:

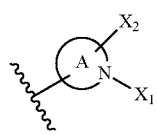

(b)

is a group represented by the following formula (i):

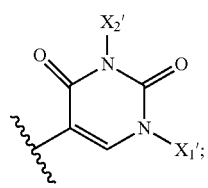

(i)

$X_1'$ is -Cy;
Cy is a group of any of the following formulas:

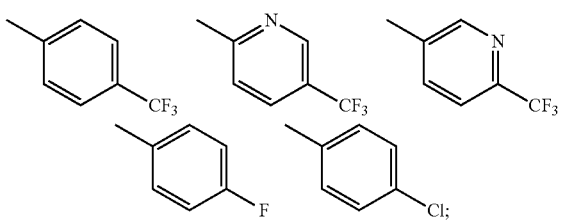

and
Ar₁ is a group of any of the following formulas:

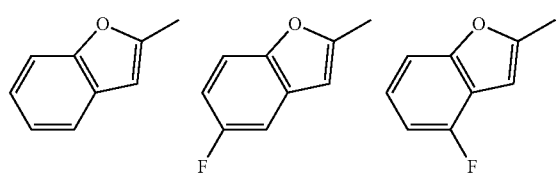

-continued

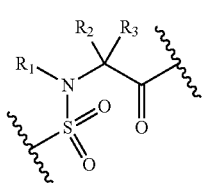

or a pharmaceutically acceptable salt thereof.

(14-3) The compound of the above-mentioned (1), wherein, in the formula (I),

Ar₁ is a group of any of the following formulas:

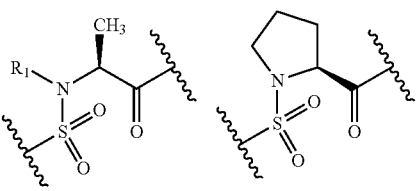

;

the partial structure (a):

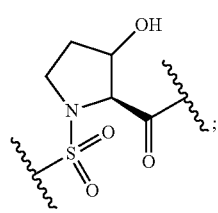

(a)

is a group of any of the following formulas:

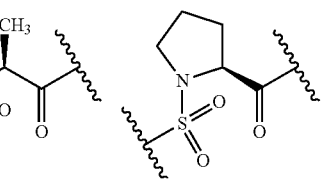

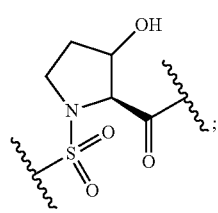

;

R$_4$ and R$_5$ are hydrogens;
the partial structure (b) containing ring A:

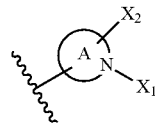
(b)

is a group of any of the following formulas:

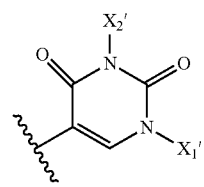
(i)

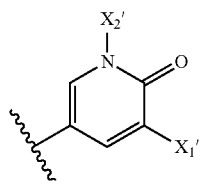
(ii)

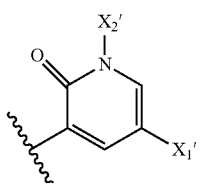
(iii)

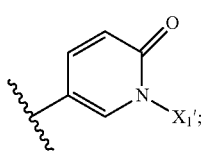
(v)

X$_1$' is -Cy; and
Cy is a group of any of the following formulas:

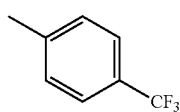 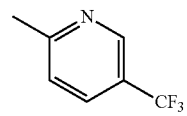 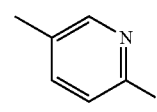

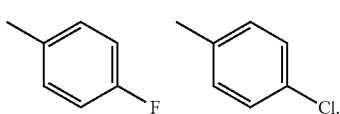

(14-4) The compound of the above-mentioned (1), wherein, in the formula (I),

Ar$_1$ is a group of any of the following formulas:

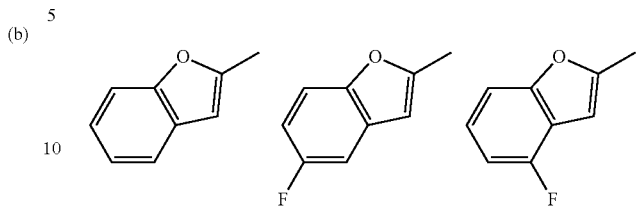

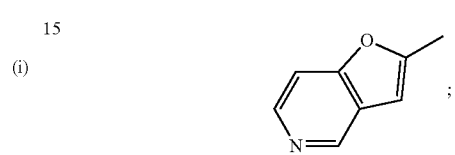

the partial structure (a):

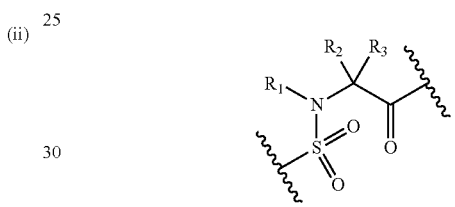
(a)

is a group of any of the following formulas:

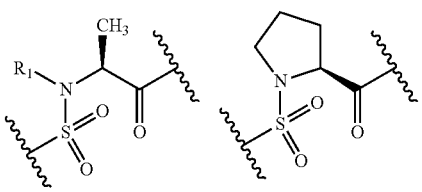

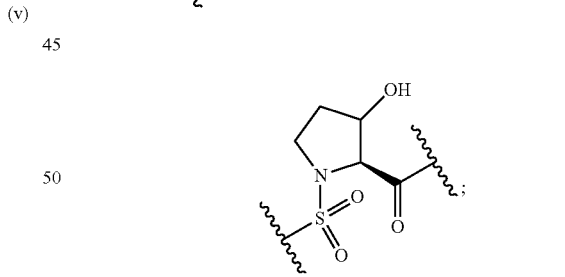

R$_4$ and R$_5$ are hydrogens;
the partial structure (b) containing ring A:

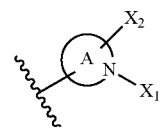
(b)

is a group represented by the following formula (i):

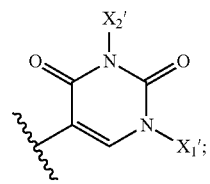

$X_1'$ is -Cy; and
Cy is a group of any of the following formulas:

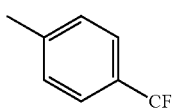 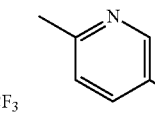 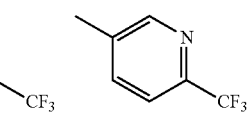

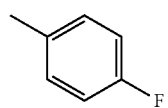 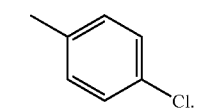

(15) The compound of the above-mentioned (1) which is represented by any of the following structural formula, or a pharmaceutically acceptable salt thereof:

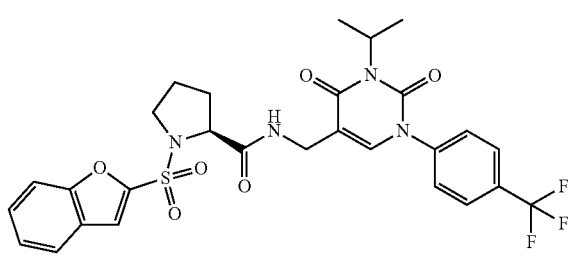

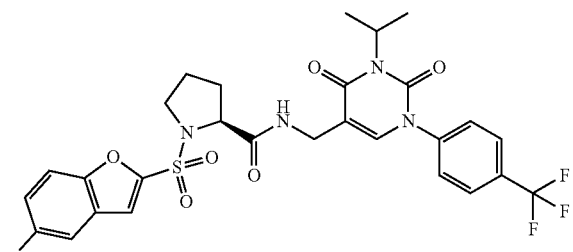

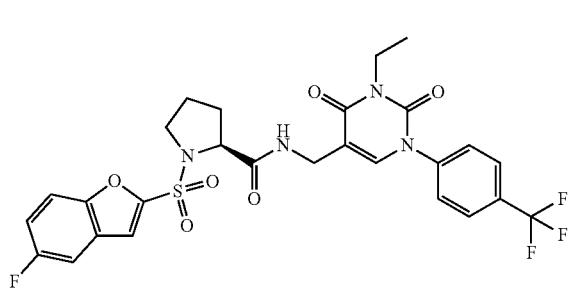

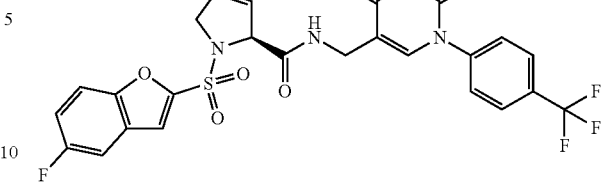

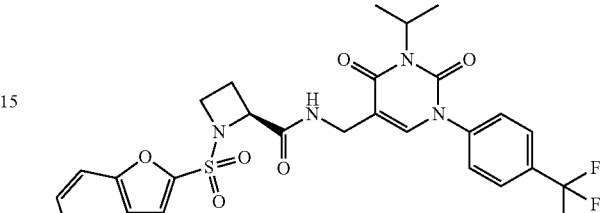

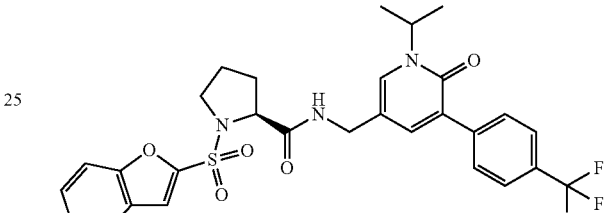

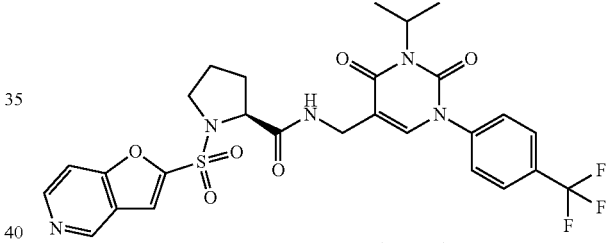

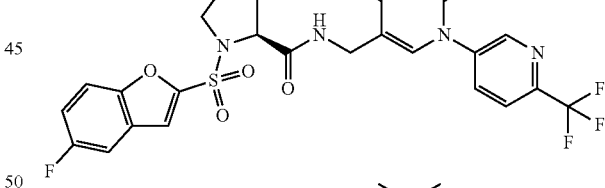

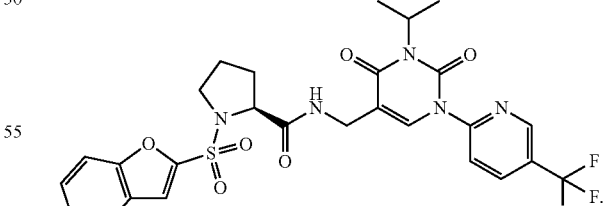

(16) The compound of any of the above-mentioned (1)-(15), (2-1), (6-1), (8-1), (12-1), (13-1) and (14-1)-(14-4), which is a TRPA1 antagonist, or a pharmaceutically acceptable salt thereof.

(17) A medicament comprising the compound of any of the above-mentioned (1)-(16), (2-1), (6-1), (8-1), (12-1), (13-1) and (14-1)-(14-4), or a pharmaceutically acceptable salt thereof as an active ingredient.

(18) The medicament of the above-mentioned (17), which is for the prophylaxis and/or treatment of a disease involving TRPA1.

(19) The medicament of the above-mentioned (18), wherein the disease involving TRPA1 is selected from the group consisting of chronic pain, acute pain, diabetic neuropathy, osteoarthritis, asthma, chronic cough, chronic obstructive pulmonary diseases, functional gastrointestinal disorder, erosive esophagitis, irritable bowel syndrome, inflammatory bowel disease, pancreatitis, anticancer agent-induced neuropathy, pruritus, and allergic dermatitis.

(20) The medicament of the above-mentioned (18), wherein the disease involving TRPA1 is selected from the group consisting of chronic pain, acute pain, asthma, chronic obstructive pulmonary diseases, functional gastrointestinal disorder, erosive esophagitis, inflammatory bowel disease, anticancer agent-induced neuropathy, and pruritus.

(21) A method for the prophylaxis and/or treatment of a disease involving TRPA1, comprising administering an effective amount of the compound of any of the above-mentioned (1)-(16), (2-1), (6-1), (8-1), (12-1), (13-1) and (14-1)-(14-4), or a pharmaceutically acceptable salt thereof to a subject in need thereof.

(22) The method of the above-mentioned (21), wherein the disease involving TRPA1 is selected from the group consisting of chronic pain, acute pain, diabetic neuropathy, osteoarthritis, asthma, chronic cough, chronic obstructive pulmonary diseases, functional gastrointestinal disorder, erosive esophagitis, irritable bowel syndrome, inflammatory bowel disease, pancreatitis, anticancer agent-induced neuropathy, pruritus, and allergic dermatitis.

(23) The method of the above-mentioned (21), wherein the disease involving TRPA1 is selected from the group consisting of chronic pain, acute pain, asthma, chronic obstructive pulmonary diseases, functional gastrointestinal disorder, erosive esophagitis, inflammatory bowel disease, anticancer agent-induced neuropathy, and pruritus.

(24) The compound of any of the above-mentioned (1)-(16), (2-1), (6-1), (8-1), (12-1), (13-1) and (14-1)-(14-4), or a pharmaceutically acceptable salt thereof for use for the prophylaxis and/or treatment of a disease involving TRPA1.

(25) The compound of the above-mentioned (24) or a pharmaceutically acceptable salt thereof, wherein the disease involving TRPA1 is selected from the group consisting of chronic pain, acute pain, diabetic neuropathy, osteoarthritis, asthma, chronic cough, chronic obstructive pulmonary diseases, functional gastrointestinal disorder, erosive esophagitis, irritable bowel syndrome, inflammatory bowel disease, pancreatitis, anticancer agent-induced neuropathy, pruritus, and allergic dermatitis.

(26) The compound of the above-mentioned (24) or a pharmaceutically acceptable salt thereof, wherein the disease involving TRPA1 is selected from the group consisting of chronic pain, acute pain, asthma, chronic obstructive pulmonary diseases, functional gastrointestinal disorder, erosive esophagitis, inflammatory bowel disease, anticancer agent-induced neuropathy, and pruritus.

Examples of other preferable embodiment of compound (I) include the compounds of the below-mentioned Examples and pharmaceutically acceptable salts thereof.

More preferred are the compounds of Examples 1-5 and 8 in the following Table (Table 1-1) and pharmaceutically acceptable salts thereof.

TABLE 1-1

| Ex. No. | Structure Formula |
|---|---|
| 1 | 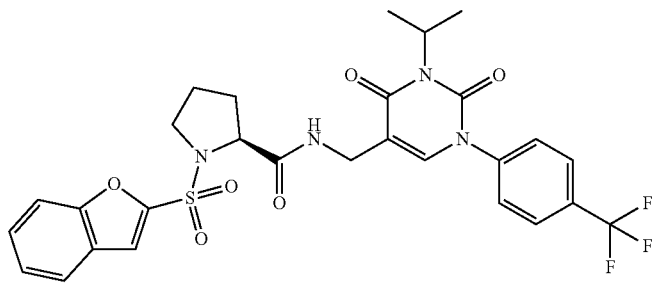 [SMILES: CC(C)n1c(=O)c(CNC(=O)[C@@H]2CCCN2S(=O)(=O)c2cc3ccccc3o2)cn(-c2ccc(C(F)(F)F)cc2)c1=O] |
| 2 | 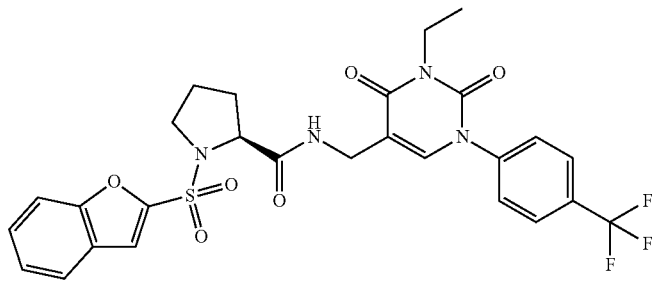 [SMILES: CCn1c(=O)c(CNC(=O)[C@@H]2CCCN2S(=O)(=O)c2cc3ccccc3o2)cn(-c2ccc(C(F)(F)F)cc2)c1=O] |

TABLE 1-1-continued
| Ex. No. | Structure Formula |
|---|---|
| 3 | 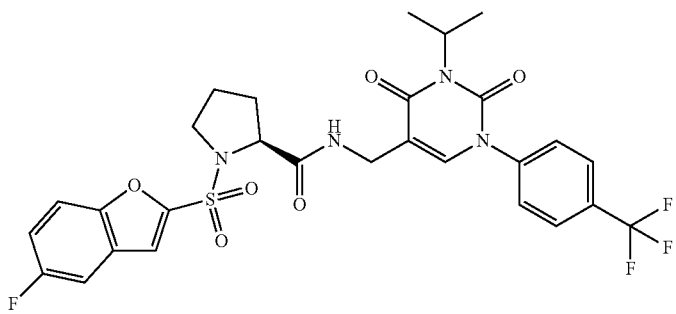 [SMILES: CC(C)n1c(=O)c(CNC(=O)[C@@H]2CCCN2S(=O)(=O)c2cc3cc(F)ccc3o2)cn(-c2ccc(C(F)(F)F)cc2)c1=O] |
| 4 | 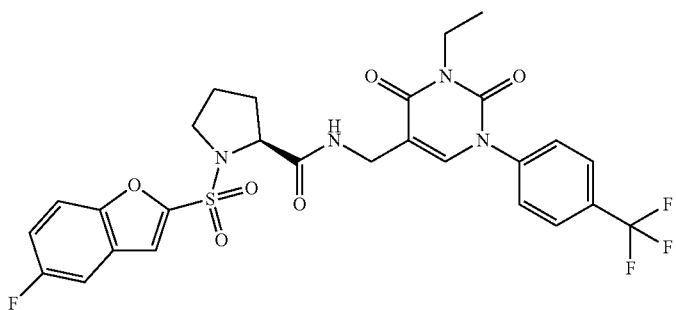 [SMILES: CCn1c(=O)c(CNC(=O)[C@@H]2CCCN2S(=O)(=O)c2cc3cc(F)ccc3o2)cn(-c2ccc(C(F)(F)F)cc2)c1=O] |
| 5 | 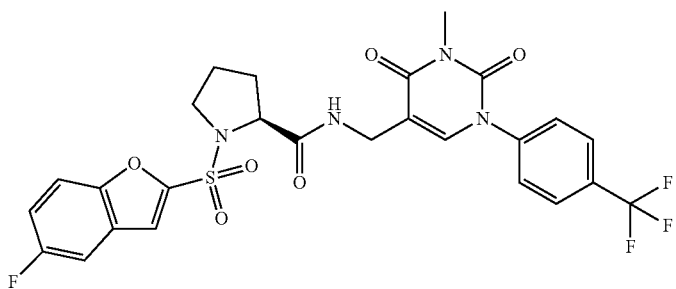 [SMILES: Cn1c(=O)c(CNC(=O)[C@@H]2CCCN2S(=O)(=O)c2cc3cc(F)ccc3o2)cn(-c2ccc(C(F)(F)F)cc2)c1=O] |
| 8 | 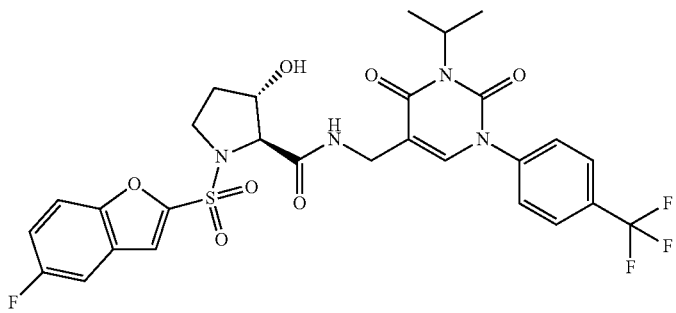 [SMILES: CC(C)n1c(=O)c(CNC(=O)[C@@H]2[C@@H](O)CCN2S(=O)(=O)c2cc3cc(F)ccc3o2)cn(-c2ccc(C(F)(F)F)cc2)c1=O] |

The compounds of Examples 10, 11, 13, 15 to 24, 27, 29, 30, 33, 34, 37, 40 to 43, 45, 46, 49 and 51 in the following Tables (Table 1-2, Table 1-3, Table 1-4, Table 1-5) and pharmaceutically acceptable salts thereof.

TABLE 1-2

| Ex. No. | Structure Formula |
|---|---|
| 10 | |
| 11 | |
| 13 | |
| 15 | |
| 16 | |

TABLE 1-2-continued
| Ex. No. | Structure Formula |
|---|---|
| 17 | 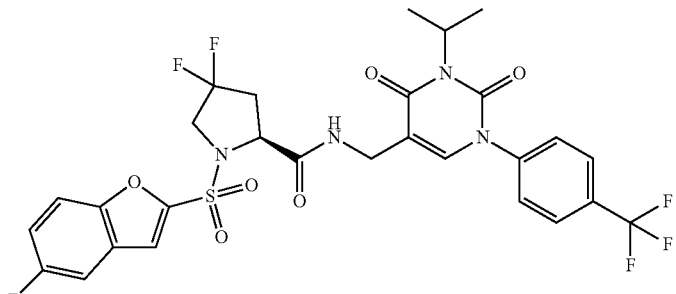 |
TABLE 1-3
| Ex. No. | Structure Formula |
|---|---|
| 18 | 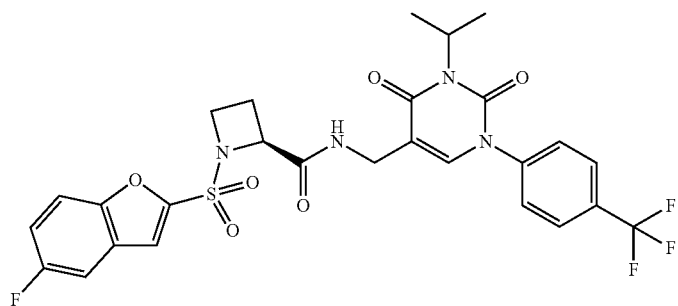 [SMILES: CC(C)n1c(=O)c(CNC(=O)[C@@H]2CCN2S(=O)(=O)c2cc3cc(F)ccc3o2)cn(-c2ccc(C(F)(F)F)cc2)c1=O] |
| 19 | 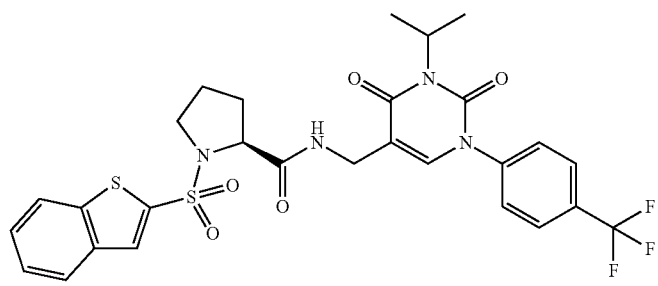 [SMILES: CC(C)n1c(=O)c(CNC(=O)[C@@H]2CCCN2S(=O)(=O)c2cc3ccccc3s2)cn(-c2ccc(C(F)(F)F)cc2)c1=O] |
| 20 | 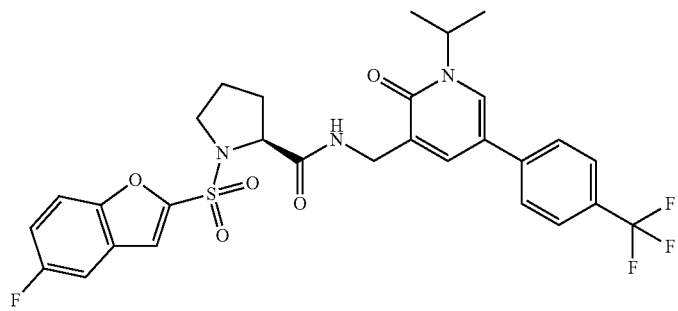 [SMILES: CC(C)n1cc(-c2ccc(C(F)(F)F)cc2)cc(CNC(=O)[C@@H]2CCCN2S(=O)(=O)c2cc3cc(F)ccc3o2)c1=O] |

TABLE 1-3-continued

| Ex. No. | Structure Formula |
| --- | --- |
| 21 | |
| 22 | |
| 23 | |

TABLE 1-4

| Ex. No. | Structure Formula |
| --- | --- |
| 24 | |

TABLE 1-4-continued

| Ex. No. | Structure Formula |
|---|---|
| 27 | |
| 29 | |
| 30 | |
| 33 | |
| 34 | |

TABLE 1-4-continued
| Ex. No. | Structure Formula |
|---|---|
| 37 | 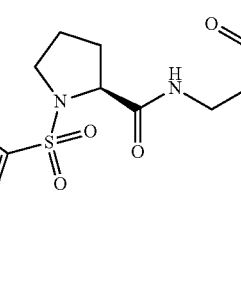 |
TABLE 1-5
| Ex. No. | Structure Formula |
|---|---|
| 40 | |
| 41 | |
| 42 | |

TABLE 1-5-continued

| Ex. No. | Structure Formula |
|---|---|
| 43 | |
| 45 | |
| 46 | |
| 49 | |
| 51 | |

EFFECT OF THE INVENTION

The compounds of the present invention have a TRPA1 antagonist activity, and possibly utilizable for the prophylaxis and/or treatment of diseases involving TRPA1 (e.g., pain associated diseases, digestive tract diseases, lung diseases, bladder diseases, inflammatory diseases, dermatic diseases, and neurological diseases).

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 shows the results of a blood flow evaluation test using the compound of Example 1 in allylisothiocyanate (AITC)-induced rats. The evaluation was made by varying the dose of the test compound for rat (upper panel: 0.3 mg/kg, middle panel: 1 mg/kg, lower panel: 3 mg/kg). AITC-induced increase in the blood flow was suppressed by the administration of the compound of the present invention.

DETAILED DESCRIPTION OF THE PREFERRED EMBODIMENTS

The terms used in the present specification are defined below.

The term "TRPA1 antagonist activity" refers to an activity capable of inhibiting activation of TRPA1, or down-regulating the biological activity of TRPA1 (e.g., intracellular influx of ion). The TRPA1 antagonist activity can be evaluated by measuring the level of intracellular influx of calcium ion into the cell expressing TRPA1.

The "halogen atom" is a fluorine atom, a chlorine atom, a bromine atom or an iodine atom.

The "halogeno group" is fluoro, chloro, bromo or iodo.

The term "alkyl group" means a straight chain or branched alkyl group having 1-10 carbon atoms and, specifically, groups such as methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl and the like can be mentioned.

As the "$C_{1-6}$ alkyl group", the above-mentioned "alkyl group" having a carbon number of 1 to 6 can be mentioned.

The term "$C_{2-6}$ alkenyl group" means a straight chain or branched alkenyl group having 2 to 6 carbon atoms and, specifically, groups such as vinyl, allyl, propenyl, butenyl, pentenyl, hexenyl, heptenyl, butadienyl, hexatrienyl, each isomer thereof and the like can be mentioned.

The term "$C_{6-10}$ aryl group" means an aryl group having 6 to 10 carbon atoms and, specifically, groups such as phenyl, naphthyl and the like can be mentioned.

The term "$C_{1-9}$ heteroaryl group" refers to a 5- to 10-membered monocyclic-bicyclic heteroaryl group having 1 to 9 carbon atoms and one or more hetero atoms selected from an oxygen atom, a nitrogen atom and a sulfur atom. Specifically, for example, 5- or 6-membered monocyclic heteroaryl groups such as pyridyl, pyridazinyl, pyrimidinyl, pyrazinyl, furyl, thiophenyl, pyrrolyl, pyrazolyl, imidazolyl, triazolyl, tetrazolyl, oxazolyl, isoxazolyl, thiazolyl, isothiazolyl, oxadiazolyl, thiadiazolyl and the like; bicyclic heteroaryl groups such as benzofuranyl, benzothiophenyl, indolyl, isoindolyl, benzoxazolyl, benzothiazolyl, benzimidazolyl, indazolyl, benzisoxazolyl, benzisothiazolyl, benzoxadiazolyl, benzothiadiazolyl, purinyl, quinolinyl, isoquinolinyl, cinnolinyl, phthalazinyl, quinazolinyl, quinoxalinyl, pteridinyl, imidazooxazolyl, imidazothiazolyl, imidazoimidazolyl, furopyridinyl and the like can be mentioned. Preferred is a bicyclic heteroaryl group.

The term "$C_{3-7}$ cycloalkyl group" refers to a cyclic alkyl group having a carbon number of 3 to 7 and, specifically, cyclopropyl, cyclobutyl, cyclopentyl, cyclohexyl, cycloheptyl and the like group can be mentioned.

The "alkyl group", "$C_{1-6}$ alkyl group", "$C_{2-6}$ alkenyl group", "$C_{6-10}$ aryl group", "$C_{1-9}$ heteroaryl group" and "$C_{3-7}$ cycloalkyl group" may have substituent(s) and, as such substituent, the following, substituent group A, can be mentioned.

substituent group A (1) halogeno group,
(2) hydroxy group,
(3) cyano group,
(4) nitro group,
(5) carboxyl group,
(6) alkenyl group ($C_{2-10}$ alkenyl group; e.g., vinyl, allyl, propenyl, butenyl, pentenyl, hexenyl, heptenyl, butadienyl, hexatrienyl, each isomer thereof),
(7) alkynyl group ($C_{2-10}$ alkynyl group; e.g., ethynyl, propynyl, butynyl, pentynyl, hexynyl, and each isomer thereof),
(8) halogenoalkyl group (e.g., monofluoromethyl, difluoromethyl, trifluoromethyl, monofluoroethyl, difluoroethyl, trifluoroethyl, chloromethyl, chloroethyl, dichloroethyl, each isomer thereof),
(9) cyclic alkyl group (optionally containing heteroatom(s) in the ring) (e.g., cyclopropyl, cyclobutyl, cyclopentyl, cyclohexyl, tetrahydrofuranyl, tetrahydropyranyl, aziridinyl, azetidinyl, pyrrolidinyl, piperidinyl, morpholinyl),
(10) aryl group (e.g., phenyl, naphthyl),
(11) heteroaryl group (e.g., pyridyl, pyridazinyl, pyrimidinyl, pyrazinyl, furyl, thiophenyl, pyrrolyl, pyrazolyl, imidazolyl, triazolyl (e.g., 1,2,3-triazolyl, 1,2,4-triazolyl), tetrazolyl, oxazolyl, isoxazolyl, thiazolyl, isothiazolyl, oxadiazolyl (e.g., 1,2,3-oxadiazolyl, 1,2,4-oxadiazolyl, 1,3,4-oxadiazolyl), thiadiazolyl (e.g., 1,2,3-thiadiazolyl, 1,2,4-thiadiazolyl, 1,3,4-thiadiazolyl), benzofuryl, benzothiophenyl, indolyl, isoindolyl, benzoxazolyl, benzothiazolyl, benzimidazolyl, indazolyl, benzisoxazolyl, benzisothiazolyl, benzoxadiazolyl, benzothiadiazolyl, purinyl, quinolinyl, isoquinolinyl, cinnolinyl, phthalazinyl, quinazolinyl, quinoxalinyl, pteridinyl, imidazooxazolyl, imidazothiazolyl, imidazoimidazolyl),
(12) alkoxy group (e.g., methoxy, ethoxy, n-propoxy, isopropoxy, n-butoxy, isobutoxy, sec-butoxy, tert-butoxy, n-pentyloxy, isopentyloxy, tert-pentyloxy, neopentyloxy, 2-pentyloxy, 3-pentyloxy, n-hexyloxy, 2-hexyloxy),
(13) alkylthio group (e.g., methylthio, ethylthio, n-propylthio, isopropylthio, n-butylthio, isobutylthio, sec-butylthio, tert-butylthio, n-pentylthio, isopentylthio, tert-pentylthio, neopentylthio, 2-pentylthio, 3-pentylthio, n-hexylthio, 2-hexylthio),
(14) alkoxy group (as defined in the above-mentioned (12)) substituted by an aryl group (as defined in the above-mentioned (10)),
(15) alkylthio group (as defined in the above-mentioned (13)) substituted by an aryl group (as defined in the above-mentioned (10)),
(16) alkoxy group (as defined in the above-mentioned (12)) substituted by a heteroaryl group (as defined in the above-mentioned (11)),

(17) alkylthio group (as defined in the above-mentioned (13)) substituted by a heteroaryl group (as defined in the above-mentioned (11)),

(18) cyclic alkyl (optionally containing heteroatom(s) in the ring) oxy group (e.g., cyclopropyloxy, cyclobutyloxy, cyclopentyloxy, cyclohexyloxy, tetrahydrofuranyloxy, tetrahydropyranyloxy, aziridinyloxy, azetidinyloxy, pyrrolidinyloxy, piperidinyloxy, morpholinyloxy),

(19) aryloxy group (e.g., group wherein aryl group (the above-mentioned (10)) is bonded to oxygen atom),

(20) heteroaryloxy group (e.g., group wherein heteroaryl group (as defined in the above-mentioned (11)) is bonded to oxygen atom),

(21) halogenoalkoxy group (e.g., group wherein halogenoalkyl group (as defined in the above-mentioned (8)) is bonded to oxygen atom),

(22) halogenoalkylthio group (e.g., group wherein halogenoalkyl group (as defined in the above-mentioned (8)) is bonded to sulfur atom),

(23) alkoxy group (as defined in the above-mentioned (12)) substituted by hydroxy group,

(24) alkoxy group (as defined in the above-mentioned (12)) substituted by alkoxy group (as defined in the above-mentioned (12)),

(25) amino group,

(26) amino group mono- or di-substituted by alkyl group, wherein "alkyl group" is, for example, $C_{1-6}$ alkyl group, specifically, methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl and the like,

(27) carbamoyl group,

(28) carbamoyl group mono- or di-substituted by alkyl group (same as the "alkyl group" in the above-mentioned (26)") (e.g., methylcarbamoyl, ethylcarbamoyl, dimethylcarbamoyl, diethylcarbamoyl, ethylmethylcarbamoyl),

(29) sulfamoyl group,

(30) sulfamoyl group mono- or di-substituted by alkyl group (same as the "alkyl group" in the above-mentioned (26)") (e.g., methylsulfamoyl, ethylsulfamoyl, dimethylsulfamoyl, diethylsulfamoyl, ethylmethylsulfamoyl),

(31) alkanoyl group (e.g., carbonyl group wherein a hydrogen atom or alkyl group (same as the "alkyl group" in the above-mentioned (26)") is bonded to carbon atom),

(32) aroyl group (e.g., carbonyl group wherein aryl group (as defined in the above-mentioned (10)) is bonded to carbon atom),

(33) alkylsulfonylamino group (e.g., sulfonylamino group substituted by alkyl group (same as the "alkyl group" in the above-mentioned (26)))

(34) arylsulfonylamino group (e.g., sulfonylamino group substituted by aryl group (as defined in the above-mentioned (10))),

(35) heteroarylsulfonylamino group (e.g., sulfonylamino group substituted by heteroaryl group (as defined in the above-mentioned (11))),

(36) acylamino group (e.g., amino group substituted by acyl group), wherein the "acyl group" is an acyl group having a $C_{1-6}$ alkyl group, a $C_{3-7}$ cycloalkyl group, or $C_{6-10}$ aryl group; as the $C_{1-6}$ alkyl group, a cyclic $C_{3-6}$ alkyl group and $C_{6-10}$ aryl group, those recited above can be mentioned; as the acyl group, specifically, acetyl group, propionyl group, butyroyl group, isobutyroyl group, valeroyl group, isovaleroyl group, pivaloyl group, hexanoyl group, acryloyl group, methacryloyl group, crotonoyl group, isocrotonoyl group, benzoyl group, naphthoyl group and the like can be mentioned,

(37) alkoxycarbonylamino group (e.g., carbonylamino group substituted by alkoxy group (as defined in the above-mentioned (12))),

(38) alkylsulfonyl group (e.g., sulfonyl group substituted by alkyl group (same as the "alkyl group" in the above-mentioned (26))),

(39) alkylsulfinyl group (e.g., sulfinyl group substituted by alkyl group (the same as the "alkyl group" in the above-mentioned (26))),

(40) alkoxycarbonyl group (e.g., methoxycarbonyl group, ethoxycarbonyl group), and the like.

When two or more substituents are present, they may be the same or different.

The "cycloalkane" is a carbocycle having a carbon number of 3 to 10, preferably 3 to 8, more preferably 3 to 6 and, for example, cyclopropane, cyclobutane, cyclopentane, cyclohexane, cycloheptane, cyclooctane, cyclononane or cyclodecane.

The "cycloalkene" is nonaromatic cyclic alkene having a carbon number of 3 to 10, preferably 3 to 8, more preferably 3 to 6, and having not less than one double bond in a molecule, for example, cyclopropene, cyclobutene, cyclopentene, cyclohexene, cycloheptene, or 1,3-cyclohexadiene.

The "$C_{1-6}$ alkoxycarbonyl group" is a straight chain or branched alkoxycarbonyl group having 1 to 6 carbon atoms and, specifically, methoxycarbonyl, ethoxycarbonyl and the like group can be mentioned. The "$C_{1-6}$ alkoxycarbonyl group" may have substituent(s) and examples of such substituent include those shown in the above-mentioned [substituent group A].

The terms "halogeno $C_{1-6}$ alkyl group" and "halogeno $C_{1-6}$ alkoxy group" mean a $C_{1-6}$ alkyl group and a $C_{1-6}$ alkoxy group, respectively, each of which is substituted by one or more halogeno groups. As the "halogeno $C_{1-6}$ alkyl group", specifically, groups such as monofluoromethyl, difluoromethyl, trifluoromethyl, monofluoroethyl, difluoroethyl, trifluoroethyl, chloromethyl, chloroethyl, dichloroethyl, each isomer thereof and the like can be mentioned. The "halogeno $C_{1-6}$ alkoxy group" specifically means a $C_{1-6}$ alkoxy group substituted by one or more halogeno groups and, specifically, groups such as monofluoromethoxy, difluoromethoxy, trifluoromethoxy, monofluoroethoxy, difluoroethoxy, trifluoroethoxy, chloromethoxy, chloroethoxy, dichloroethoxy, each isomer thereof and the like can be mentioned.

The term "saturated or unsaturated cyclic group (optionally containing heteroatom(s))" means a group derived from a saturated or unsaturated carbocycle (preferably carbon number 5 to 15) or heterocycle (preferably 5-membered to 15-membered).

As the saturated or unsaturated carbocycle, $C_{5-15}$ unsaturated monocycle, bicyclic or tricyclic carbocycle, monocyclic, bicyclic or tricyclic carbocycle in which a part or whole thereof is saturated, spiro-bonded bicyclic carbocycle and bridged bicyclic carbocycle can be mentioned. Examples thereof include cyclopentane, cyclohexane, cycloheptane, cyclopentene, cyclohexene, cycloheptene, cyclopentadiene, cyclohexadiene, cycloheptadiene, benzene, pentalene, perhydropentalene, azulene, perhydroazulene, indene, perhydroindene, indane, naphthalene, dihydronaphthalene, tetrahydronaphthalene, perhydronaphthalene, biphenylene, as-indacene, s-indacene, fluorene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, and noradamantane rings.

As the saturated or unsaturated heterocycle, 5-15-membered unsaturated monocyclic, bicyclic or tricyclic heterocycle, or monocyclic, bicyclic or tricyclic heterocycle in which a part or whole thereof is saturated, containing, besides at least one carbon atom, 1 to 4 nitrogen atoms, 1 to 2 oxygen atoms and/or 1 to 2 sulfur atoms. Examples thereof include pyrrole, imidazole, triazole, tetrazole, pyrazole, pyridine, pyrazine, triazine, pyrimidine, pyridazine, azepine, diazepine, furan, pyran, oxepin, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzoazepine, benzodiazepine, benzofurazan, benzothiadiazole, benzotriazole, carbazole, β-carboline, acridine, phenazine, dibenzofuran, xanthene, dibenzothiophene, phenothiazine, phenoxathiin, thianthrene, phenanthridine, phenanthroline, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole(oxazolidine), dihydroisoxazole, tetrahydroisoxazole(isoxazolidine), dihydrothiazole, tetrahydrothiazole(thiazolidine), dihydroisothiazole, tetrahydroisothiazole(isothiazolidine), dihydrofurazan, tetrahydrofurazan, dihydrooxadiazole, tetrahydrooxadiazole(oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole(thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridins, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzoazepine, tetrahydrobenzoazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindane, benzodioxane, chromane, benzodithiolane, benzodithiane and the like.

The term "nitrogen-containing heterocycle" means the above-mentioned "saturated or unsaturated heterocycle" containing at least one nitrogen atom.

The "nitrogen-containing heterocycle" and "saturated or unsaturated cyclic group (optionally containing heteroatom(s))" may have substituent(s), and examples of such substituent include alkyl groups (e.g., methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl) in addition to the groups exemplified as the above-mentioned "substituent group A" (hereinafter "substituent group B").

When two or more substituents are present, they may be the same or different.

The term "6-membered, nitrogen-containing heterocycle substituted by 1 or 2 oxo groups" means the above-mentioned "saturated or unsaturated heterocycle" which is 6-membered, contains at least one nitrogen atom, and is characterized in that it is substituted by 1 or 2 oxo groups at substitutable position(s) of the ring. As the "6-membered, nitrogen-containing heterocycle" of the "6-membered, nitrogen-containing heterocycle substituted by 1 or 2 oxo groups", specifically, piperidine, pyridine, pyrazine, piperazine, pyrimidine, pyridazine and the like can be mentioned. The "6-membered, nitrogen-containing heterocycle substituted by 1 or 2 oxo groups" is preferably oxopyridine, dioxopyridine, oxopyrimidine, dioxopyrimidine and the like, more preferably oxopyridine or dioxopyrimidine, particularly preferably dioxopyrimidine.

The "6-membered, nitrogen-containing heterocycle substituted by 1 or 2 oxo groups" may have substituent(s), and examples of such substituent include the above-mentioned "substituent group A" and "substituent group B".

When two or more substituents are present, they may be the same or different.

The present invention provides compounds represented by formula (I):

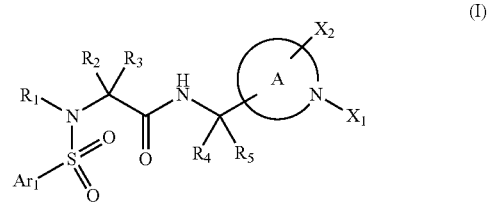

wherein each symbol is as defined above, (hereinafter to be also referred to as compound (I)), or a pharmaceutically acceptable salt thereof.

In formula (I),
$R_1$ is a hydrogen or a $C_{1-6}$ alkyl group optionally having substituent(s) (e.g., $C_{1-6}$ alkenyl group, hydroxy group, halogeno group) (preferably a hydrogen or a $C_{1-6}$ alkyl group); $R_2$ is a hydrogen or a $C_{1-6}$ alkyl group optionally having substituent(s) (e.g., a hydroxy group) (e.g., preferably hydroxymethyl), or a $C_{2-6}$ alkenyl group optionally having substituent(s). $R_1$ and $R_2$ are optionally joined to form a nitrogen-containing ring optionally having substituent(s). Preferably, $R_1$ and $R_2$ are joined to form a nitrogen-containing ring optionally having substituent(s). As used herein, examples of the nitrogen-containing ring optionally having substituent(s), which is optionally formed by $R_1$ and $R_2$ in combination, include the following rings.

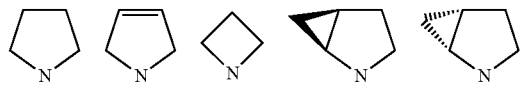

preferably

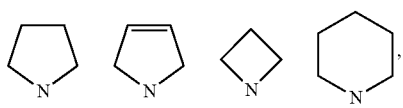

more preferably

Examples of the substituent that the nitrogen-containing ring optionally formed by $R_1$ and $R_2$ in combination optionally has include those exemplified by the above-mentioned [substituent group A]. Preferably, it is free of substituent(s), or a hydroxy group and a halogeno group (e.g., fluoro) can be mentioned. Further, preferably, the nitrogen-containing ring does not have substituent(s).

In addition, a derivative wherein $R_1$ is a hydrogen and $R_2$ is a $C_{1-6}$ alkyl group is also similarly preferable.

In formula (I), the partial structure (a):

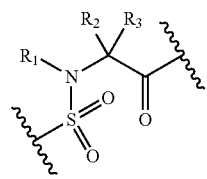

(a)

is preferably any of the following groups.

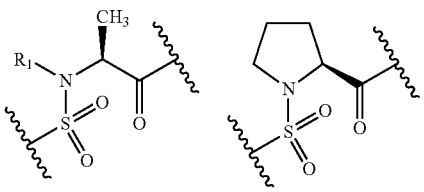

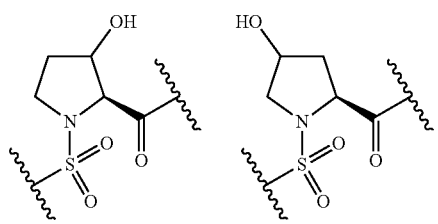

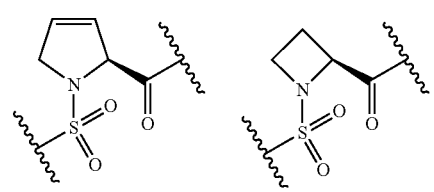

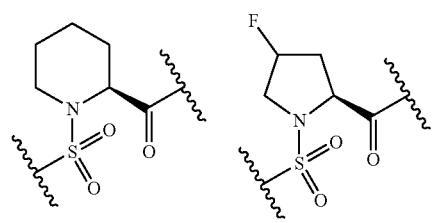

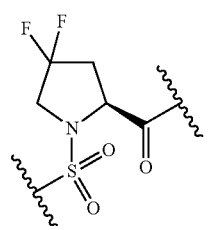

preferably,

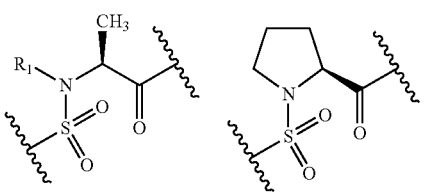

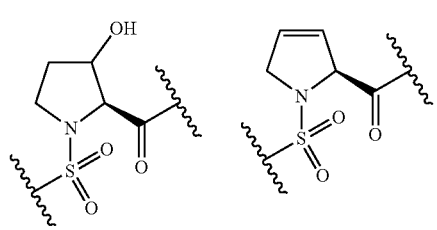

-continued

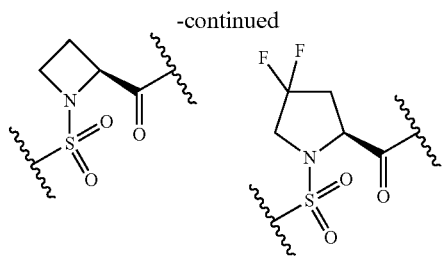

more preferably,

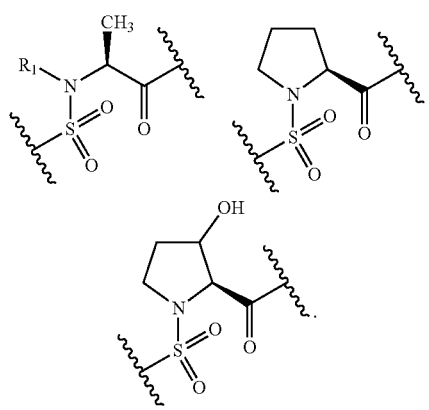

In formula (I), $R_3$ is a hydrogen or a $C_{3-6}$ alkyl group, preferably a hydrogen. $R_3$ and $R_2$ are optionally joined to form cycloalkene or cycloalkane.

In formula (I), ring A is a 6-membered, nitrogen-containing heterocycle substituted by 1 or 2 oxo groups. The "6-membered, nitrogen-containing heterocycle substituted by 1 or 2 oxo groups" is preferably oxopyridine, dioxopyridine, oxopyrimidine, dioxopyrimidine or the like, more preferably oxopyridine or dioxopyrimidine, particularly preferably dioxopyrimidine.

In formula (I), $R_4$ and $R_5$ are the same or different and each is a hydrogen or a $C_{1-6}$ alkyl group, or $R_4$ and $R_5$ are optionally joined to form cycloalkane (e.g., cyclopropane). Preferably, $R_4$ and $R_5$ are the same or different and each is a hydrogen or a $C_{1-6}$ alkyl group (wherein $R_4$ and $R_5$ are not joined to form cycloalkane), more preferably, $R_4$ and $R_5$ are hydrogens.

In formula (I), $Ar_1$ is a $C_{6-10}$ aryl group optionally having substituent(s), a $C_{1-9}$ heteroaryl group optionally having substituent(s) or a $C_{3-7}$ cycloalkyl group optionally having substituent(s). $Ar_1$ is preferably a $C_{6-10}$ aryl group optionally having substituent(s) (preferably, a halogen atom), or a $C_{1-9}$ heteroaryl group optionally having substituent(s) (preferably, halogen atom, alkyl group), more preferably a $C_{1-9}$ heteroaryl group optionally having substituent(s) (preferably, halogen atom), further preferably a benzofuranyl group unsubstituted or substituted by a halogen atom.

In formula (I), one of $X_1$ and $X_2$ is one kind selected from the following Group A, and the other is an alkyl group optionally having substituent(s) (substituents are optionally joined to form a ring) or a hydrogen atom. $X_1$ is not a hydrogen atom when ring A is a ring having a pyridone skeleton, and $X_1$ and $X_2$ are not hydrogen atoms at the same time.

Group A:
(a) hydrogen,
(b) -Cy,
(c) —C($R_{x1}R_{x2}$)-Cy,
(d) —C($R_{x1}R_{x2}$)—C($R_{x3}R_{x4}$)-Cy,
(e) —C($R_{x1}$)=C($R_{x2}$)-Cy,
(f) —O-Cy,
(g) —O—C($R_{x1}R_{x2}$)-Cy,
(h) —C($R_{x1}R_{x2}$)—O-Cy,
(i) —S(O)n-Cy,
(j) —S(O)n-C($R_{x1}R_{x2}$)-Cy,
(k) —C($R_{x1}R_{x2}$)—S(O)n-Cy,
(l) —N($R_{x5}$)-Cy,
(m) —N($R_{x5}$)—C($R_{x1}R_{x2}$)-Cy,
(n) —C($R_{x1}R_2$)—N($R_{x5}$)-Cy,
(o) —C(O)—N($R_{x5}$)-Cy,
(p) —N($R_{x5}$)—C(O)-Cy,
(q) —S(O)m-N($R_{x5}$)-Cy,
(r) —N($R_{x5}$)—S(O)m-Cy, or
(s) —O—S(O)m-Cy,
preferably,
(b) -Cy,
(c) —C($R_{x1}R_{x2}$)-Cy,
(d) —C($R_{x1}R_{x2}$)—C($R_{x3}R_{x4}$)-Cy,
(e) —C($R_{x1}$)=C($R_{x2}$)-Cy,
(f) —O-Cy,
(g) —O—C($R_{x1}R_{x2}$)-Cy,
(h) —C($R_{x1}R_{x2}$)—O-Cy,
(i) —S(O)n-Cy,
(j) —S(O)n-C($R_{x1}R_{x2}$)-Cy,
(k) —C($R_{x1}R_{x2}$)—S(O)n-Cy,
(l) —N($R_{x5}$)-Cy,
(m) —N($R_{x5}$)—C($R_{x1}R_{x2}$)-Cy,
(n) —C($R_{x1}R_{x2}$)—N($R_{x5}$)-Cy,
(o) —C(O)—N($R_{x5}$)-Cy,
(p) —N($R_{x5}$)—C(O)-Cy,
(q) —S(O)m-N($R_{x5}$)-Cy, or
(r) —N($R_{x5}$)—S(O)m-Cy,
further preferably
(b) -Cy,
(d) —C($R_{x1}R_{x2}$)—C($R_{x3}R_{x4}$)-Cy,
(f) —O-Cy,
(g) —O—C($R_{x1}R_{x2}$)-Cy,
particularly preferably
(b) -Cy
(wherein each symbol is as defined in formula (I)).

Cy is a saturated or unsaturated cyclic group optionally having substituent(s) (optionally containing heteroatom(s)), preferably a monocyclic or bicyclic, saturated or unsaturated cyclic group (optionally containing heteroatom(s)), more preferably, a monocyclic saturated or unsaturated cyclic group (optionally containing heteroatom(s)). Specifically preferably, it is cyclopentane, cyclohexane, cyclohexene, benzene, naphthalene, pyrrole, imidazole, triazole, tetrazole, pyrazole, pyridine, pyrazine, triazine, pyrimidine, pyridazine, furan, thiophene, oxazole, isoxazole, thiazole, isothiazole, oxadiazole, thiadiazole, indole, benzofuran, benzothiophene, quinoline, isoquinoline, quinazoline, benzoxazole, benzothiazole, benzimidazole, tetrahydrofuran, dihydropyran or tetrahydropyran, further preferably, cyclopentane, cyclohexane, benzene, pyrazole, pyridine, pyrimidine, pyridazine, furan, thiophene, tetrahydrofuran or tetrahydropyran, particularly preferably benzene or pyridine.

As regards Cy, examples of the substituent that the "saturated or unsaturated cyclic group (optionally containing heteroatom(s))" optionally has include those exemplified as the above-mentioned "substituent group B". Preferably, it is unsubstituted, or alkyl group, alkenyl group, halogenoalkyl group, cyclic alkyl group (optionally containing heteroatom(s) in the ring), halogeno group, hydroxy group, alkoxy group, halogenoalkoxy group, amino group, amino group mono- or di-substituted by alkyl group, cyano group, alkylthio group, carboxyl group, alkoxycarbonyl group, carbamoyl group, carbamoyl group mono- or di-substituted by alkyl group, acylamino group or the like. Further preferably, it is unsubstituted, or halogeno group, halogenoalkyl group, hydroxy group, halogenoalkoxy group, or cyano group.

$R_{x1}$, $R_{x2}$, $R_{x3}$, $R_{x4}$, and $R_{x5}$ are the same or different and each is a hydrogen, a $C_{1-6}$ alkyl group optionally having substituent(s) or a $C_{1-6}$ alkoxycarbonyl group optionally having substituent(s). Preferred is hydrogen.

Cy is preferably a group of any of the following formulas:

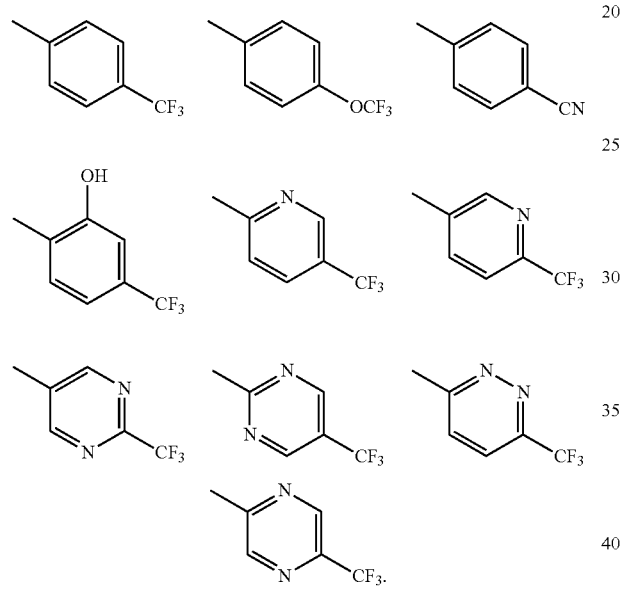

Cy is also preferably a group of any of the following formulas.

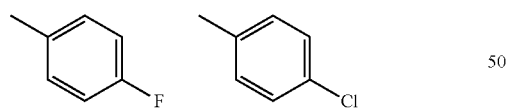

Cy is particularly preferably a group of any of the following formulas.

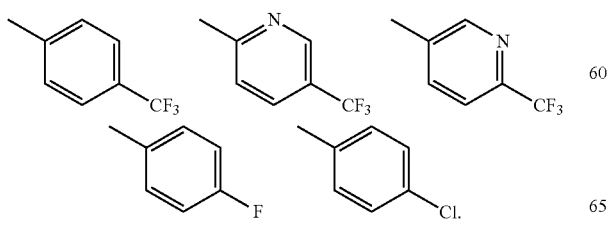

In formula (I), the partial structure (b) containing ring A:

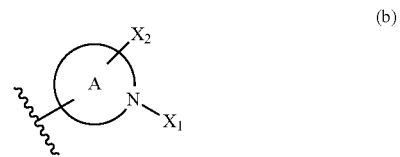

(b)

is preferably a group of any of the following formulas:

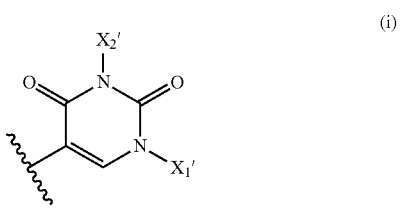

(i)

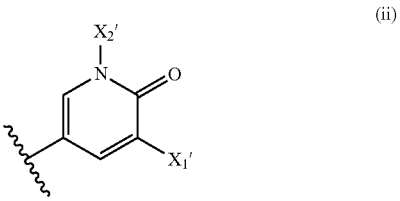

(ii)

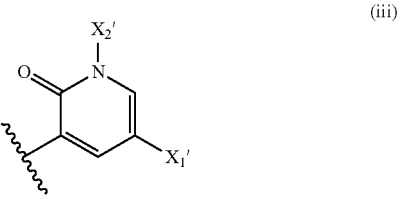

(iii)

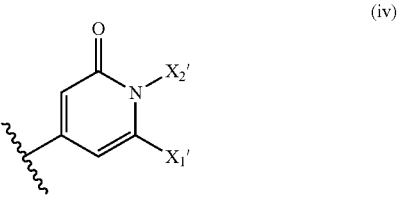

(iv)

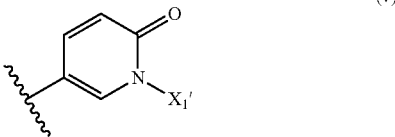

(v)

wherein
$X_1'$ is one kind selected from the following Group B;
Group B:
-Cy,
—C($R_{x1}R_{x2}$)-Cy,
—C($R_{x1}R_{x2}$)—C($R_{x3}R_{x4}$)-Cy,
—C($R_{x1}$)=C($R_{x2}$)-Cy,
—O-Cy,
—O—C($R_{x1}R_{x2}$)-Cy,
—C($R_{x1}R_{x2}$)—O-Cy,
—S(O)n-Cy,
—S(O)n-C($R_{x1}R_{x2}$)-Cy,
—C($R_{x1}R_{x2}$)—S(O)n-Cy,
—N($R_{x5}$)-Cy,
—N($R_{x5}$)—C($R_{x1}R_{x2}$)-Cy, —C(R$_{x1}$R$_{x2}$)—N(R$_{x5}$)-Cy,
—C(O)—N(R$_{x5}$)-Cy,
—N(R$_{x5}$)—C(O)-Cy,
—S(O)m-N(R$_{x5}$)-Cy,
—N(R$_{x5}$)—S(O)m-Cy,
—O—S(O)m-Cy wherein n is an integer of 0 to 2; m is 1 or 2; Cy is a saturated or unsaturated cyclic group optionally having substituent(s) (optionally containing heteroatom(s)); R$_{x1}$, R$_{x2}$, R$_{x3}$, R$_{x4}$, and R$_{x5}$ are the same or different and each is a hydrogen, a C$_{1-6}$ alkyl group optionally having substituent(s) or a C$_{1-6}$ alkoxycarbonyl group optionally having substituent(s); and X$_2$' is an alkyl group optionally having substituent(s) (substituents are optionally joined to form a ring).

More preferably, the partial structure (b) containing ring A is a group represented by the formula (i), (ii), (iii) or (v), particularly preferably a group represented by the formula (i).

A compound represented by formula (I) is sometimes to be also referred to as the compound of the present invention.

Preferable compounds of the present invention include the following compounds.

(1) A compound of formula (I), wherein
R$_1$ is a hydrogen or a C$_{1-6}$ alkyl group optionally having substituent(s);
R$_2$ is a hydrogen or a C$_{1-6}$ alkyl group optionally having substituent(s);
R$_3$ is a hydrogen;
R$_4$ is a hydrogen or a C$_{1-6}$ alkyl group;
R$_5$ is a hydrogen or a C$_{1-6}$ alkyl group;
X$_1$ is
-Cy,
—C(R$_{x1}$R$_{x2}$)-Cy,
—C(R$_{x1}$R$_{x2}$)—C(R$_{x3}$R$_{x4}$)-Cy,
—C(R$_{x1}$)=C(R$_{x2}$)-Cy,
—O-Cy,
—O—C(R$_{x1}$R$_{x2}$)-Cy,
—C(R$_{x1}$R$_{x2}$)—O-Cy,
—S(O)n-Cy,
—S(O)n-C(R$_{x1}$R$_{x2}$)-Cy,
—C(R$_{x1}$R$_{x2}$)—S(O)n-Cy,
—N(R$_{x5}$)-Cy,
—N(R$_{x5}$)—C(R$_{x1}$R$_{x2}$)-Cy,
—C(R$_{x1}$R$_{x2}$)—N(R$_{x5}$)-Cy,
—C(O)—N(R$_{x5}$)-Cy,
—N(R$_{x5}$)—C(O)-Cy,
—S(O)m-N(R$_{x5}$)-Cy,
—N(R$_{x5}$)—S(O)m-Cy, or
—O—S(O)m-Cy; and X$_2$ is an alkyl group optionally having substituent(s) (substituents are optionally joined to form a ring) (compound I-1);

(2) a compound of formula (I), wherein the 6-membered, nitrogen-containing heterocycle substituted by 1 or 2 oxo groups is selected from the group consisting of oxopyridine, dioxopyridine, oxopyrimidine and dioxopyrimidine (compound I-2), particularly oxopyridine or dioxopyrimidine (compound I-2-1);

(3) a compound of formula (I), wherein R$_1$ and R$_2$ are joined to form a nitrogen-containing ring optionally having substituent(s) (compound I-3);

(4) a compound of formula (I), wherein R$_1$ is a hydrogen, and R$_2$ is a C$_{1-6}$ alkyl group (compound I-4);

(5) a compound of formula (I), wherein the partial structure (a):

(a)

is a group of any of the following formulas:

(compound I-5), particularly the compound wherein the partial structure (a) is a group of any of the following formulas:

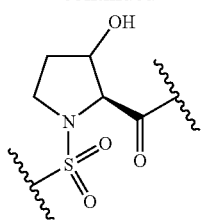

(compound I-5-1);

(6) a compound of formula (I), wherein the partial structure (b) containing ring A:

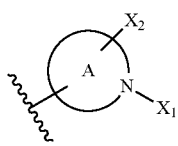

is a group of any of the following formulas:

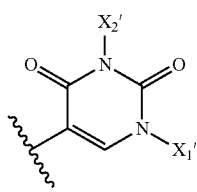 (i)

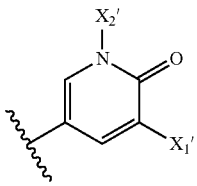 (ii)

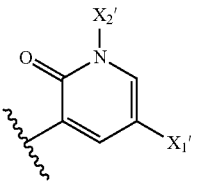 (iii)

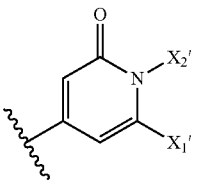 (iv)

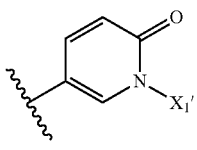 (v)

wherein
$X_1'$ is one kind selected from the following Group B;
Group B:
-Cy,
—C($R_{x1}R_{x2}$)-Cy,
—C($R_{x1}R_{x2}$)—C($R_{x3}R_{x4}$)-Cy,
—C($R_{x1}$)=C($R_{x2}$)-Cy,
—O-Cy,
—O—C($R_{x1}R_{x2}$-Cy,
—C($R_{x1}R_{x2}$)—O-Cy,
—S(O)n-Cy,
—S(O)n-C($R_{x1}R_{x2}$)-Cy,
—C($R_{x1}R_{x2}$)—S(O)n-Cy,
—N($R_{x5}$)-Cy,
—N($R_{x5}$)—C($R_{x1}R_{x2}$)-Cy,
—C($R_{x1}R_{x2}$)—N($R_{x5}$)-Cy,
—C(O)—N($R_{x5}$)-Cy,
—N($R_{x5}$)—C(O)-Cy,
—S(O)m-N($R_{x5}$)-Cy,
—N($R_{x5}$)—S(O)m-Cy, or
—O—S(O)m-Cy wherein n is an integer of 0 to 2; m is 1 or 2; Cy is a saturated or unsaturated cyclic group optionally having substituent(s) (optionally containing heteroatom(s)); $R_{x1}$, $R_{x2}$, $R_{x3}$, $R_{x4}$, and $R_{x5}$ are the same or different and each is a hydrogen, a $C_{1-6}$ alkyl group optionally having substituent(s) or a $C_{1-6}$ alkoxycarbonyl group optionally having substituent(s); and $X_2'$ is an alkyl group optionally having substituent(s) (substituents are optionally joined to form a ring) [compound I-6], particularly the compound wherein the partial structure (b) is the formula (i), (ii), (iii) or (v) [compound I-6'], particularly the compound wherein partial structure (b) is the formula (i) (compound I-6");

(7) a compound of formula (I), wherein $Ar_1$ is a $C_{6-10}$ aryl group having one or more substituents selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group having one or more substituents selected from a halogeno group, a halogeno-$C_{1-6}$ alkyl group, a halogeno-$C_{1-6}$ alkoxy group, and a $C_{1-6}$ alkyl group (compound I-7);

(8) a compound, wherein in compound I-6, compound I-6' or compound I-6", $X_1'$ is -Cy, —O-Cy, —O—$CH_2$-Cy, or —$CH_2$—$CH_2$-Cy (compound I-6-1), particularly the compound wherein $X_1'$ is -Cy (compound I-6-2);

(9) a compound, wherein, in compound I-6-1 or compound I-6-2, Cy is benzene optionally having substituent(s), pyridine optionally having substituent(s), pyrimidine optionally having substituent(s), pyridazine optionally having substituent(s), or pyrazine optionally having substituent(s) (compound I-6-3);

(10) a compound, wherein in compound I-6-1 or compound I-6-2, Cy is a group of any of the following formulas

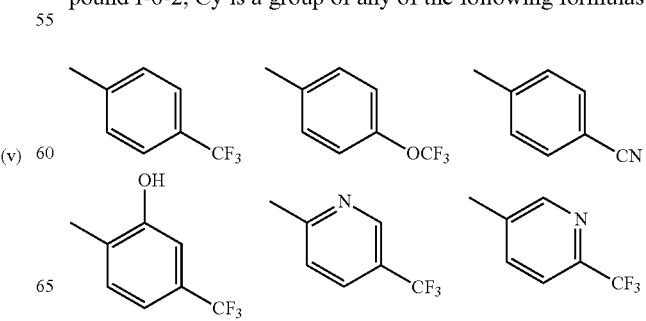

-continued

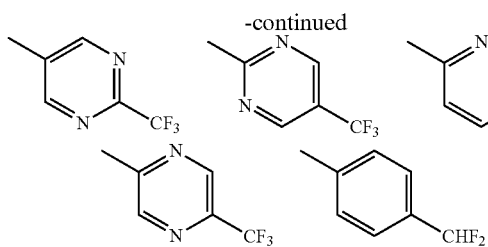

(compound I-6-4); particularly the compound wherein Cy is a group of any of the following formulas

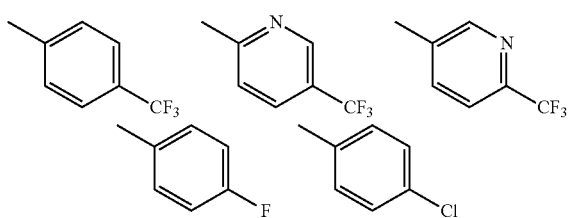

(compound I-6-4'), particularly the compound wherein Cy is a group of any of the following formulas

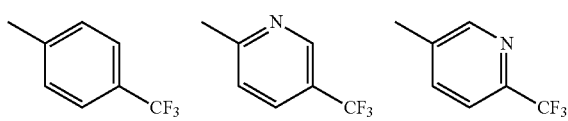

(compound I-6-4");

(11) a compound of formula (I), wherein $R_4$ and $R_5$ are hydrogens; the partial structure (b) containing ring A:

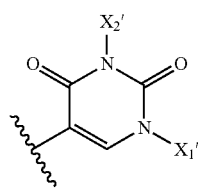

is the following formula (i):

wherein
X1' is -Cy;
Cy is a group of any of the following formulas;

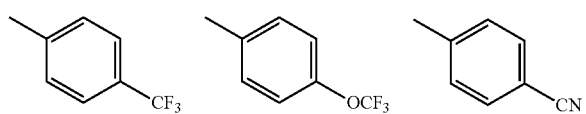

-continued

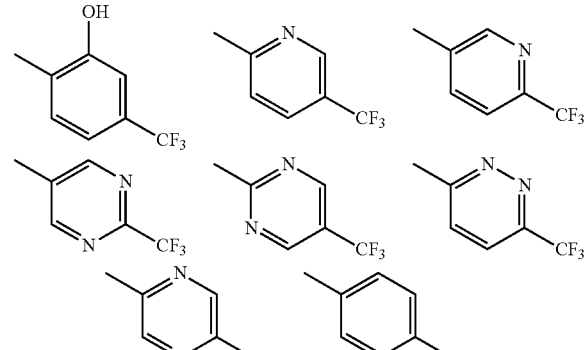

and
$Ar_1$ is a group of any of the following formulas:

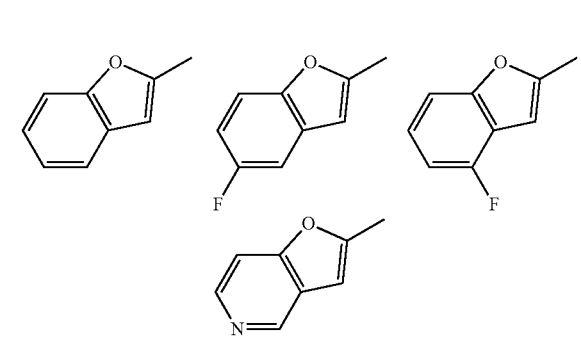

(compound I-8); particularly the compound wherein Cy is a group of any of the following formulas

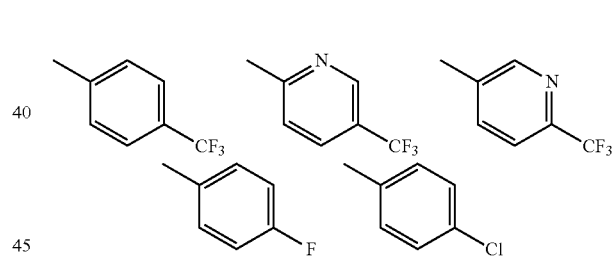

(compound I-8');

(12) a compound of formula (I), wherein
$R_4$ and $R_5$ are hydrogen; the partial structure (b) containing ring A is a group represented by the formula (i), (ii), (iii) or (v);
$X_1'$ is -Cy;
Cy is a group of any of the following formulas:

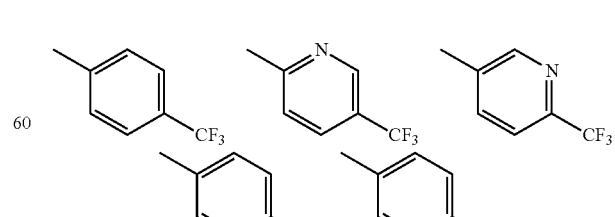

and

Ar₁ is a group of any of the following formulas:

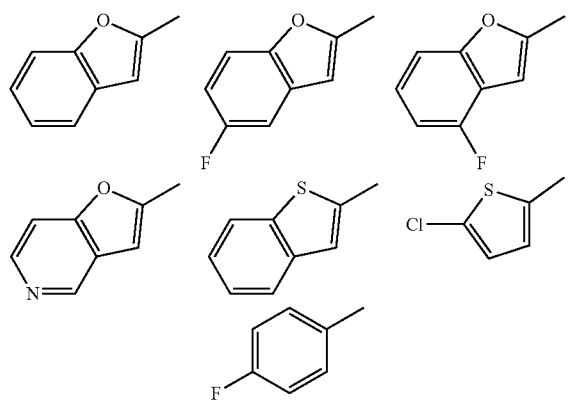

(compound I-9), particularly the compound wherein Ar₁ is a group of any of the following formulas:

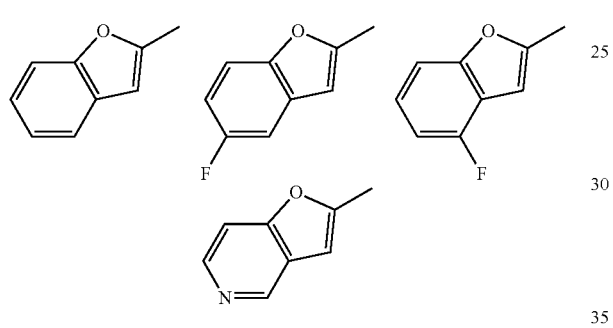

(compound I-9');

(13) a compound of formula (I), wherein
R₄ and R₅ are hydrogens;
the partial structure (b) containing ring A is a group represented by the formula (i);
X₁' is -Cy;
Cy is a group of any of the following formulas:

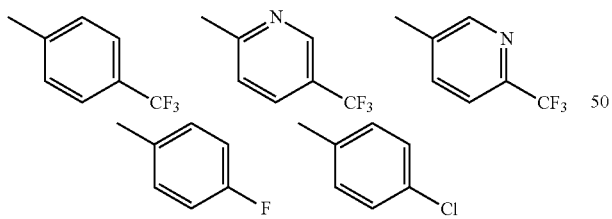

and
Ar₁ is a group of any of the following formulas:

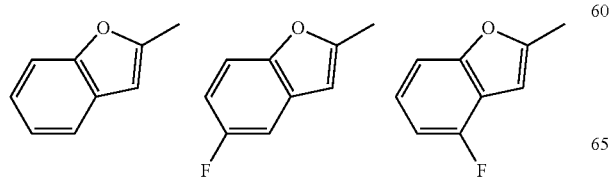

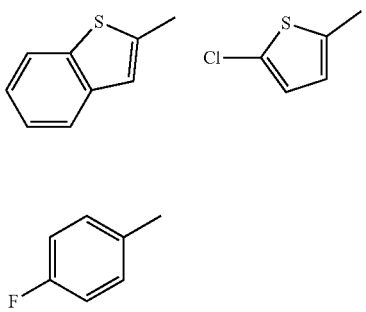

(compound I-10);

(14) a compound of formula (I), wherein
Ar₁ is a group of any of the following formulas:

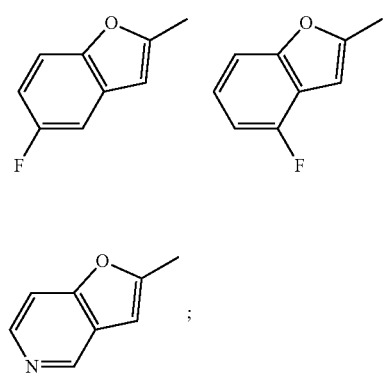

the partial structure (a):

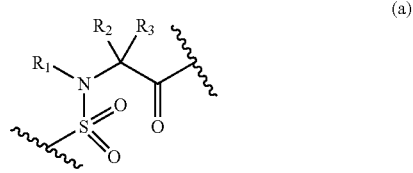

is a group of any of the following formulas:

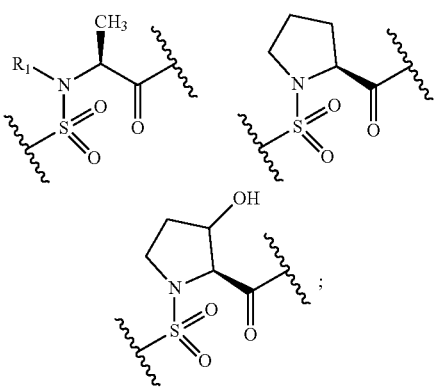

R₄ and R₅ are hydrogens;
the partial structure (b) containing ring A is a group represented by the formula (i), (ii), (iii) or (v);
X₁' is -Cy; and
Cy is a group of any of the following formulas:

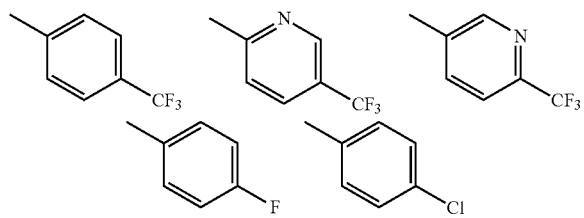

(compound I-11), particularly the compound wherein the partial structure (b) containing ring A is a group represented by the formula (i) (compound I-11').

As the compound of the present invention, preferred are the compounds of the below-mentioned Examples, more preferred are Examples 1, 2, 3, 4, 5 and 8, further more preferred are the compounds of Examples 1, 3 and 4.

As the compound of the present invention, the compounds of Examples 10, 11, 13, 15-24, 27, 29, 30, 33, 34, 37, 40 to 43, 45, 46, 49 and 51 are also preferable, and particularly preferred are the compounds of Examples 16, 18, 21, 23, 30 and 34.

When the compound of the present invention can form a salt, the salt only needs to be pharmaceutically acceptable. For example, when an acidic group such as a carboxyl group and the like is present in the formula, ammonium salt, salts with alkali metal such as sodium, potassium and the like, salts with alkaline earth metal such as calcium, magnesium and the like, aluminum salt, zinc salt, salts with organic amine such as triethylamine, ethanolamine, morpholine, piperidine, dicyclohexylamine and the like, and salts with basic amino acid such as arginine, lysine and the like can be mentioned with regard to the acidic group. When a basic group is present in the formula, salts with inorganic acid such as hydrochloric acid, sulfuric acid, phosphoric acid, nitric acid, hydrobromic acid and the like, salts with organic carboxylic acid such as acetic acid, trifluoroacetic acid, citric acid, benzoic acid, maleic acid, fumaric acid, tartaric acid, succinic acid, tannic acid, butyric acid, phthalein acid, pamoic acid, enanthic acid, decanoic acid, 8-chlorotheophylline, salicylic acid, lactic acid, oxalic acid, mandelic acid, malic acid and the like, and salts with organic sulfonic acid such as methanesulfonic acid, benzenesulfonic acid, p-toluenesulfonic acid and the like can be mentioned with regard to the basic group. As a method forming a salt, the compound of the present invention and necessary acid or base are mixed at a suitable quantitative ratio in a solvent or a dispersing agent, or cation exchange or anion exchange of other salt form is employed.

The compound of the present invention also encompasses optical isomers, stereoisomers, tautomers, rotamers, and mixtures thereof at optional ratios. These can be obtained each as a single product according to a synthesis method and separation method known per se. For example, an optical isomer can be obtained by using an optically active synthetic intermediate or by optically resolving a racemate of a synthetic intermediate or final product by a conventional method.

Furthermore, it also encompasses a stable isotope and a radioactive isotope.

The compound of the present invention also includes solvates of the compound such as hydrate, alcohol adduct and the like.

The compound of the present invention can also be converted to a prodrug. The prodrug in the present invention is a compound that is converted in the body to produce the compound of the present invention. For example, when the active component contains a carboxyl group or a phosphate group, an ester, amide and the like thereof can be mentioned. When the active component contains an amino group, an amide, carbamate and the like thereof can be mentioned. When the active component contains a hydroxy group, an ester, carbonate, carbamate and the like thereof can be mentioned. When the compound of the present invention is converted to a prodrug, it may be bonded to an amino acid or saccharides.

The present invention also encompasses a metabolite of the compound of the present invention. The metabolite of the compound of present invention means a compound resulting from the conversion of the compound of the present invention by a metabolic enzyme and the like in the body. For example, a compound wherein a hydroxy group is introduced on the benzene ring of the compound of the present invention due to the metabolism, a compound wherein glucuronic acid, glucose or amino acid is bonded to the carboxylic acid moiety of the compound of the present invention or a hydroxy group added by the metabolism, and the like can be mentioned.

The compound of the present invention has a TRPA1 antagonist activity for mammals such as human, bovine, horse, dog, mouse, rat and the like, and can be used as a medicament, which is administered as it is or as a pharmaceutical composition containing the same mixed with a pharmaceutically acceptable carrier according to a method known per se. While oral administration is generally preferable, parenteral administration (e.g., routes such as intravenous, subcutaneous, intramuscular, suppository, enema, ointment, patch, sublingual, eye drop, inhalation administrations and the like) can also be employed. While the dose used for the above-mentioned objects is determined according to the desired treatment effect, administration method, duration of treatment, age, body weight and the like, a daily dose of 1 μg to 10 g for oral administration and 0.01 μg to 1 g for parenteral administration is used, which is generally administered to an adult by an oral or parenteral route in one to several portions per day or once per several days. In addition, the content of the compound of the present invention in the above-mentioned pharmaceutical composition is about 0.01 wt % to 100 wt % of the whole composition.

Examples of the pharmaceutically acceptable carrier for the pharmaceutical composition of the present invention include various organic or inorganic carrier substances conventionally used as preparation materials. For example, excipient, lubricant, binder, disintegrant, water-soluble polymer and basic inorganic salt in solid preparation; solvent, solubilizing agents, suspending agent, isotonicity agent, buffering agent and soothing agent in liquid preparation, and the like can be mentioned. Where necessary, general additives such as preservative, antioxidant, colorant, sweetening agent, souring agent, foaming agent, flavor and the like can also be used.

The dosage form of such pharmaceutical composition may be tablet, powder, pill, granule, capsule, suppository, solution, sugar-coated agent, depot, syrup, suspension, emulsion, troche, sublingual agent, adhesive preparation, oral disintegrant (tablet), inhalant, enema, ointment, patch, tape and eye drop, and these can be produced using conventional formulation auxiliaries and according to a conventional method.

The pharmaceutical composition of the present invention can be produced according to a method conventionally used in the technical field of pharmaceutical formulation, for example, the method described in the Japanese Pharmacopoeia and the like. Specific production methods of the preparation are explained in detail in the following.

For example, when the compound of the present invention is prepared as an oral preparation, excipient and, where necessary, binder, disintegrant, lubricant, colorant, flavoring agent and the like are further added and the mixture is processed to give, for example, tablet, powder, pill, granule, capsule, solution, sugar-coated agent, depot, syrup and the like according to a conventional method. Examples of the excipient include lactose, cornstarch, sucrose, glucose, sorbitol, crystalline cellulose and the like. Examples of the binder include polyvinyl alcohol, polyvinyl ether, ethylcellulose, methylcellulose, gum arabic, tragacanth, gelatin, shellac, hydroxypropylcellulose, hydroxypropylstarch, polyvinylpyrrolidone and the like. Examples of the disintegrant include starch, agar, gelatin powder, crystalline cellulose, calcium carbonate, sodium hydrogen carbonate, calcium citrate, dextran, pectin and the like. Examples of the lubricant include magnesium stearate, talc, polyethylene glycol, silica, hydrogenated vegetable oil and the like. As the colorant, one allowed to add to a pharmaceutical product is used, and as the flavoring agent, cocoa powder, menthol, aromatic acid, peppermint oil, borneol, powdered cinnamon bark and the like are used. Where necessary, these tablets and granules are applied with a coating as appropriate such as sugar coating, gelatin coating, and the like.

When an injection is to be prepared, pH adjuster, buffering agent, stabilizer, preservative and the like are added where necessary and the mixture is processed to give subcutaneous, intramuscular or intravenous injection according to a conventional method.

As mentioned above, since the compound of the present invention shows a TRPA1 antagonist activity for mammals (e.g., mouse, rat, hamster, rabbit, cat, dog, swine, bovine, sheep, horse, monkey, human etc., preferably human), it is useful as a TRPA1 antagonist. Moreover, the compound of the present invention is possibly utilizable for the prophylaxis and/or treatment of diseases involving TRPA1, and the compound of the present invention can be provided as a medicament for the prophylaxis and/or treatment of such diseases.

As the disease involving TRPA1, pain-associated diseases, digestive tract diseases, lung diseases, bladder diseases, inflammatory diseases, dermatic diseases, and neurological diseases and the like can be mentioned.

As the pain-associated disease, specifically, chronic pain, neuropathic pain, acute pain, inflammatory pain, postherpetic neuralgia, neuropathy, neuralgia, diabetic neuropathy, HIV related neuropathy, nerve injury, rheumatoid arthritis pain, osteoarthritis pain, back pain, lumbago, cancer pain, toothache, headache, migraine, carpal-tunnel syndrome, fibromyalgia syndrome, neuritis, sciatic neuralgia, pelvic hypersensitivity, pelvic pain, menstrual pain, visceral pain, pain after operation and the like can be mentioned.

As the digestive tract disease, functional gastrointestinal disorder {dysphagia, functional dyspepsia (FD), irritable bowel syndrome (IBS), functional abdominal pain syndrome}, erosive esophagitis (GERD), ulcer, inflammatory bowel disease (IBD), vomiting (cancer chemotherapy-induced vomiting), pancreatitis and the like can be mentioned.

As the lung disease, asthma, chronic obstructive pulmonary diseases (COPD), bronchoconstriction and the like can be mentioned.

As the bladder disease, overactive bladder, abnormal urination, cystitis and the like can be mentioned.

As the inflammatory disease, burn, osteoarthritis and the like can be mentioned.

As the dermatic disease, atopic dermatitis, pruritus and the like can be mentioned.

As the neurological disease, anticancer agent-induced neuropathy and the like can be mentioned.

As the disease involving TRPA1, preferably, chronic pain, neuropathic pain, acute pain, asthma, chronic obstructive pulmonary diseases, functional gastrointestinal disorder, erosive esophagitis, inflammatory bowel disease, pruritus, anticancer agent-induced neuropathy and the like can be mentioned.

The production methods of the representative compounds among the compounds of the present invention are shown below. However, the production method of the compound of the present invention is not limited thereto. Unless particularly indicated, each symbol in the formulas is as defined above.

For example, compound (I) can be synthesized as follows.

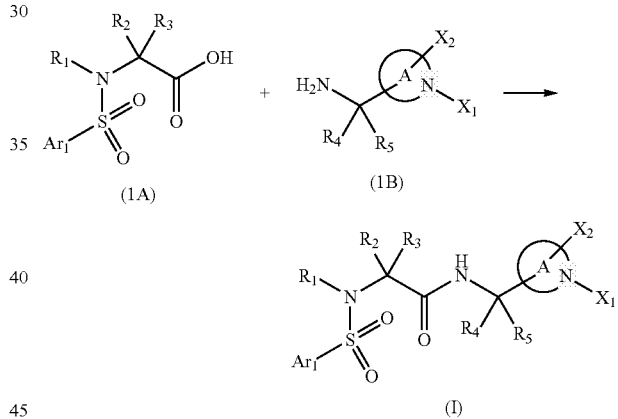

The object compound (I) can be produced by reacting carboxylic acid derivative (1A) and amine derivative (1B) in a solvent that does not adversely influence the reaction such as dichloromethane and the like in the presence or absence of 1-hydroxybenzotriazole and the like with a condensing agent represented by 1-ethyl-3-(3'-dimethylaminopropyl) carbodiimide (WSC) in the presence or absence of a base such as triethylamine and the like.

The above-mentioned carboxylic acid derivative (1A) can be synthesized as follows.

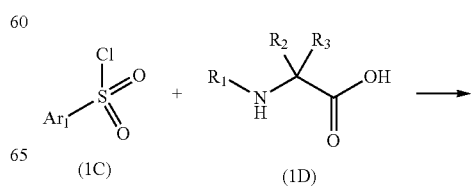

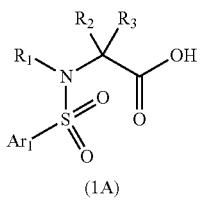

(1A)

Carboxylic acid derivative (1A) can be synthesized by reacting sulfonylchloride derivative (1C) and amine derivative (1D) in a solvent that does not adversely influence the reaction such as a mixed solvent of tetrahydrofuran and water and the like in the presence of a base such as sodium hydroxide and the like. Carboxylic acid derivative (1A) can also be synthesized by protecting carboxylic acid of amine derivative (1D) with an appropriate protecting group such as methyl, ethyl, benzyl, tert-butyl and the like where necessary, and removing the protecting group by an appropriate method such as acid treatment and the like after the above-mentioned sulfonamidation.

For example, a synthesis method of a compound represented by (1B-1), wherein, in the formula (1B), $R_4$ and $R_5$ are hydrogen; and the partial structure (b) containing ring A:

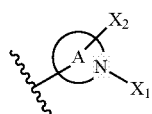

is the following formula (i):

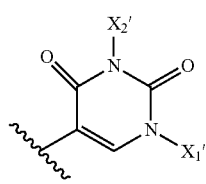

(i)

wherein $X_1'$ is -Cy and $X_2'$ is an alkyl group optionally having substituent(s) (substituents are optionally joined to form a ring), that is,

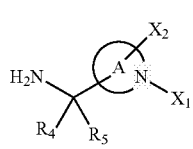

(1B)

is

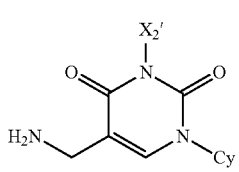

(1B-1)

wherein $X_2'$ is an alkyl group optionally having substituent(s) (substituents are optionally joined to form a ring), is shown below.

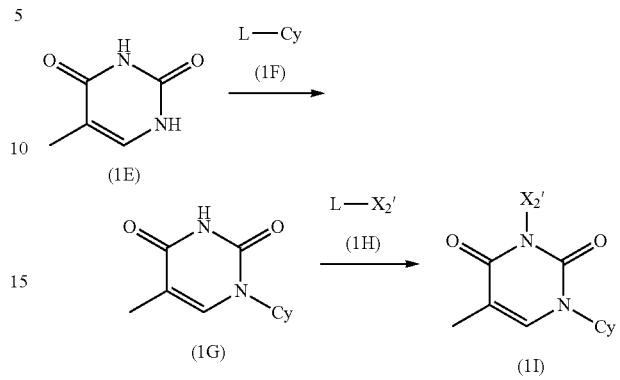

Thymine derivative (1I) can be synthesized by reacting thymine derivative (1G) obtained by reacting thymine (1E) and halogen derivative (1F) (wherein L is iodine atom, bromine atom or chlorine atom) in a solvent that does not adversely influence the reaction such as N,N-dimethylformamide and the like in the presence of a catalyst such as copper(I) iodide and the like and a ligand such as 1,8-diazabicyclo[5.4.0]-7-undecene and the like with halogen derivative (1H) (wherein L is iodine atom, bromine atom or chlorine atom) in a solvent that does not adversely influence the reaction such as N,N-dimethylformamide and the like in the presence of a base such as potassium carbonate.

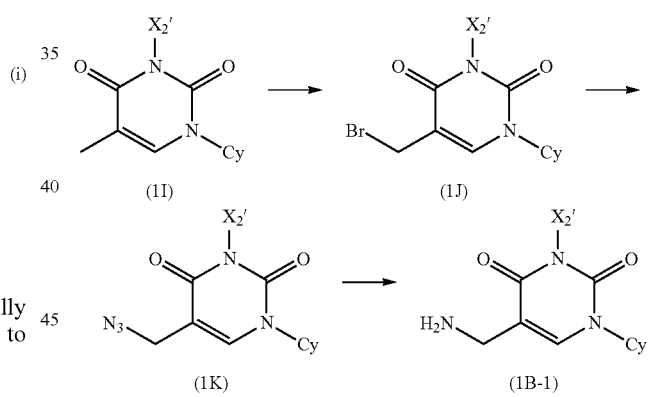

Azido derivative (1K) can be synthesized by reacting bromide derivative (1J) that can be synthesized by heating thymine derivative (1I) in a solvent that does not adversely influence the reaction such as carbon tetrachloride and the like in the presence of a brominating agent such as N-bromosuccinimide, and a radical initiator such as 2,2'-azobisisobutyronitrile with an azide agent such as sodium azide in a solvent that does not adversely influence the reaction such as N,N-dimethylformamide and the like. The object compound (1B-1) can be produced by reducing the obtained azide derivative (1K) in a solvent that does not adversely influence the reaction such as water, methanol, ethanol, tetrahydrofuran and the like in the presence of a catalyst such as palladium/carbon, palladium hydroxide, Lindlar catalyst, platinum/carbon and the like in the presence or absence of an acid such as acetic acid, hydrochloric acid and the like under a hydrogen atmosphere at normal pressure or pressurization.

In addition, amine derivative (1B-1) can also be synthesized as follows.

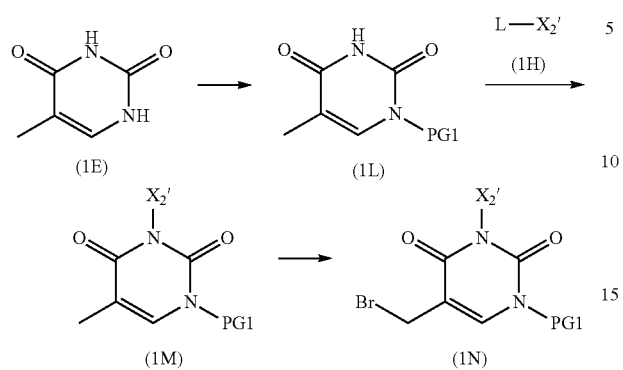

Thymine derivative (1M) can be synthesized by reacting protected thymine (1L) (wherein PG1 is a suitable protecting group such as tert-butoxycarbonyl group (Boc group), benzyloxycarbonyl group (Cbz group) and the like) obtained by protecting thymine (1E) with a suitable protecting group such as tert-butoxycarbonyl group (Boc group), benzyloxycarbonyl group (Cbz group) and the like, with halogen derivative (1H) (wherein L is iodine atom, bromine atom or chlorine atom) in a solvent that does not adversely influence the reaction such as N,N-dimethylformamide, ethanol and the like in the presence of a base such as potassium carbonate. Bromide derivative (1N) can be synthesized by heating thymine derivative (1M) in a solvent that does not adversely influence the reaction such as carbon tetrachloride and the like in the presence of a brominating agent such as N-bromosuccinimide and a radical initiator such as 2,2'-azobisisobutyronitrile.

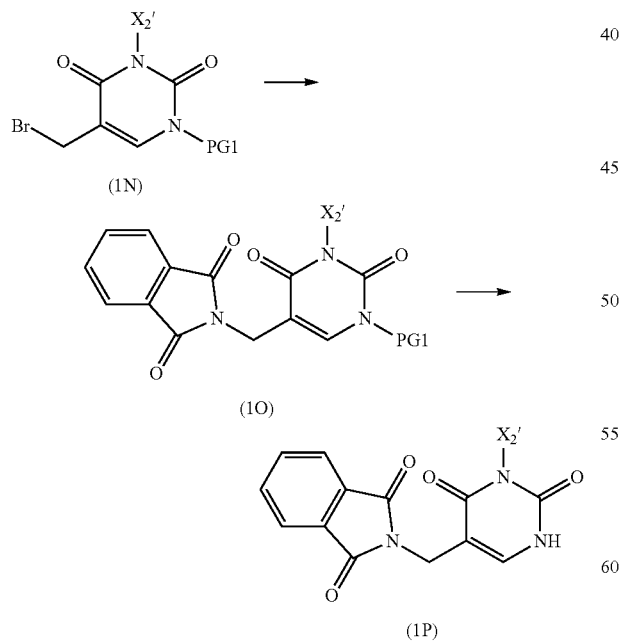

Thymine derivative (1P) can be synthesized by deprotecting the protecting group PG1 of phthalimide derivative (1O) obtained by reacting bromide derivative (1N) with phthalimide in a solvent that does not adversely influence the reaction such as N,N-dimethylformamide and the like in the presence of a base such as potassium carbonate by a suitable method such as acid treatment, hydrogenolysis and the like.

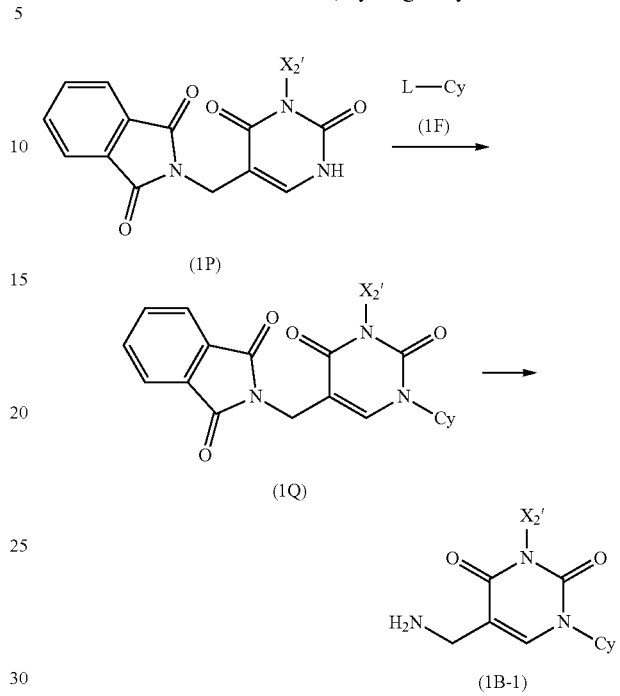

The object compound (1B-1) can be produced by reacting compound (1Q) obtained by reacting thymine derivative (1P) and halogen derivative (1P) (wherein L is iodine atom, bromine atom or chlorine atom) in a solvent that does not adversely influence the reaction such as N,N-dimethylformamide and the like in the presence of a catalyst such as copper(I) iodide and the like and a ligand such as 1,8-diazabicyclo[5.4.0]-7-undecene and the like, with hydrazine and the like in a solvent that does not adversely influence the reaction such as ethanol and the like to remove a phthaloyl group.

Amine derivative (1B-1) can also be synthesized as follows.

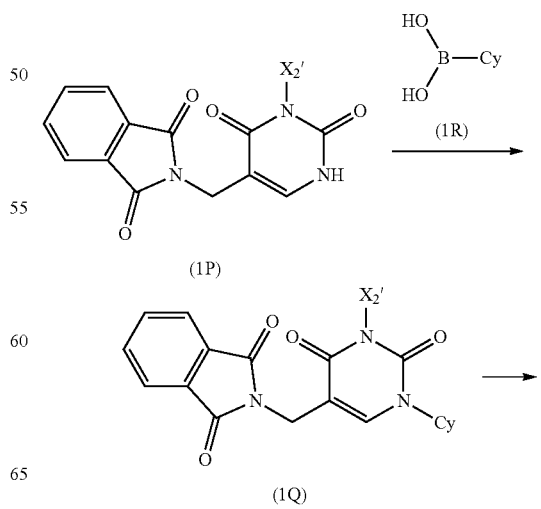

-continued

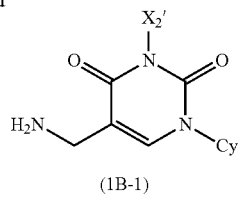

(1B-1)

The object compound (1B-1) can be produced by removing, by the aforementioned method, a phthaloyl group from compound (1Q) obtained by reacting the aforementioned thymine derivative (1P) and boronic acid derivative (1R) in a solvent that does not adversely influence the reaction such as N,N-dimethylformamide and the like in the presence of a catalyst such as copper acetate(I) and the like and a ligand such as pyridine and the like.

For example, a synthesis method of a compound represented by (1B-2), wherein, in the formula (1B), $R_4$ and $R_5$ are hydrogens; and the partial structure (b) containing ring A:

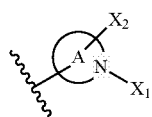

is the following formula (ii):

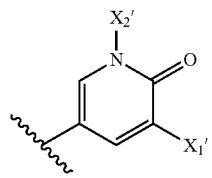

(ii)

wherein $X_1'$ is -Cy and $X_2'$ is an alkyl group optionally having substituent(s) (substituents are optionally joined to form a ring), that is,

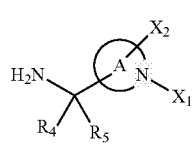

(1B)

is

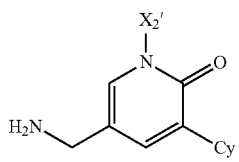

(1B-2)

wherein $X_2'$ is an alkyl group optionally having substituent(s) (substituents are optionally joined to form a ring) is shown below.

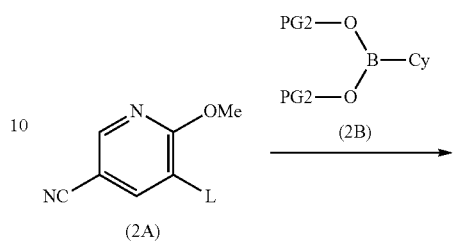

(2B)

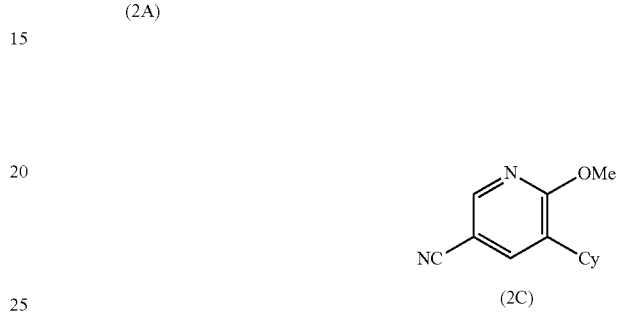

Nitrile derivative (2C) can be synthesized by reacting halogen derivative (2A) (wherein L is iodine atom, bromine atom or chlorine atom, and Me is methyl) and boronic acid derivative (2B) (wherein —B(OPG2)$_2$ is —B(OH)$_2$ or a suitable boronic acid derivative such as catecholborane, pinacolborane, N-methyliminodiacetic acid boronate and the like) in a solvent that does not adversely influence the reaction such as 1,4-dioxane or toluene, butanol and the like in the presence or absence of a cosolvent such as water and the like, in the presence or absence of a base such as sodium hydroxide, sodium carbonate, potassium carbonate, sodium hydrogen carbonate, potassium hydrogen carbonate, tripotassium phosphate and the like, and copper acetate and the like, in the presence or absence of 2,4,6-triisopropyl-2'-(dicyclohexylphosphino)biphenyl and the like, and in the presence of a catalyst such as [1,1'-bis(diphenylphosphino)ferrocene]dichloropalladium, tris(dibenzylideneacetone)dipalladium, a tetrakis(triphenylphosphine)palladium and the like.

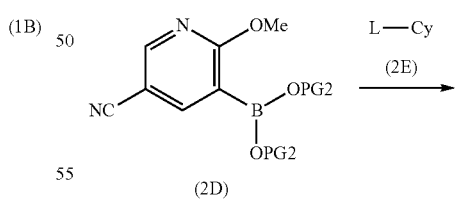
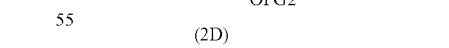

-continued

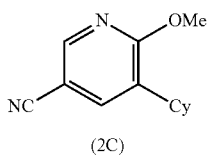
(2C)

Nitrile derivative (2C) can also be synthesized by reacting boronic acid derivative (2D) (wherein —B(OPG2)₂ is —B(OH)₂ or a suitable boronic acid derivative such as catecholborane, pinacolborane, N-methyliminodiacetic acid boronate and the like, and Me is methyl) with halogen derivative (2E) (wherein L is iodine atom, bromine atom or chlorine atom) in a solvent that does not adversely influence the reaction such as 1,4-dioxane or toluene, butanol and the like in the presence or absence of a cosolvent such as water and the like, in the presence or absence of a base such as sodium hydroxide, sodium carbonate, potassium carbonate, sodium hydrogen carbonate, potassium hydrogen carbonate, tripotassium phosphate and the like and copper acetate and the like, in the presence or absence of 2,4,6-triisopropyl-2'-(dicyclohexylphosphino)biphenyl and the like and in the presence of catalyst such as [1,1'-bis(diphenylphosphino) ferrocene]dichloropalladium, tris(dibenzylideneacetone)dipalladium, tetrakis(triphenylphosphine)palladium and the like.

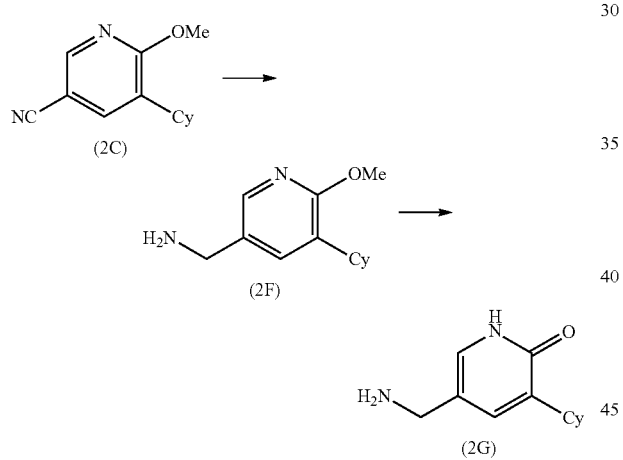

Amine derivative (2F) can be synthesized by reducing nitrile derivative (2C) in a solvent that does not adversely influence the reaction such as water, methanol, ethanol, tetrahydrofuran or acetic acid and the like in the presence of a catalyst such as palladium/carbon, palladium hydroxide, platinum/carbon and the like, in the presence or absence of an acid such as hydrochloric acid and the like under a hydrogen atmosphere at normal pressure or pressurization. Also, amine derivative (2F) can be synthesized by a reaction using lithium aluminum hydride, borane-tetrahydrofuran complex and the like in a solvent that does not adversely influence the reaction such as tetrahydrofuran and the like. In addition, amine derivative (2F) can also be synthesized by a reaction using sodium tetrahydroborate and the like in a solvent that does not adversely influence the reaction such as tetrahydrofuran and the like in the presence or absence of a cosolvent such as water and the like in the presence of a catalyst such as cobalt chloride and the like. Pyridone derivative (2G) can be synthesized by reacting amine derivative (2P) with hydrobromic acid and the like in a solvent that does not adversely influence the reaction such as acetic acid and the like.

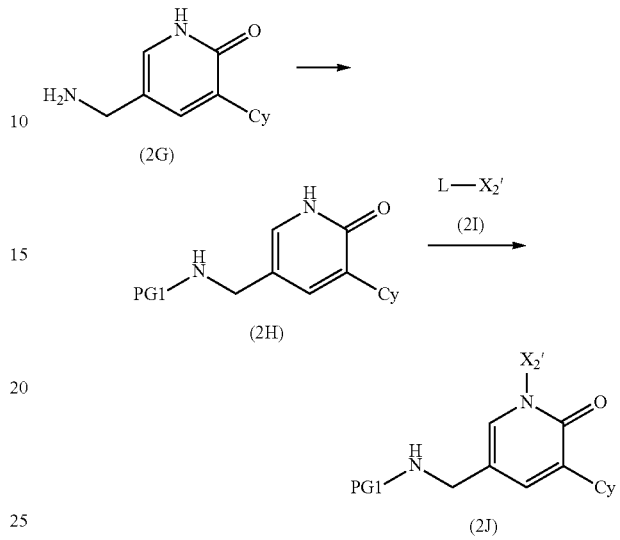

Pyridone derivative (2J) can be synthesized by reacting protected amine (2H) (wherein PG1 is a suitable protecting group such as tert-butoxycarbonyl group (Boc group), benzyloxycarbonyl group (Cbz group) and the like) obtained by protecting an amino group of pyridone derivative (2G) with a suitable protecting group such as tert-butoxycarbonyl group (Boc group), benzyloxycarbonyl group (Cbz group) and the like, with halogen derivative (2I) (wherein L is iodine atom, bromine atom or chlorine atom) in a solvent that does not adversely influence the reaction such as N,N-dimethylformamide, tetrahydrofuran and the like in the presence of a base such as potassium carbonate and cesium carbonate.

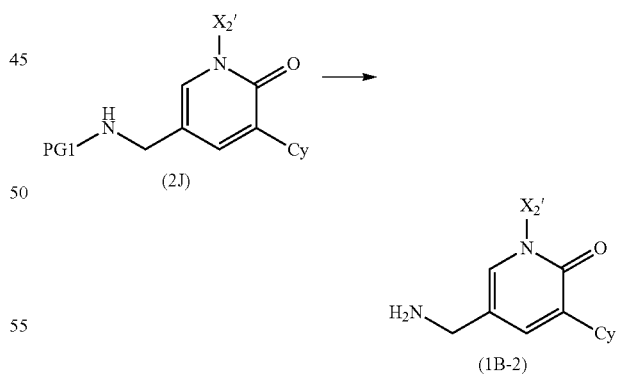

The object compound (1B-2) can be produced by deprotecting protecting group PG1 of pyridone derivative (2J) by a suitable method such as acid treatment, hydrogenolysis and the like.

For example, a synthesis method of a compound represented by (1B-3), wherein, in the formula (1B), $R_4$ and $R_5$ are hydrogens; and the partial structure (b) containing ring A:

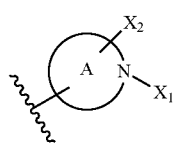

is the following formula (iii):

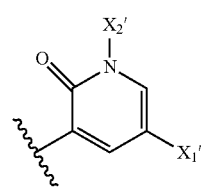

wherein $X_1'$ is -Cy and $X_2'$ is an alkyl group optionally having substituent(s) (substituents are optionally joined to form a ring), that is,

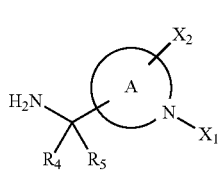

is

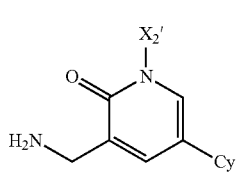

wherein $X_2'$ is an alkyl group optionally having substituent(s) (substituents are optionally joined to form a ring) is shown below.

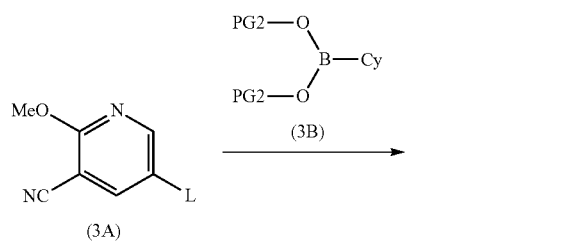

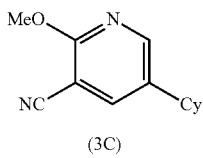

Nitrile derivative (3C) can be synthesized by reacting halogen derivative (3A) (wherein L is iodine atom, bromine atom or chlorine atom, and Me is methyl) with boronic acid derivative (3B) (wherein $-B(OPG2)_2$ is $-B(OH)_2$ or a suitable boronic acid derivative such as catecholborane, pinacolborane, N-methyliminodiacetic acid boronate and the like) in a solvent that does not adversely influence the reaction such as 1,4-dioxane or toluene, butanol and the like in the presence or absence of a cosolvent such as water and the like, in the presence or absence of a base such as sodium hydroxide, sodium carbonate, potassium carbonate, sodium hydrogen carbonate, potassium hydrogen carbonate, tripotassium phosphate and the like, and copper acetate and the like, in the presence or absence of 2,4,6-triisopropyl-2'-(dicyclohexylphosphino)biphenyl and the like, and in the presence of a catalyst such as [1,1'-bis(diphenylphosphino)ferrocene]dichloropalladium, tris(dibenzylideneacetone)dipalladium. tetrakis(triphenylphosphine)palladium and the like.

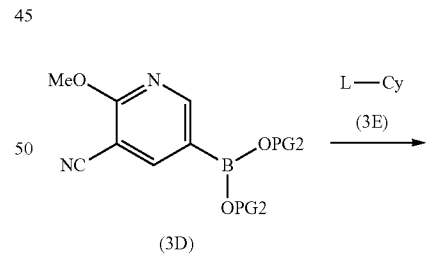

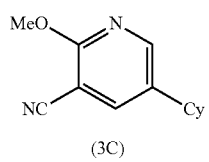

In addition, nitrile derivative (3C) can be synthesized by reacting boronic acid derivative (3D) (wherein $-B(OPG2)_2$ is $-B(OH)_2$ or a suitable boronic acid derivative such as catecholborane, pinacolborane, N-methyliminodiacetic acid boronate and the like, and Me is methyl) with halogen derivative (3E) (wherein L is iodine atom, bromine atom or chlorine atom) in a solvent that does not adversely influence the reaction such as 1,4-dioxane or toluene, butanol and the like in the presence or absence of a cosolvent such as water and the like, in the presence or absence of a base such as sodium hydroxide, sodium carbonate, potassium carbonate, sodium hydrogen carbonate, potassium hydrogen carbonate, tripotassium phosphate and the like, and copper acetate and the like, in the presence or absence of 2,4,6-triisopropyl-2'-(dicyclohexylphosphino)biphenyl and the like, and in the presence of a catalyst such as [1,1'-bis(diphenylphosphino) ferrocene]dichloropalladium, tris(dibenzylideneacetone)dipalladium, tetrakis(triphenylphosphine)palladium and the like.

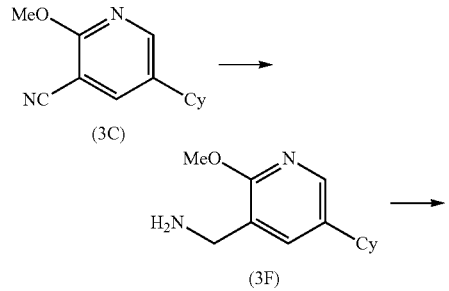

Amine derivative (3F) can be synthesized by reducing nitrile derivative (3C) in a solvent that does not adversely influence the reaction such as water, methanol, ethanol, tetrahydrofuran or acetic acid and the like, in the presence of a catalyst such as palladium/carbon, palladium hydroxide, platinum/carbon and the like, in the presence or absence of an acid such as hydrochloric acid and the like, under a hydrogen atmosphere at normal pressure or pressurization. Also, amine derivative (3P) can be synthesized by a reaction using lithium aluminum hydride, borane-tetrahydrofuran complex and the like in a solvent that does not adversely influence the reaction such as tetrahydrofuran and the like. In addition, amine derivative (3F) can also be synthesized by a reaction using sodium tetrahydroborate and the like in a solvent that does not adversely influence the reaction such as tetrahydrofuran and the like in the presence or absence of a cosolvent such as water and the like in the presence of a catalyst such as cobalt chloride and the like. Pyridone derivative (3G) can be synthesized by reacting amine derivative (3F) with hydrobromic acid and the like in a solvent that does not adversely influence the reaction such as acetic acid and the like.

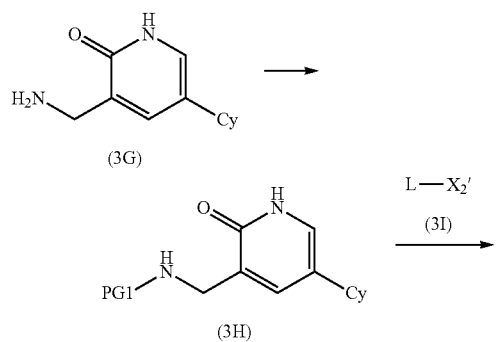

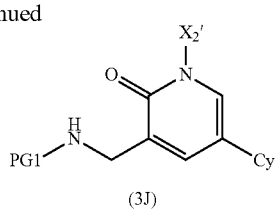

Pyridone derivative (3J) can be synthesized by reacting protected amine (3H) (wherein PG1 is a suitable protecting group such as tert-butoxycarbonyl group (Boc group), benzyloxycarbonyl group (Cbz group) and the like) obtained by protecting an amino group of pyridone derivative (3G) with a suitable protecting group such as tert-butoxycarbonyl group (Boc group), benzyloxycarbonyl group (Cbz group) and the like, with halogen derivative (3I) (wherein L is iodine atom, bromine atom or chlorine atom) in a solvent that does not adversely influence the reaction such as N,N-dimethylformamide, tetrahydrofuran and the like in the presence of a base such as potassium carbonate and cesium carbonate.

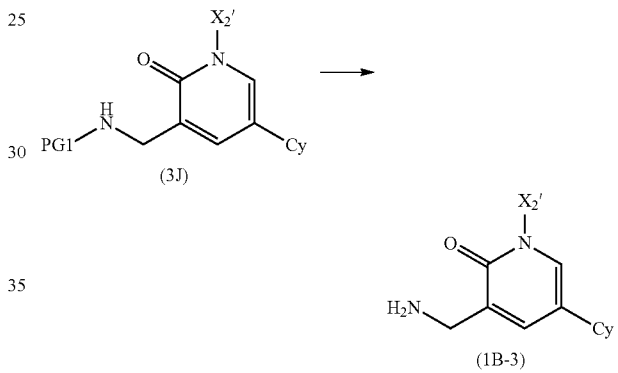

The object compound (1B-3) can be produced by deprotecting protecting group PG1 of pyridone derivative (3J) by a suitable method such as acid treatment, hydrogenolysis and the like.

For example, a synthesis method of a compound represented by (1B-5), wherein, in the formula (1B), $R_4$ and $R_5$ are hydrogens; and the partial structure (b) containing ring A:

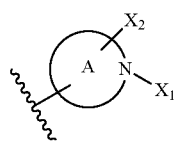

is the following formula (v):

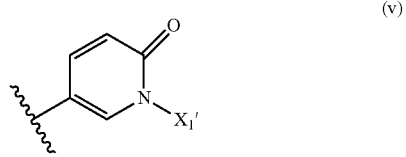

wherein $X_1{}'$ is -Cy, that is,

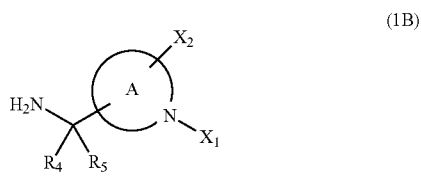
(1B)

is

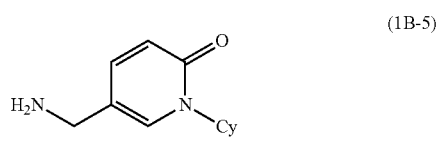
(1B-5)

is shown below.

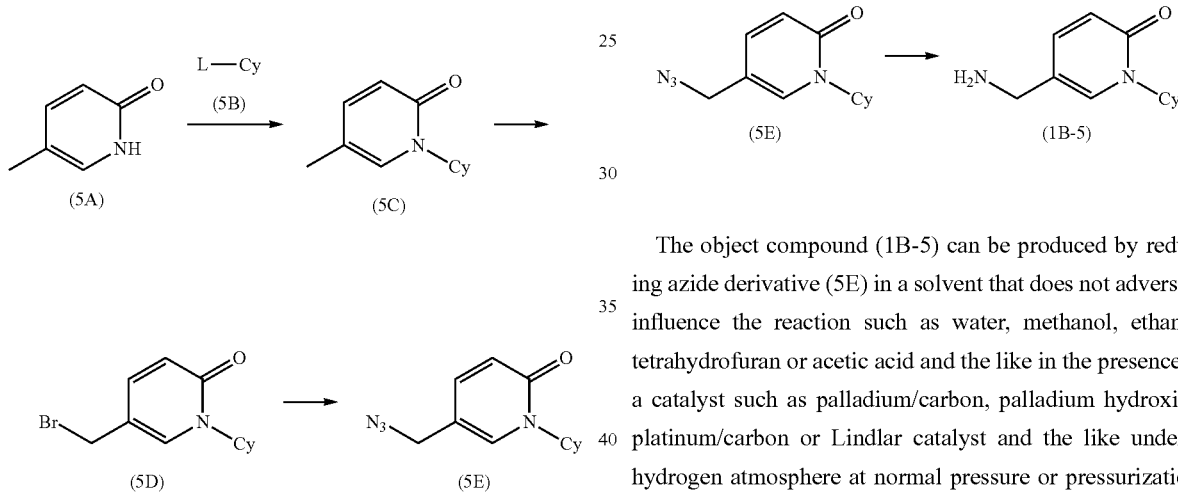

Bromide derivative (5D) can be synthesized by heating substituted pyridone derivative (5C) obtained by reacting pyridone derivative (5A) and halogen derivative (5B) (wherein L is iodine atom, bromine atom or chlorine atom) in a solvent that does not adversely influence the reaction such as N,N-dimethylformamide, 1,4-dioxane and the like in the presence or absence of a base such as potassium phosphate and the like in the presence of a catalyst such as copper(I) iodide and the like and a ligand such as 1,8-diazabicyclo[5.4.0]-7-undecene, N,N'-dimethylethylenediamine and the like, in a solvent that does not adversely influence the reaction such as carbon tetrachloride and the like with a brominating agent such as N-bromosuccinimide in the presence of a radical initiator such as 2,2'-azobisisobutyronitrile. Azide derivative (5B) can be synthesized by reacting bromide derivative (5D) with an azide agent such as sodium azide and the like in a solvent that does not adversely influence the reaction such as N,N-dimethylformamide, tetrahydrofuran and the like.

The object compound (1B-5) can be produced by reducing azide derivative (5E) in a solvent that does not adversely influence the reaction such as water, methanol, ethanol, tetrahydrofuran or acetic acid and the like in the presence of a catalyst such as palladium/carbon, palladium hydroxide, platinum/carbon or Lindlar catalyst and the like under a hydrogen atmosphere at normal pressure or pressurization.

Other features of the invention will become apparent in the course of the following descriptions of exemplary embodiments which are given for illustration of the invention and are not intended to be limiting thereof.

EXAMPLES

The present invention is explained in detail in the following by referring to Reference Examples, Examples and Experimental Examples, which are not to be construed as limitative. Unless particularly indicated, the apparatuses, reagents and the like to be used in the Examples can be easily prepared according to a method generally practiced in the pertinent field or are commercially available. In addition, % in the title compound means the yield.

The structural formulas and property values of the Reference Example compounds are shown in Table 2.

TABLE 2
| Ref. Ex. No. | Structural Formula | MS(ESI) m/z (M + H)+ | NMR |
|---|---|---|---|
| A-1 | 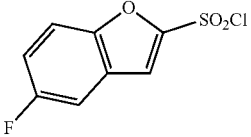 [SMILES: O=S(=O)(Cl)c1cc2cc(F)ccc2o1] | 235 | $^1$H NMR (400 MHz, CD$_3$OD) δ 7.67-7.63 (m, 2H), 7.47-7.34 (m, 2H). |
| B-1 | 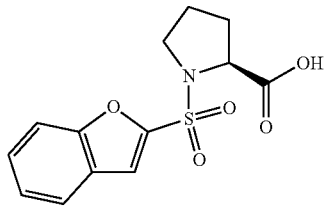 [SMILES: O=C(O)[C@@H]1CCCN1S(=O)(=O)c1cc2ccccc2o1] | 296 | $^1$H NMR (400 MHz, DMSO-d$_6$) δ 12.91 (s, 1H), 7.82 (d, J = 8.0 Hz, 1H), 7.75 (d, J = 8.0 Hz, 1H), 7.67 (s, 1H), 7.56-7.52 (m, 1H), 7.42-7.37 (m, 1H), 4.29-4.26 (m, 1H), 3.54-3.47 (m, 1H), 3.41-3.35 (m, 1H), 2.10-1.82 (m, 3H), 1.73-1.64 (m, 1H). |
| B-2 | 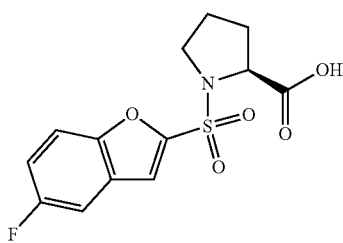 [SMILES: O=C(O)[C@@H]1CCCN1S(=O)(=O)c1cc2cc(F)ccc2o1] | 314 | $^1$H NMR (300 MHz, CD$_3$OD) δ 7.68-7.65 (m, 1H), 7.52-7.50 (m, 2H), 7.33-7.28 (m, 1H), 4.45-4.42 (m, 1H), 3.67-3.64 (m, 1H), 3.55-3.51 (m, 1H), 2.18-2.05 (m, 3H), 1.84-1.81 (m, 1H). |
| B-3 | 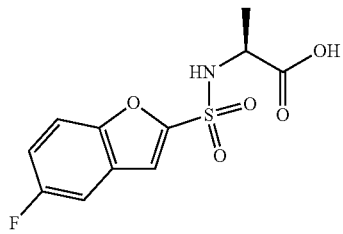 [SMILES: C[C@H](NS(=O)(=O)c1cc2cc(F)ccc2o1)C(=O)O] | 288 | $^1$H NMR (400 MHz, DMSO-d$_6$) δ 12.75 (br-s, 1H), 8.91 (d, J = 8.7 Hz, 1H), 7.75 (dd, J = 9.1, 4.1 Hz, 1H), 7.60 (dd, J = 8.5, 2.8 Hz, 1H), 7.49 (s, 1H), 7.36 (ddd, J = 9.3, 9.3, 2.8 Hz, 1H), 3.96 (dq, J = 8.9, 7.2 Hz, 1H), 1.26 (d, J = 7.2 Hz, 3H). |
| B-4 | 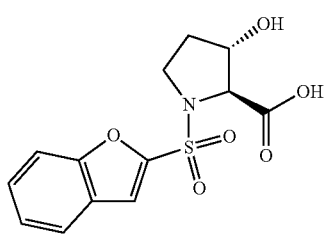 [SMILES: O=C(O)[C@@H]1[C@@H](O)CCN1S(=O)(=O)c1cc2ccccc2o1] | 312 | — |
| B-5 | 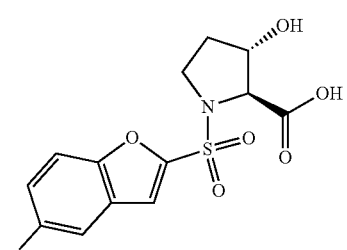 | 330 | $^1$H NMR (300 MHz, CD$_3$OD) δ 7.65-7.61 (m, 1H), 7.50-7.45 (m, 2H), 7.28 (dt, J = 9.0, 2.7 Hz, 1H), 4.38 (s, 1H), 4.28 (s, 1H), 3.75-3.56 (m, 2H), 2.15-2.05 (m, 1H), 1.90-1.84 (m, 1H). |

TABLE 2-continued
| Ref. Ex. No. | Structural Formula | MS(ESI) m/z (M + H)+ | NMR |
|---|---|---|---|
| C-1 | 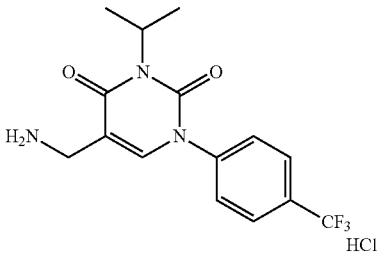 [SMILES: CC(C)n1c(=O)c(CN)cn(-c2ccc(C(F)(F)F)cc2)c1=O ; Cl] | 328 | $^1$H NMR (300 MHz, DMSO-$d_6$) δ 8.27 (s, 3H), 8.16 (s, 1H), 7.95-7.93 (m, 2H), 7.75-7.72 (m, 2H), 5.17-5.08 (m, 1H), 3.74 (s, 2H), 1.43 (t, J = 7.0 Hz, 6H). |
| C-2 | 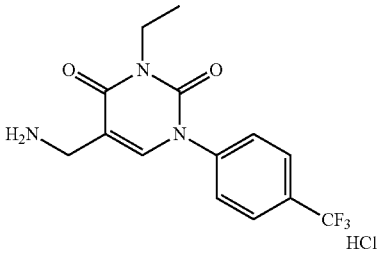 [SMILES: CCn1c(=O)c(CN)cn(-c2ccc(C(F)(F)F)cc2)c1=O ; Cl] | 314 | $^1$H NMR (300 MHz, DMSO-$d_6$) δ 8.27 (s, 3H), 8.19 (s, 1H), 7.97-7.94 (m, 2H), 7.76-7.73 (m, 2H), 3.96-3.59 (m, 2H), 3.76 (s, 2H), 1.17 (t, J = 6.9 Hz, 3H). |
| C-3 | 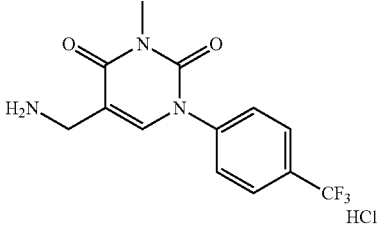 [SMILES: Cn1c(=O)c(CN)cn(-c2ccc(C(F)(F)F)cc2)c1=O ; Cl] | 300 | $^1$H NMR (300 MHz, CD$_3$OD) δ 7.97 (s, 1H), 7.88-7.86 (m, 2H), 7.68-7.66 (m, 2H), 3.91 (s, 2H), 3.40 (s, 3H). |
| A-2 | 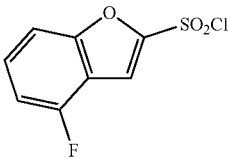 [SMILES: O=S(=O)(Cl)c1cc2c(F)cccc2o1] | 236 | $^1$H NMR (400 MHz, CDCl$_3$) δ 7.72 (s, 1H), 7.60-7.55 (m, 1H), 7.47 (d, J = 8.8 Hz, 1H), 7.12 (t, J = 8.8 Hz, 1H). |
| A-3 | 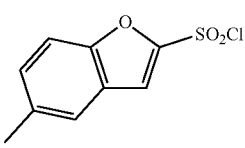 | 231 | — |
| A-4 | 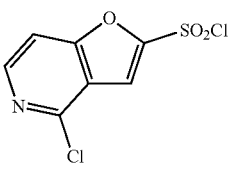 [SMILES: O=S(=O)(Cl)c1cc2c(Cl)nccc2o1] | 252 | $^1$H NMR (400 MHz, CDCl$_3$) δ 8.55 (d, J = 6.0 Hz, 1H), 7.74 (d, J = 1.0 Hz, 1H), 7.59 (dd, J = 6.0, 1.0 Hz, 1H). |
| B-6 | 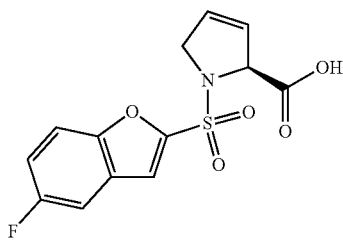 [SMILES: O=C(O)[C@@H]1C=CCN1S(=O)(=O)c1cc2cc(F)ccc2o1] | 312 | $^1$H NMR (300 MHz, CD$_3$OD) δ 7.63 (dd, J = 9.3, 3.9 Hz, 1H), 7.54 (s, 1H), 7.49 (dd, J = 8.1, 2.7 Hz, 1H), 7.29 (ddd, J = 9.3, 9.0, 2.7 Hz, 1H), 5.98-5.96 (m, 1H), 5.82-5.78 (m, 1H), 5.20-5.18 (m, 1H), 4.37-4.35 (m, 2H). |

TABLE 2-continued

| Ref. Ex. No. | Structural Formula | MS(ESI) m/z (M + H)+ | NMR |
|---|---|---|---|
| B-7 | | 350 | $^1$H NMR (300 MHz, CD$_3$OD) δ 7.66-7.62 (m, 1H), 7.55 (d, J = 1.2 Hz, 1H), 7.49 (dd, J = 8.4, 2.7 Hz, 1H), 7.29 (dt, J = 9.0, 2.7 Hz, 1H), 4.70-4.64 (m, 1H), 3.98-3.90 (m, 2H), 2.83-2.71 (m, 1H), 2.59-2.49 (m, 1H). |
| B-8 | | 300 | $^1$H NMR (300 MHz, CD$_3$OD) δ 7.71 (dd, J = 9.2, 4.1 Hz, 1H), 7.61 (s, 1H), 7.54 (dd, J = 8.4, 2.7 Hz, 1H), 7.34 (ddd, J = 9.3, 9.0, 2.7 Hz, 1H), 4.76 (t, J = 8.4 Hz, 1H), 4.03-3.96 (m, 2H), 2.45-2.36 (m, 2H). |
| B-9 | | 300 | — |
| B-10 | | 314 | $^1$H NMR (400 MHz, CD$_3$OD) δ 7.59-7.50 (m, 3H), 7.16-7.12 (m, 1H), 4.47-4.44 (m, 1H), 3.69-3.64 (m, 1H), 3.56-3.52 (m, 1H), 2.20-2.00 (m, 3H), 1.85-1.81 (m, 1H). |
| B-11 | | 297 | $^1$H NMR (400 MHz, DMSO-d$_6$) δ 12.92 (s, 1H), 9.12 (s, 1H), 8.66 (d, J = 7.4 Hz, 1H), 7.87 (d, J = 7.4 Hz, 1H), 7.82 (s, 1H), 4.31-4.28 (m, 1H), 3.57-3.52 (m, 1H), 3.44-3.38 (m, 1H), 2.14-2.09 (m, 1H), 1.96-1.84 (m, 2H), 1.76-1.72 (m, 1H). |
| B-12 | | 310 | $^1$H NMR (400 MHz, CD$_3$OD) δ 7.56 (s, 1H), 7.52-7.49 (m, 1H), 7.44 (d, J = 0.8 Hz, 1H), 7.35 (dd, J = 11.2, 1.6 Hz, 1H), 4.43-4.38 (m, 1H), 3.64-3.60 (m, 1H), 3.58-3.31 (m, 1H), 2.46 (s, 3H), 2.18-1.82 (m, 3H), 1.72-1.71 (m, 1H). |

TABLE 2-continued

| Ref. Ex. No. | Structural Formula | MS(ESI) m/z (M + H)+ | NMR |
|---|---|---|---|
| B-13 | | 283 | ¹H NMR (400 MHz, DMSO-d₆) δ 12.56 (s, 1H), 9.38 (s, 1H), 9.06 (s, 1H), 8.62 (d, J = 5.6 Hz, 1H), 7.81 (d, J = 5.6 Hz, 1H), 7.64 (s, 1H), 1.35-1.31 (m, 2H), 1.29-1.24 (m, 2H). |
| B-14 | | 312 | — |
| B-15 | | 296 | ¹H NMR (400 MHz, DMSO) δ 7.64 (d, J = 4.1 Hz, 1H), 7.34 (d, J = 4.1 Hz, 1H), 4.11 (dd, J = 8.7, 4.1 Hz, 1H), 3.47-3.38 (m, 1H), 3.28-3.19 (m, 1H), 2.08-1.94 (m, 1H), 1.94-1.78 (m, 2H), 1.74-1.62 (m, 1H). |
| B-16 | | 274 | — |
| C-4 | | 311 | ¹H NMR (400 MHz, CD₃OD) δ 8.13 (d, J = 2.4 Hz, 1H), 8.05 (d, J = 2.4 Hz, 1H), 7.74-7.80 (m, 4H), 5.29 (hept, J = 6.9 Hz, 1H), 4.10 (s, 2H), 1.49 (d, J = 6.9 Hz, 6H). |
| C-5 | | 311 | ¹H NMR (400 MHz, DMSO-d₆) δ 8.41 (brs, 3H), 8.07 (d, J = 2.4 Hz, 1H), 7.98 (d, J = 8.2 Hz, 2H), 7.96 (d, J = 2.4 Hz, 1H), 7.78 (d, J = 8.2 Hz, 2H), 5.17 (hept, J = 6.8 Hz, 1H), 3.88-3.96 (m, 2H), 1.35 (d, J = 6.8 Hz, 6H). |
| C-6 | | 269 | ¹H NMR (400 MHz, CD₃OD) δ7.90-7.86 (m, 3H), 7.74 (d, J = 9.4 Hz, 1H), 7.67 (d, J = 8.0 Hz, 2H), 6.72 (d, J = 9.4 Hz, 1H), 4.90 (s, 2H). |

TABLE 2-continued

| Ref. Ex. No. | Structural Formula | MS(ESI) m/z (M + H)+ | NMR |
|---|---|---|---|
| C-7 | (isopropyl-substituted uracil with aminomethyl, N-linked to 6-CF3-pyridin-3-yl) | 329 | — |
| C-8 | (isopropyl-substituted uracil with aminomethyl, N-linked to 5-CF3-pyridin-2-yl) | 329 | — |
| C-9 | (isopropyl-substituted uracil with aminomethyl, N-linked to 4-fluorophenyl) | 278 | — |
| C-10 | (isopropyl-substituted uracil with aminomethyl, N-linked to 4-chlorophenyl) | 294 | — |
| C-11 | (N-isopropyl pyridinone with aminomethyl, coupled to 6-CF3-pyridin-3-yl) HCl | 312 | — |
| C-12 | (N-isopropyl pyridinone with aminomethyl, coupled to 5-CF3-pyridin-2-yl) HCl | 312 | — |

TABLE 2-continued

| Ref. Ex. No. | Structural Formula | MS(ESI) m/z (M + H)+ | NMR |
|---|---|---|---|
| C-13 | [structure: 1-isopropyl-5-(aminomethyl)-3-(6-(trifluoromethyl)pyridin-3-yl)pyridin-2(1H)-one · HCl] | 312 | — |
| C-14 | [structure: 1-isopropyl-5-(aminomethyl)-3-(5-(trifluoromethyl)pyridin-2-yl)pyridin-2(1H)-one · HCl] | 312 | — |

Reference Example A-1

Synthesis of 5-fluorobenzofuran-2-ylsulfonylchloride (A-1)

(Step 1) Synthesis of 2-(2,2-dibromovinyl)-4-fluorophenol

A solution of carbon tetrabromide (1.70 kg, 5.14 mol) in dichloromethane (80 mL) was cooled to 0° C., triphenylphosphine (2.07 kg, 7.91 mol) was added and the mixture was stirred for 30 min. To the reaction mixture was added triethylamine (1.30 kg, 12.8 mol), and 5-fluoro-2-hydroxybenzaldehyde (300 g, 2.14 mol) was slowly added while maintaining the reaction temperature to 5° C. or below. The reaction mixture was stirred at 30° C. for 2 hr and concentrated under reduced pressure, and the obtained residue was purified by silica gel column chromatography (hexane/ethyl acetate) to give the title compound (300 g, 1.01 mol, 47%).
$^1$H NMR (400 MHz, CDCl$_3$) δ 7.54 (s, 1H), 7.35-7.32 (m, 1H), 6.95-6.90 (m, 1H), 6.79-6.75 (m, 1H), 5.41 (s, 1H).

(Step 2) Synthesis of 2-bromo-5-fluorobenzofuran

To the compound (300 g, 1.01 mol) obtained in step 1, copper(I) iodide (15.5 g, 81 mmol) and potassium phosphate (430 g, 2.03 mol) was added tetrahydrofuran (2 L) and the mixture was stirred at 80° C. for 2 hr. The insoluble material was filtered off, and the filtrate was concentrated under reduced pressure. The obtained residue was purified by silica gel column chromatography (hexane) to give the title compound (120 g, 0.56 mol, 55%).
$^1$H NMR (300 MHz, CDCl$_3$) δ 7.41-7.37 (m, 1H), 7.20-7.17 (m, 1H), 7.03-6.96 (m, 1H), 6.71 (s, 1H).

(Step 3) Synthesis of 5-fluorobenzofuran-2-ylsulfonylchloride (A-1)

To the compound (80 g, 0.37 mol) obtained in step 2 was added diethylether (2 L), and the mixture was cooled to 0° C. 1.3 mol/L tert-Butyllithium (n-pentane solution, 375 mL, 0.49 mol) was slowly added dropwise while maintaining the reaction temperature to 5° C. or below. After stirring at 0° C. for 30 min, sulfur dioxide was blown into the reaction mixture for 25 min while maintaining the reaction temperature to 5° C. or below. N-chlorosuccinimide (65 g, 0.49 mol) was added at 0° C. and the mixture was stirred for 20 min. The reaction mixture was poured into ice water, and extracted with dichloromethane. The organic layer was dried over sodium sulfate. The desiccant was filtered off, the solvent was evaporated and the obtained residue was purified by silica gel column chromatography (hexane) to give the title compound (28 g, 0.12 mol, 32%).
MS (ESI) m/z 235 (M+H)+
$^1$H NMR (400 MHz, CD$_3$OD) δ 7.67-7.63 (m, 2H), 7.47-7.34 (m, 2H).

Reference Example A-2

Synthesis of 4-fluorobenzofuran-2-ylsulfonylchloride (A-2)

The title compound was obtained using 6-fluoro-2-hydroxybenzaldehyde instead of 5-fluoro-2-hydroxybenzaldehyde and by an operation similar to that in Reference Example A-1.
MS (ESI) m/z 235 (M+H)+
$^1$H NMR (400 MHz, CDCl$_3$) δ 7.72 (s, 1H), 7.60-7.55 (m, 1H), 7.47 (d, J=8.8 Hz, 1H), 7.12 (t, J=8.8 Hz, 1H).

Reference Example A-3

Synthesis of 5-methylbenzofuran-2-ylsulfonylchloride (A-3)

A solution of 5-methylbenzofuran (5.2 g, 39 mmol) in tetrahydrofuran (75 mL) was cooled to −40° C., 2.5 mol/L n-butyllithium (hexane solution, 19 mL, 48 mmol) was added and the mixture was stirred for 40 min. Sulfur dioxide was blown into the reaction mixture for 20 min while maintaining the temperature at −40° C. to −30° C., and the mixture was stirred at room temperature for 90 min. To the reaction mixture was added hexane, and the insoluble material was collected by filtration, and dried. To the obtained solid were added dichloromethane (300 mL) and N-chlorosuccinimide (31 g, 0.23 mol), and the mixture was stirred at room temperature overnight, and the insoluble material was filtered off. The filtrate was concentrated under reduced pressure to give the title compound (3.0 g, 13 mmol, 33%).
MS (ESI) m/z 231 (M+H)$^+$ Reference Example A-4

Synthesis of 4-chlorofuro[3,2-c]pyridine-2-sulfonylchloride (A-4)

A solution of 4-chlorofuro[3,2-c]pyridine (3.0 g, 20 mmol) in tetrahydrofuran (80 mL) was cooled to −40° C., 2.5 mol/L n-butyllithium (hexane solution, 9.4 mL, 24 mmol) was added and the mixture was stirred for 1 hr. Sulfur dioxide was blown into the reaction mixture for 30 min while maintaining the temperature at −40° C. to −30° C., and the mixture was stirred at room temperature for 1.5 hr. To the reaction mixture was added hexane (100 mL), and the insoluble material was collected by filtration, and dried. To the obtained solid was added dichloromethane (75 mL) and N-chlorosuccinimide (3.1 g, 23 mmol) was added at 0° C., and the mixture was stirred at room temperature for 1 hr. The reaction mixture was washed 5 times with water. The organic layer was dried over sodium sulfate, the desiccant was filtered off, and the solvent was evaporated to give the title compound (3.5 g, 14 mmol, 71%).
MS (ESI) m/z 252 (M+H)$^+$
$^1$H NMR (400 MHz, CDCl$_3$) δ 8.55 (d, J=6.0 Hz, 1H), 7.74 (d, J=1.0 Hz, 1H), 7.59 (dd, J=6.0, 1.0 Hz, 1H).

Reference Example B-1

Synthesis of (2S)-1-(benzofuran-2-ylsulfonyl)pyrrolidine-2-carboxylic acid (B-1)

L-proline (53 mg, 0.46 mmol) was dissolved in 2 mol/L aqueous sodium hydroxide solution (2 mL) and tetrahydrofuran (2 mL), benzofuran-2-sulfonylchloride (120 mg, 0.56 mmol) was added and the mixture was stirred at room temperature for a few hours. The reaction mixture was extracted with dichloromethane, and the aqueous layer was neutralized with 2 mol/L hydrochloric acid, and extracted with dichloromethane. The obtained organic layer was dried over sodium sulfate. The desiccant was filtered off, and the solvent was evaporated to give the title compound as pale yellow white crystals (110 mg, 0.37 mmol, 81%).
MS (ESI) m/z 296 (M+H)$^+$
$^1$H NMR (400 MHz, DMSO-d$_6$) δ 12.91 (s, 1H), 7.82 (d, J=8.0 Hz, 1H), 7.75 (d, J=8.0 Hz, 1H), 7.67 (s, 1H), 7.56-7.52 (m, 1H), 7.42-7.37 (m, 1H), 4.29-4.26 (m, 1H), 3.54-3.47 (m, 1H), 3.41-3.35 (m, 1H), 2.10-1.82 (m, 3H), 1.73-1.64 (m, 1H).

Reference Example B-2

Synthesis of (2S)-1-(5-fluorobenzofuran-2-yl)sulfonylpyrrolidine-2-carboxylic acid (B-2)

The title compound was obtained (yield 69%) using A-1 instead of benzofuran-2-sulfonylchloride and by an operation similar to that in Reference Example B-1.
MS (ESI) m/z 314 (M+H)$^+$
$^1$H NMR (300 MHz, CD$_3$OD) δ 7.68-7.65 (m, 1H), 7.52-7.50 (m, 2H), 7.33-7.28 (m, 1H), 4.45-4.42 (m, 1H), 3.67-3.64 (m, 1H), 3.55-3.51 (m, 1H), 2.18-2.05 (m, 3H), 1.84-1.81 (m, 1H).

Reference Example B-3

Synthesis of (2S)-2-[(5-fluorobenzofuran-2-yl)sulfonylamino]propanoic acid (B-3)

To alanine tert-butyl ester hydrochloride (0.18 g, 1.0 mmol) were added acetonitrile (5 mL), A-1 (0.28 g, 1.2 mmol) and triethylamine (0.30 mL, 2.2 mmol) and the mixture was stirred at room temperature overnight. The reaction mixture was concentrated under reduced pressure. To the obtained residue was added trifluoroacetic acid (2 mL) and the mixture was stirred at room temperature for 2 hr, concentrated under reduced pressure, and the obtained residue was purified by high performance liquid chromatography (water-acetonitrile, each containing 0.1% trifluoroacetic acid) to give the title compound (0.24 g, 0.84 mmol, 84%).
MS (ESI) m/z 288 (M+H)$^+$
$^1$H NMR (400 MHz, DMSO-d$_6$) δ 12.75 (br-s, 1H), 8.91 (d, J=8.7 Hz, 1H), 7.75 (dd, J=9.1, 4.1 Hz, 1H), 7.60 (dd, J=8.5, 2.8 Hz, 1H), 7.49 (s, 1H), 7.38 (ddd, J=9.3, 9.3, 2.8 Hz, 1H), 3.96 (dq, J=8.9, 7.2 Hz, 1H), 1.26 (d, J=7.2 Hz, 3H).

Reference Example B-4

Synthesis of (2S,3S)-1-(benzofuran-2-ylsulfonyl)-3-hydroxypyrrolidine-2-carboxylic acid (B-4)

The title compound was obtained using (3S)-3-hydroxy-L-proline instead of L-proline and by an operation similar to that in Reference Example B-1.
MS (ESI) m/z 312 (M+H)$^+$ Reference Example B-5

Synthesis of (2S,3S)-1-(5-fluorobenzofuran-2-ylsulfonyl)-3-hydroxypyrrolidine-2-carboxylic acid (B-5)

(Step 1) Synthesis of (3S)-3-hydroxy-L-proline methyl ester hydrochloride

To (3S)-3-hydroxy-L-proline (1.5 g, 12 mmol) were added methanol (20 mL) and thionyl chloride (1.4 g, 0.12 mol), and the mixture was stirred at room temperature overnight. The resulting insoluble material was collected by filtration, and washed with diethyl ether to give the title compound (1.9 g, 10 mmol, 91%).
MS (ESI) m/z 146 (M+H)$^+$
$^1$H NMR (CDCl$_3$, 300 MHz): δ 6.01-5.99 (m, 1H), 4.49-4.46 (m, 1H), 4.13 (d, J=2.7 Hz, 1H), 3.76 (s, 3H), 3.38-3.28 (m, 2H), 2.01-1.84 (m, 2H).

(Step 2) Synthesis of (2S,3S)-1-(5-fluorobenzofuran-2-ylsulfonyl)-3-hydroxypyrrolidine-2-carboxylic acid methyl ester To the compound (1.2 g, 6.7 mmol) obtained in step 1 were added dichloromethane (20 mL), triethylamine (2.8 mL, 20 mmol) and 4-dimethylaminopyridine (82 mg, 0.67 mmol). The reaction mixture was cooled to 0° C., A-1 (1.6 g, 6.7 mmol) was added and the mixture was stirred for 1 hr and concentrated under reduced pressure. The obtained residue was purified by silica gel column chromatography (petroleum ether/ethyl acetate) to give the title compound (1.4 g, 4.1 mmol, 61%).

MS (ESI) m/z 344 (M+H)$^+$

1H NMR (300 MHz, DMSO-d$_6$): δ 7.81-7.67 (m, 1H), 7.65-7.61 (m, 2H), 7.44-7.37 (m, 1H), 5.43 (s, 1H), 4.27-4.25 (n, 1H), 4.16 (s, 1H), 3.67 (s, 3H), 3.63-3.44 (m, 2H), 1.97-1.94 (m, 1H), 1.80-1.74 (m, 1H).

(Step 3) Synthesis of (2S,3S)-1-(5-fluorobenzo-furan-2-ylsulfonyl)-3-hydroxypyrrolidine-2-carboxylic acid (B-5)

To a solution of the compound (1.2 g, 3.5 mmol) obtained in step 2 in methanol (20 mL) was added 2 mol/L aqueous lithium hydroxide solution (10 mL), and the mixture was stirred at room temperature for 1 hr. Methanol was evaporated from the reaction mixture, concentrated hydrochloric acid was added and the resulting precipitate was collected by filtration, and dried to give the title compound (0.78 g, 2.4 mmol, 68%).

MS (ESI) m/z 330 (M+H)$^+$ $^1$H NMR (300 MHz, CD$_3$OD): δ 7.65-7.61 (m, 1H), 7.50-7.45 (m, 2H), 7.28 (dt, J=9.0, 2.7 Hz, 1H), 4.38 (s, 1H), 4.28 (s, 1H), 3.75-3.58 (m, 2H), 2.15-2.05 (m, 1H), 1.90-1.84 (m, 1H).

B-6, B-10, B-14-B-16 in Table 2 were synthesized by using corresponding commercially available reagents and by an operation similar to that in Reference Example B-1.

Reference Example B-7

Synthesis of (2S)-1-(5-fluorobenzofuran-2-ylsulfonyl)-4,4-difluoropyrrolidine-2-carboxylic acid (B-7)

To a solution of 4,4-difluoro-L-proline methyl ester (0.81 g, 4.9 mmol) in pyridine (20 mL) was added A-1 (1.2 g, 4.9 mmol), and the mixture was stirred at room temperature for 2 hr. To the reaction mixture was added 6 mol/L aqueous hydrochloric acid solution to adjust to pH4, and the mixture was extracted with dichloromethane. The organic layer was dried over sodium sulfate, and the desiccant was filtered off. The solvent was evaporated and the obtained residue was purified by silica gel column chromatography (hexane/ethyl acetate) to give methyl ester of the title compound. To the obtained methyl ester were added methanol (20 mL) and 2 mol/L aqueous lithium hydroxide solution (20 mL), and the mixture was stirred at room temperature for 30 min. Methanol was evaporated from the reaction mixture, concentrated hydrochloric acid was added and the resulting precipitate was collected by filtration, and dried to give the title compound (0.72 g, 2.1 mmol, 42%).

MS (ESI) m/z 350 (M+H)$^+$ $^1$H NMR (300 MHz, CD$_3$OD) δ 7.66-7.62 (m, 1H), 7.55 (d, J=1.2 Hz, 1H), 7.49 (dd, J=8.4, 2.7 Hz, 1H), 7.29 (dt, J=9.0, 2.7 Hz, 1H), 4.70-4.64 (m, 1H), 3.98-3.90 (m, 2H), 2.83-2.71 (m, 1H), 2.59-2.49 (m, 1H).

Reference Example B-8

Synthesis of (2S)-1-(5-fluorobenzofuran-2-ylsulfonyl)azetidine-2-carboxylic acid (B-8)

To (S)-azetidine-2-carboxylic acid (1.9 g, 19 mmol) were added saturated aqueous sodium hydroxide solution (15 mL) and a solution of A-1 (4.5 g, 19 mmol) in tetrahydrofuran (15 mL) and the mixture was stirred at room temperature for 30 min. Tetrahydrofuran was evaporated, adjusted to pH3-4 with 1 mol/L aqueous hydrochloric acid solution, and the precipitate was collected by filtration, and dried to give the title compound (4.0 g, 13 mmol, 71%).

MS (ESI) m/z 300 (M+H)$^+$ $^1$H NMR (300 MHz, CD$_3$OD) δ 7.71 (dd, J=9.2, 4.1 Hz, 1H), 7.61 (s, 1H), 7.54 (dd, J=8.4, 2.7 Hz, 1H), 7.34 (ddd, J=9.3, 9.0, 2.7 Hz, 1H), 4.76 (t, J=8.4 Hz, 1H), 4.03-3.96 (m, 2H), 2.45-2.36 (m, 2H).

Reference Example B-9

Synthesis of 1-[(5-fluorobenzofuran-2-yl)sulfonylamino]cyclopropanecarboxylic acid (B-9)

To a solution of 1-aminocyclopropanecarboxylic acid (0.37 g, 3.6 mmol) in tetrahydrofuran (3 mL) were added A-1 (1.0 g, 4.3 mmol) and 2 mol/L aqueous sodium hydroxide solution (3.0 mL, 6.0 mmol) and the mixture was stirred at room temperature for 4 hr. To the reaction mixture was added dichloromethane and the mixture was extracted with water. The aqueous layer was acidified with 2 mol/L hydrochloric acid, and then extracted with dichloromethane. The organic layer was concentrated under reduced pressure and the obtained residue was purified by high performance liquid chromatography (water-acetonitrile, each containing 0.1% trifluoroacetic acid) to give the title compound (0.30 g, 1.0 mmol, 28%).

MS (ESI) m/z 300 (M+H)$^+$

Reference Example B-11

Synthesis of (2S)-1-furo[3,2-c]pyridin-2-ylsulfonylpyrrolidine-2-carboxylic acid (B-11)

(Step 1) Synthesis of (2S)-1-(4-chlorofuro[3,2-c]pyridin-2-yl)sulfonylpyrrolidine-2-carboxylic acid Water (12 mL) was added to L-proline (1.0 g, 8.8 mmol) and sodium hydroxide (0.64 g, 16 mmol) to dissolve them, and the mixture was stirred at 0° C. for 25 min. A solution of A-4 (2.0 g, 8.0 mmol) in tetrahydrofuran (18 mL) was slowly added, and the mixture was stirred for 40 min. To the reaction mixture was added 6 mol/L aqueous hydrochloric acid solution to adjust to pH4, and the insoluble material was collected by filtration, and dried to give the title compound (1.1 g, 3.3 mmol, 42%) as a white solid.

MS (ESI) m/z 331 (M+H)$^+$ $^1$H NMR (400 MHz, DMSO-d$_6$) δ 8.49 (d, J=6.0 Hz, 1H), 7.93 (dd, J=6.0, 0.8 Hz, 1H), 7.80 (d, J=0.8 Hz, 1H), 4.34-4.31 (m, 1H), 3.60-3.53 (m, 1H), 3.48-3.43 (m, 1H), 2.17-2.12 (m, 1H), 1.96-1.75 (m, 3H).

(Step 2) Synthesis of (2S)-1-furo[3,2-c]pyridin-2-ylsulfonylpyrrolidine-2-carboxylic acid (B-11)

The compound (0.80 g, 2.4 mmol) obtained in step 1 was dissolved by adding acetic acid (25 mL) and tetrahydrofuran (25 mL), and 10% palladium/carbon (150 mg) was added. The reaction mixture was stirred under a hydrogen atmosphere at 70° C. for 4 hr, the catalyst was filtered off, ethyl acetate was added to the filtrate and the mixture was washed with water. The organic layer was dried over sodium sulfate, the desiccant was filtered off, and the solvent was evaporated and methanol (8 mL) was added to the obtained residue. The insoluble material was collected by filtration, and dried to give the title compound (0.30 g, 1.0 mmol, 42%) aa a white solid.

MS (ESI) m/z 297 (M+H)$^+$

1H NMR (400 MHz, DMSO-d$_6$) δ 12.92 (s, 1H), 9.12 (s, 1H), 8.66 (d, J=7.4 Hz, 1H), 7.87 (d, J=7.4 Hz, 1H), 7.82 (s, 1H), 4.31-4.28 (m, 1H), 3.57-3.52 (m, 1H), 3.44-3.38 (m, 1H), 2.14-2.09 (m, 1H), 1.96-1.84 (m, 2H), 1.76-1.72 (m, 1H).

Reference Example B-12

Synthesis of (2S)-1-(5-methyl-benzofuran-2-ylsulfonyl)pyrrolidine-2-carboxylic acid (B-12)

L-proline (0.42 g, 3.6 mmol) was dissolved in saturated aqueous sodium hydroxide solution (10 mL), and a solution of A-3 (0.91 g, 4.0 mmol) in tetrahydrofuran (5 mL) was added dropwise at 0° C. After stirring for 30 min, the reaction mixture was partitioned by adding dichloromethane. The organic layer was discarded, and the aqueous layer was concentrated under reduced pressure to remove remaining dichloromethane. The mixture was acidified by slowly adding aqueous 10 mol/L hydrochloric acid solution. The precipitate was collected by filtration and dried to give the title compound (0.78 g, 2.5 mmol, 70%).

MS (ESI) m/z 310 (M+H)$^+$ $^1$H NMR (400 MHz, CD$_3$OD):δ 7.56 (s, 1H), 7.52-7.49 (m, 1H), 7.44 (d, J=0.8 Hz, 1H), 7.35 (dd, J=11.2, 1.6 Hz, 1H), 4.43-4.39 (m, 1H), 3.64-3.60 (m, 1H), 3.58-3.31 (m, 1H), 2.46 (s, 3H), 2.18-1.82 (m, 3H), 1.72-1.71 (m, 1H).

Reference Example B-13

Synthesis of 1-(furo[3,2-c]pyridin-2-ylsulfonylamino)cyclopropanecarboxylic acid (B-13)

(Step 1) Synthesis of methyl 1-[(4-chlorofuro[3,2-c]pyridin-2-yl)sulfonylamino]cyclopropanecarboxylate To A-4 (3.4 g, 14 mmol) and methyl 1-aminocyclopropanecarboxylate (2.0 g, 13 mmol) were added dichloromethane (150 mL) and pyridine (24 mL), and the mixture was stirred at room temperature for 1.5 hr. To the reaction mixture was added water, and the organic layer was separated. The organic layer was washed with saturated brine, dried over sodium sulfate. The desiccant was filtered off, and the residue was dried under reduced pressure and the obtained residue was purified by silica gel column chromatography (petroleum ether/ethyl acetate) to give the title compound (0.50 g, 1.5 mmol, 11%).

(Step 2) Synthesis of methyl 1-(furo[3,2-c]pyridin-2-ylsulfonylamino)cyclopropanecarboxylate To the compound (0.50 g, 1.5 mmol) obtained in step 1 and 10% palladium/carbon (0.40 g) were added triethylamine (0.50 mL) and methanol (25 mL), and the mixture was stirred under a hydrogen atmosphere at 35° C. overnight. The catalyst was filtered off, and the filtrate was concentrated under reduced pressure and the obtained residue was purified by preparative TLC (dichloromethane/methanol) to give the title compound (0.16 g, 0.52 mmol, 35%).

$^1$H NMR (300 MHz, CDCl$_3$): δ 9.05 (s, 1H), 8.66 (d, J=6.0 Hz, 1H), 8.06 (d, J=6.0 Hz, 1H), 7.45 (s, 1H), 5.92 (s, 1H), 3.32 (s, 3H), 1.64-1.61 (m, 2H), 1.58-1.56 (m, 2H).

(Step 3) Synthesis of 1-(furo[3,2-c]pyridin-2-ylsulfonylamino)cyclopropanecarboxylic acid (B-13)

To a solution of the compound (0.16 g, 0.52 mmol) obtained in step 2 in tetrahydrofuran (3 mL) was added aqueous 2 mol/L lithium hydroxide solution (3 mL) and the mixture was stirred at room temperature overnight. Tetrahydrofuran was evaporated under reduced pressure at 35° C., concentrated hydrochloric acid was added to the obtained aqueous solution at 0° C. to adjust the mixture to pH4. The insoluble material was collected by filtration, and dried to give the title compound (0.12 g, 0.41 mmol, 80%).

MS (ESI) m/z 283 (M+H)$^+$ $^1$H NMR (400 MHz, DMSO-d$_6$): δ 12.56 (s, 1H), 9.38 (s, 1H), 9.06 (s, 1H), 8.62 (d, J=5.6 Hz, 1H), 7.81 (d, J=5.6 Hz, 1H), 7.64 (s, 1H), 1.35-1.31 (m, 2H), 1.29-1.24 (m, 2H).

Reference Example C-1

Synthesis of 5-(aminomethyl)-3-isopropyl-1-[4-(trifluoromethyl)phenyl]pyrimidine-2,4-dione hydrochloride (C-1)

(Step 1) Synthesis of 5-methyl-1-[4-(trifluoromethyl)phenyl]pyrimidine-2,4-dione To thymine (7.6 g, 60 mmol), 1-iodo-4-(trifluoromethyl)benzene (16 g, 60 mmol) and copper(I) iodide (3.4 g, 18 mmol) were added N,N-dimethylformamide (220 mL) and 1,8-diazabicyclo[5.4.0]-7-undecene (18 g, 0.12 mol), and the mixture was deaerated twice with nitrogen gas. After stirring at 140° C. for 8 hr, the reaction mixture was poured into water and extracted with ethyl acetate. The organic layer was washed with saturated brine, and dried over sodium sulfate. The desiccant was filtered off, and the filtrate was concentrated under reduced pressure and the obtained residue was purified by silica gel column chromatography (petroleum ether/ethyl acetate) to give the title compound (1.9 g, 7.0 mmol, 12%).

$^1$H NMR (400 MHz, DMSO-d$_6$) δ 11.53 (s, 1H), 7.89-7.86 (m, 2H), 7.70-7.67 (m, 3H), 1.82 (s, 3H).

(Step 2) Synthesis of 3-isopropyl-5-methyl-1-[4-(trifluoromethyl)phenyl]pyrimidine-2,4-dione To the compound (0.97 g, 1.6 mmol) obtained in step 1 and potassium carbonate (0.99 g, 7.2 mmol) were added N,N-dimethylformamide (25 mL) and 2-iodopropane (0.73 g, 4.3 mmol), and the mixture was stirred at 30° C. overnight. The reaction mixture was poured into water, extracted with ethyl acetate, and the organic layer was washed with saturated brine and dried over sodium sulfate. The desiccant was filtered off, and the filtrate was concentrated under reduced pressure and the obtained residue was purified by silica gel column chromatography (petroleum ether/ethyl acetate) to give the title compound (1.1 g, 3.4 mmol, 94%).

(Step 3) Synthesis of 5-(bromomethyl)-3-isopropyl-1-[4-(trifluoromethyl)phenyl]pyrimidine-2,4-dione To the compound (0.89 g, 2.8 mmol) obtained in step 2, N-bromosuccinimide (0.56 g, 3.1 mmol) and 2,2'-azobisisobutyronitrile (89 mg, 0.54 mmol) was added carbon tetrachloride (55 mL) and the mixture was stirred at 85° C. for 6 hr. The reaction mixture was concentrated under reduced pressure and the obtained residue was purified by silica gel column chromatography (petroleum ether/ethyl acetate) to give the title compound (0.25 g, 0.64 mmol, 22%).

$^1$H NMR (300 MHz, CDCl$_3$) δ 7.79-7.76 (m, 2H), 7.52-7.49 (m, 3H), 5.30-5.25 (m, 1H), 4.32 (s, 2H), 1.53 (s, 3H), 1.50 (s, 3H).

(Step 4) Synthesis of tert-butyl N-[[3-isopropyl-2,4-dioxo-1-[4-(trifluoromethyl)phenyl]pyrimidin-5-yl]methyl]carbamate To the compound (0.25 g, 0.64 mmol) obtained in step 3 and sodium azide (44 mg, 0.67 mmol) was added N,N-dimethylformamide (10 mL) and the mixture was stirred at room temperature for 1 hr. The reaction mixture was poured into water and extracted with ethyl acetate. The organic layer was washed with saturated brine, concentrated under reduced pressure and the obtained residue was dissolved in tetrahydrofuran (10 mL). di-tert-Butyl dicarbonate (0.21 g, 0.96 mol) and palladium/carbon (0.15 g) were added and the mixture was stirred under a hydrogen atmosphere at room temperature for 2 hr. The catalyst was filtered off, and the filtrate was concentrated under reduced pressure and the obtained residue was purified by silica gel column chromatography (petroleum ether/ethyl acetate) to give the title compound (0.23 g, 0.54 mmol, 84%).

$^1$H NMR (300 MHz, DMSO-d$_6$) δ 7.76-7.73 (m, 2H), 7.50-7.47 (m, 2H), 7.40 (s, 1H), 5.30-5.22 (m, 1H), 4.00 (d, J=6.6 Hz, 2H), 1.52 (s, 3H), 1.49 (s, 3H), 1.44 (s, 9H).

(Step 5) Synthesis of 5-(aminomethyl)-3-isopropyl-1-[4-(trifluoromethyl)phenyl]pyrimidine-2,4-dione hydrochloride (C-1)

The compound (0.58 g, 1.4 mmol) obtained in step 4 was dissolved in dichloromethane (5 mL), 4 mol/L hydrochloric acid (dichloromethane solution, 5 mL) was added and the mixture was stirred at room temperature for 2 hr. The reaction mixture was concentrated under reduced pressure. To the obtained residue was added diethylether (20 mL), and the mixture was stirred at room temperature for 5 min. Insoluble material was collected by filtration, washed with diethyl ether and dried to give the title compound (0.46 g, 1.3 mmol, 97%).

MS (ESI) m/z 328 (M+H)$^+$

1H NMR (300 MHz, DMSO-d$_6$) δ 8.27 (s, 3H), 8.16 (s, 1H), 7.95-7.93 (m, 2H), 7.75-7.72 (m, 2H), 5.17-5.08 (m, 1H), 3.74 (s, 2H), 1.43 (d, J=7.0 Hz, 6H).

Reference Example C-2

Synthesis of 5-(aminomethyl)-3-ethyl-1-[4-(trifluoromethyl)phenyl]pyrimidine-2,4-dione hydrochloride (C-2)

The title compound was obtained (yield 3%) using iodoethane instead of 2-iodopropane and by an operation similar to that in Reference Example C-1.

MS (ESI) m/z 314 (M+H)$^+$ $^1$H NMR (300 MHz, DMSO-d$_6$) δ 8.27 (s, 3H), 8.19 (s, 1H), 7.97-7.94 (m, 2H), 7.76-7.73 (m, 2H), 3.96-3.69 (m, 2H), 3.76 (s, 2H), 1.17 (t, J=6.9 Hz, 3H).

Reference Example C-3

Synthesis of 5-(aminomethyl)-3-methyl-1-[4-(trifluoromethyl)phenyl]pyrimidine-2,4-dione hydrochloride (C-3)

The title compound was obtained (yield 1%) using iodomethane instead of 2-iodopropane and by an operation similar to that in Reference Example C-1.

MS (ESI) m/z 300 (M+H)$^+$ $^1$H NMR (300 MHz, CD$_3$OD) δ 7.97 (s, 1H), 7.88-7.86 (m, 2H), 7.68-7.66 (m, 2H), 3.91 (s, 2H), 3.40 (s, 3H).

Reference Example C-4

Synthesis of 3-(aminomethyl)-1-isopropyl-5-[4-(trifluoromethyl)phenyl]pyridin-2-one hydrochloride (C-4)

(Step 1) Synthesis of 2-methoxy-5-[4-(trifluoromethyl)phenyl]pyridine-3-carbonitrile To 5-bromo-2-methoxypyridine-3-carbonitrile (426 mg, 2.00 mmol), [4-(trifluoromethyl)phenyl]boronic acid (760 mg, 4.00 mmol) and 1,1'-bis(diphenylphosphino)-ferrocenedichloropalladium(II) (146 mg, 0.200 mmol) were added 1,4-dioxane (9.5 mL) and 1 mol/L aqueous sodium carbonate solution (9.5 mL), and the mixture was stirred with heating by using a microwave reactor at 100° C. for 20 min. To the reaction mixture was added ethyl acetate, and the mixture was washed successively with water and saturated brine. The organic layer was dried over sodium sulfate. The desiccant was filtered off, the solvent was evaporated, and the obtained residue was purified by silica gel column chromatography (hexane/ethyl acetate) to give the title compound (505 mg, 1.82 mmol, 91%).

MS (ESI) m/z 279 (M+H)$^+$ (Step 2) Synthesis of tert-butyl N-[[2-oxo-5-[4-(trifluoromethyl)phenyl]-1H-pyridin-3-yl]methyl]carbamate To a solution of the compound (300 mg, 1.08 mmol) obtained in step 1 in acetic acid (9 mL) was added 10% palladium/carbon (30 mg), and the mixture was stirred under a hydrogen atmosphere at normal pressure at room temperature for 4 hr. The catalyst was filtered off and the filtrate was concentrated under reduced pressure. To the obtained residue was added 20% hydrogen bromide/acetic acid solution (9 mL), and the mixture was stirred at room temperature for 2 days. The reaction mixture was concentrated under reduced pressure. To the obtained residue were added acetonitrile (9 mL), triethylamine (0.255 mL, 1.83 mmol) and di-tert-butyl dicarbonate (236 mg, 1.08 mmol), and the mixture was stirred at room temperature for 4 hr. The reaction mixture was concentrated under reduced pressure and the obtained residue was purified by silica gel column chromatography (ethyl acetate/methanol) to give the title compound (102 mg, 0.277 mmol, 26%).

MS (ESI) m/z 369 (M+H)$^+$ (Step 3) Synthesis of tert-butyl N-[[1-isopropyl-2-oxo-5-[4-(trifluoromethyl)phenyl]-3-pyridyl]methyl]carbamate To a solution of the compound (102 mg, 0.277 mmol) obtained in step 2 in N,N-dimethylformamide (1.5 mL) were added cesium carbonate (90.1 mg, 0.277 mmol) and 2-iodopropane (33.0 μL, 0.332 mmol) and the mixture was stirred at room temperature overnight. To the reaction mixture was added ethyl acetate, and the mixture was washed with water, and the organic layer was dried over sodium sulfate. The desiccant was filtered off and the filtrate was concentrated under reduced pressure. The obtained residue was purified by silica gel column chromatography (hexane/ethyl acetate) to give the title compound (46.3 mg, 0.113 mmol, 41%).

MS (ESI) m/z 411 (M+H)+

(Step 4) Synthesis of 3-(aminomethyl)-1-isopropyl-5-[4-(trifluoromethyl)phenyl]pyridin-2-one hydrochloride (C-4)

To the compound (46.3 mg, 0.113 mmol) obtained in step 3 was added 4 mol/L hydrochloric acid (1,4-dioxane solution, 3 mL) and the mixture was stirred at room temperature for 1.5 hr. The reaction mixture was concentrated under reduced pressure to give the title compound (39.6 mg, 0.113 mmol, 100%) as a white solid.

MS (ESI) m/z 311 (M+H)+
$^1$H NMR (400 MHz, CD$_3$OD) δ 8.13 (d, J=2.4 Hz, 1H), 8.05 (d, J=2.4 Hz, 1H), 7.74-7.80 (m, 4H), 5.29 (hept, J=6.9 Hz, 1H), 4.10 (s, 2H), 1.49 (d, J=6.9 Hz, 6H).

Reference Example C-5

Synthesis of 5-(aminomethyl)-1-isopropyl-3-[4-(trifluoromethyl)phenyl]pyridin-2-one hydrochloride (C-5)

(Step 1) Synthesis of 6-methoxy-5-[4-(trifluoromethyl)phenyl]pyridine-3-carbonitrile To 5-bromo-6-methoxy-pyridine-3-carbonitrile (200 mg, 0.939 mmol), [4-(trifluoromethyl)phenyl]boronic acid (357 mg, 1.88 mmol) and 1,1'-bis(diphenylphosphino)ferrocenedichloropalladium(II) (34.4 mg, 0.0470 mmol) were added 1,4-dioxane (2.5 mL) and 1 mol/L aqueous sodium carbonate solution (2.5 mL), and the mixture was stirred with heating by using a microwave reactor at 100° C. for 30 min. To the reaction mixture was added ethyl acetate, and the mixture was washed with saturated brine. The organic layer was dried over sodium sulfate. The desiccant was filtered off, the solvent was evaporated and the obtained residue was purified by silica gel column chromatography (hexane/ethyl acetate) to give the title compound (244 mg, 0.877 mmol, 94%).

MS (ESI) m/z 279 (M+H)+

(Step 2) Synthesis of 5-(aminomethyl)-1-isopropyl-3-[4-(trifluoromethyl)phenyl]pyridin-2-one hydrochloride (C-5)

To a solution of the compound (244 mg, 0.877 mmol) obtained in step 1 in acetic acid (12 mL) was added 10% palladium/carbon (50 mg), and the mixture was stirred under a hydrogen atmosphere at normal pressure at room temperature for 6 hr. The catalyst was filtered off and the filtrate was concentrated under reduced pressure. To the obtained residue was added 20% hydrogen bromide/acetic acid solution (5 mL), and the mixture was stirred at 50° C. overnight. The reaction mixture was concentrated under reduced pressure. To the obtained residue were added acetonitrile (5 mL), triethylamine (0.367 mL, 2.63 mmol) and di-tert-butyl dicarbonate (192 mg, 0.877 mmol), and the mixture was stirred at room temperature for 4 hr. The reaction mixture was concentrated under reduced pressure and the obtained residue was dissolved in N,N-dimethylformamide (2.5 mL). Cesium carbonate (572 mg, 1.76 mmol) and 2-iodopropane (175 μL, 1.76 mmol) were added to the solution and the mixture was stirred at room temperature overnight. To the reaction mixture was added ethyl acetate, and the mixture was washed with water. The organic layer was dried over sodium sulfate. The desiccant was filtered off and the filtrate was concentrated under reduced pressure. The obtained residue was purified by silica gel column chromatography (hexane/ethyl acetate). To the obtained compound was added 4 mol/L hydrochloric acid (1,4-dioxane solution, 4 mL) and the mixture was stirred at room temperature for 2 hr. The reaction mixture was concentrated under reduced pressure to give the title compound (91.9 mg, 0.265 mmol, 30%).

MS (ESI) m/z 311 (M+H)+
$^1$H NMR (400 MHz, DMSO-d$_6$) δ 8.41 (brs, 3H), 8.07 (d, J=2.4 Hz, 1H), 7.98 (d, J=8.2 Hz, 2H), 7.96 (d, J=2.4 Hz, 1H), 7.78 (d, J=8.2 Hz, 2H), 5.17 (hept, J=6.8 Hz, 1H), 3.88-3.96 (m, 2H), 1.35 (d, J=6.8 Hz, 6H).

Reference Example C-6

Synthesis of 5-(aminomethyl)-1-[4-(trifluoromethyl)phenyl]pyridin-2-one hydrochloride (C-6)

(Step 1) Synthesis of 5-methyl-1-[4-(trifluoromethyl)phenyl]pyridin-2-one

To 5-methyl-1H-pyridin-2-one (2.0 g, 18 mmol), 1-iodo-4-(trifluoromethyl)benzene (5.9 g, 22 mmol), copper(I) iodide (6.7 g, 3.6 mmol), potassium phosphate (7.7 g, 37 mmol) and N,N'-dimethylethylenediamine (0.70 g, 7.3 mmol) was added 1,4-dioxane (15 mL), and the mixture was stirred under a nitrogen atmosphere at 109° C. overnight. Insoluble material was filtered off through celite, the filtrate was poured into water and the mixture was extracted three times with ethyl acetate. The organic layer was dried over sodium sulfate. The desiccant was filtered off, and the filtrate was concentrated under reduced pressure. The obtained residue was purified by silica gel column chromatography (petroleum ether/ethyl acetate) to give the title compound (4.2 g, 17 mmol, 91%).

1H NMR (400 MHz, DMSO-d$_6$) δ7.90 (d, J=8.0 Hz, 2H), 7.68 (d, J=8.4, Hz, 2H), 7.52 (s, 1H) 7.41 (dd, J=2.8, 9.6 Hz, 1H), 6.48 (d, J=9.2 Hz, 1H) 2.05 (s, 3H).

(Step 2) Synthesis of 5-(bromomethyl)-1-[4-(trifluoromethyl)phenyl]pyridin-2-one To the compound (1.0 g, 3.9 mmol) obtained in step 1, N-bromosuccinimide (0.80 g, 4.7 mmol) and 2,2'-azobis(isobutyronitrile) (0.10 g, 0.61 mmol) was added carbon tetrachloride (15 mL), and the mixture was heated under reflux under a nitrogen atmosphere overnight. The reaction mixture was poured into water, extracted three times with ethyl acetate and the organic layer was dried over sodium sulfate. The desiccant was filtered off, and the filtrate was concentrated under reduced pressure. The obtained residue was purified by silica gel column chromatography (petroleum ether/ethyl acetate) to give the title compound (1.1 g, 3.3 mmol, 84%).

(Step 3) Synthesis of tert-butyl N-[[6-oxo-1-[4-(trifluoromethyl)phenyl]-3-pyridyl]methyl]carbamate To a solution of the compound (0.80 g, 2.4 mmol) obtained in step 2 in N,N-dimethylformamide (15 mL) was added sodium azide (0.20 g, 2.7 mmol), and the mixture was stirred at room temperature for 2 hr. To the reaction mixture was added water. and the mixture was extracted three times with ethyl acetate. The organic layer was dried over sodium sulfate. The desiccant was filtered off, and the filtrate was concentrated under reduced pressure. The obtained residue was dissolved in tetrahydroran (15 mL), palladium/carbon (20 mg) and di-tert-butyl dicarbonate (1.0 g, 4.8 mmol) were added to the solution, and the mixture was stirred under a hydrogen atmosphere at normal pressure at room temperature for 4 hr. The catalyst was filtered off through celite, and the filtrate was concentrated under reduced pressure. The obtained residue was purified by silica gel column chromatography (petroleum ether/ethyl acetate) to give the title compound (0.25 g, 0.66 mmol, 28%).

$^1$H NMR (300 MHz, CDCl$_3$) δ 7.79 (d, J=8.4 Hz, 2H), 7.56 (d, J=8.1 Hz, 2H), 7.45-7.40 (m, 1H), 7.26 (s, 1H), 6.70 (d, J=9.6 Hz, 1H), 4.68 (br s, 1H), 4.11 (d, J=6 Hz, 2H) 1.50 (s, 9H).

(Step 4) Synthesis of 5-(aminomethyl)-1-[4-(trifluoromethyl)phenyl]pyridin-2-one hydrochloride (C-6)

The compound (0.25 g, 0.68 mmol) obtained in step 3 was dissolved in dichloromethane (2 mL), 2 mol/L hydrogen chloride (ethyl acetate solution, 5 mL) was added, and the mixture was stirred at room temperature for 2 hr. The reaction mixture was concentrated under reduced pressure. To the obtained residue was added dichloromethane (2 mL), and insoluble material was collected by filtration to give the title compound as a white powder (0.15 g, 0.50 mmol, 74%).

MS (ESI) m/z 269 (M+H)$^+$ $^1$H NMR (400 MHz, CD$_3$OD) δ7.90-7.86 (m, 3H), 7.74 (d, J=9.4 hz, 1H), 7.67 (d, J=8.0 Hz, 2H), 6.72 (d, J=9.4 Hz, 1H), 4.90 (s, 2H).

Reference Example C-7

Synthesis of 5-(aminomethyl)-3-isopropyl-1-[6-(trifluoromethyl)-3-pyridyl]pyrimidine-2,4-dione (C-7)

(Step 1) Synthesis of tert-butyl 3-isopropyl-5-methyl-2,4-dioxo-pyrimidine-1-carboxylate 5-Methyl-1H-pyrimidine-2,4-dione (25.0 g, 198 mmol) was dissolved in acetonitrile (25.0 mL), N,N-dimethyl-4-aminopyridine (483 mg, 3.96 mmol) and di-tert-butyl dicarbonate (45.4 g, 208 mmol) were added, and the mixture was stirred at room temperature overnight. The solvent was evaporated, water was added and the mixture was extracted with ethyl acetate. The organic layer was washed with saturated brine, and dried over sodium sulfate. The desiccant was filtered off and the solvent was evaporated. To the obtained residue were added potassium carbonate (46.5 g, 337 mmmol), 2-iodopropane (20.1 mL, 202 mmol) and N,N-dimethylformamide (172 mL) and the mixture was stirred at 30° C. overnight. The solvent was evaporated. To the residue was added water and the mixture was extracted with ethyl acetate. The organic layer was dried over sodium sulfate. The desiccant was filtered off, the solvent was evaporated, and the obtained residue was purified by silica gel column chromatography (hexane/ethyl acetate) to give the title compound (23.5 g, 87.6 mmol, 52%).

MS (ESI) m/z 269 (M+H)$^+$ (Step 2) Synthesis of 2-[(3-isopropyl-2,4-dioxo-1H-pyrimidin-5-yl)methyl]isoindoline-1,3-dione The compound (23.5 g, 87.6 mmol) obtained in step 1 was dissolved in carbon tetrachloride (93.0 mL), N-bromosuccinimide (17.1 g, 96.5 mmol) and azobisisobutyronitrile (145 mg, 0.877 mmol) were added and the mixture was stirred at 85° C. overnight. The reaction mixture was allowed to cool to room temperature, filtered through celite by using dichloromethane, and the solvent was evaporated to give tert-butyl 5-(bromomethyl)-3-isopropyl-2,4-dioxo-pyrimidine-1-carboxylate as a crude product. A suspension of potassium carbonate (26.0 g, 189 mmol) and phthalimide (15.2 g, 102 mmol) in N,N-dimethylformamide (120 mL) was stirred at 28° C. for 30 min. An N,N-dimethylformamide solution (52 mL) of the crude product of tert-butyl 5-(bromomethyl)-3-isopropyl-2,4-dioxo-pyrimidine-1-carboxylate was added, and the mixture was stirred at 28° C. overnight. After celite filtration using ethyl acetate, the solvent was evaporated, water was added and the mixture was extracted with ethyl acetate. The organic layer was dried over sodium sulfate. The desiccant was filtered off, the solvent was evaporated, and the obtained residue was purified by silica gel column chromatography (hexane/ethyl acetate) to give the title compound (2.20 g, 7.03 mmol) and tert-butyl 5-[(1,3-dioxoisoindolin-2-yl)methyl]-3-isopropyl-2,4-dioxo-pyrimidine-1-carboxylate (3.41 g, 8.27 mol). The obtained tert-butyl 5-[(1,3-dioxoisoindolin-2-yl)methyl]-3-isopropyl-2,4-dioxo-pyrimidine-1-carboxylate (3.41 g, 8.27 mol) was dissolved in dichloromethane (20.0 mL), trifluoroacetic acid (5.0 mL) was added and the mixture was stirred at room temperature for 30 min. After evaporation of the solvent, saturated aqueous sodium hydrogen carbonate solution was added, and the mixture was extracted with ethyl acetate to further give the title compound (2.59 g, 8.27 mmol) (total yield 18%).

MS (ESI) m/z 314 (M+H)$^+$ (Step 3) Synthesis of 2-[[3-isopropyl-2,4-dioxo-1-[6-(trifluoromethyl)-3-pyridyl]pyrimidin-5-yl]methyl]isoindoline-1,3-dione To the compound (939 mg, 3.00 mmol) obtained in step 2 were added [6-(trifluoromethyl)-3-pyridyl]boronic acid (860 mg, 4.50 mmol), copper acetate (815 mg, 4.50 mmol), pyridine (483 μL, 6.00 mmol), molecular sieves4 Å (500 mg) and N,N-dimethylformamide (30.0 mL), and the mixture was stirred at 45° C. overnight. The reaction mixture was allowed to cool to room temperature, filtered through celite by using ethyl acetate, water and ethylenediaminetetraacetic acid (1.0 g) were added and the mixture was extracted with ethyl acetate and hexane. The organic layer was dried over sodium sulfate. The desiccant was filtered off, the solvent was evaporated and the obtained residue was purified by silica gel column chromatography (hexane/ethyl acetate) to give the title compound (370 mg, 0.808 mmol, 27%).

MS (ESI) m/z 459 (M+H)$^+$ (Step 4) Synthesis of 5-(aminomethyl)-3-isopropyl-1-[6-(trifluoromethyl)-3-pyridyl]pyrimidine-2,4-dione (C-7)

To the compound (370 mg, 0.808 mmol) obtained in step 3 were added hydrazine monohydrate (236 μL, 4.85 mmol) and ethanol (16.0 mL) and the mixture was stirred at 65° C. for 1 hr. Saturated aqueous sodium hydrogen carbonate solution was added, the organic solvent was evaporated, and the mixture was extracted with ethyl acetate. The organic layer was dried over sodium sulfate. The desiccant was filtered off, the solvent was evaporated and the residue was purified by high performance liquid chromatography (water-acetonitrile, each containing 0.1% trifluoroacetic acid). The obtained solid was dissolved in ethyl acetate, washed successively with saturated aqueous sodium hydrogen carbonate solution and saturated brine, and the organic layer was dried over sodium sulfate. The desiccant was filtered off, and the solvent was evaporated to give the title compound (229 mg, 0.698 mmol, 86%).

MS (ESI) m/z 329 (M+H)$^+$

Reference Example C-8

Synthesis of 5-(aminomethyl)-3-isopropyl-1-[5-(trifluoromethyl)-2-pyridyl]pyrimidine-2,4-dione (C-8)

(Step 1) Synthesis of 2-[[3-isopropyl-2,4-dioxo-1-[5-(trifluoromethyl)-2-pyridyl]pyrimidin-5-yl]methyl]isoindoline-1,3-dione To the compound (626 mg, 2.00 mmol) obtained in Reference Example C-7, step 2 were added 2-iodo-5-(trifluoromethyl)pyridine (601 mg, 2.20 mmol), copper iodide (114 mg, 0.6 mmol), 1,8-diazabicyclo[5.4.0]-7-undecene (596 µL, 4.00 mmol), and N,N-dimethylformamide (7.4 mL) and the mixture was stirred with heating by using a microwave reactor at 170° C. for 45 min. The reaction mixture was allowed to cool to room temperature, water was added and the mixture was extracted with dichloromethane. The organic layer was dried over sodium sulfate. The desiccant was filtered off, the solvent was evaporated and the obtained residue was purified by high performance liquid chromatography (water-acetonitrile, each containing 0.1% trifluoroacetic acid) to give the title compound (400 mg, 0.873 mmol, 44%).

MS (ESI) m/z 459 (M+H)$^+$ (Step 2) Synthesis of 5-(aminomethyl)-3-isopropyl-1-[5-(trifluoromethyl)-2-pyridyl]pyrimidine-2,4-dione (C-8)

To the compound (400 mg, 0.873 mmol) obtained in step 1 were added hydrazine monohydrate (127 µL, 2.62 mmol) and ethanol (16.0 mL) and the mixture was stirred at 65° C. for 30 min. Hydrazine monohydrate (127 µL, 2.62 mmol) was further added and the mixture was stirred at 65° C. for 1 hr. The reaction mixture was allowed to cool to room temperature, water was added and the organic solvent was evaporated. Saturated aqueous sodium hydrogen carbonate solution was added, and the mixture was extracted with ethyl acetate. The organic layer was dried over sodium sulfate. The desiccant was filtered off and the solvent was evaporated to give the title compound (286 mg, 0.873 mmol, 99%).

MS (ESI) m/z 329 (M+H)$^+$

Reference Example C-9

Synthesis of 5-(aminomethyl)-1-(4-fluorophenyl)-3-isopropyl-pyrimidine-2,4-dione (C-9)

(Step 1) Synthesis of 2-[[1-(4-fluorophenyl)-3-isopropyl-2,4-dioxo-pyrimidin-5-yl]methyl]isoindoline-1,3-dione The title compound was obtained (yield 80%) using 4-fluorophenylboronic acid instead of [6-(trifluoromethyl)-3-pyridyl]boronic acid and by an operation similar to that in Reference Example C-7, step 3.

MS (ESI) m/z 408 (M+H)$^+$ (Step 2) Synthesis of 5-(aminomethyl)-1-(4-fluorophenyl)-3-isopropyl-pyrimidine-2,4-dione (C-9)

The title compound was obtained (yield 99%) using the compound obtained in step 1 instead of the compound obtained in Reference Example C-8, step 1 and by an operation similar to that in Reference Example C-8, step 2.

MS (ESI) m/z 278 (M+H)$^+$

Reference Example C-10

Synthesis of 5-(aminomethyl)-1-(4-chlorophenyl)-3-isopropyl-pyrimidine-2,4-dione (C-10)

(Step 1) Synthesis of 2-[[1-(4-chlorophenyl)-3-isopropyl-2,4-dioxo-pyrimidin-5-yl]methyl]isoindoline-1,3-dione The title compound was obtained (yield 80%) using 4-chlorophenylboronic acid instead of [6-(trifluoromethyl)-3-pyridyl]boronic acid and by an operation similar to that in Reference Example C-7, step 3.

MS (ESI) m/z 424 (M+H)$^+$ (Step 2) Synthesis of 5-(aminomethyl)-1-(4-chlorophenyl)-3-isopropyl-pyrimidine-2,4-dione (C-10)

The title compound was obtained (yield 99%) using the compound obtained in step 1 instead of the compound obtained in Reference Example C-8, step 1 and by an operation similar to that in Reference Example C-8, step 2.

MS (ESI) m/z 294 (M+H)$^+$

Reference Example C-11

Synthesis of 3-(aminomethyl)-1-isopropyl-5-[6-(trifluoromethyl)-3-pyridyl]pyridin-2-one hydrochloride (C-11)

The title compound was obtained (yield 8%) using [6-(trifluoromethyl)-3-pyridyl]boronic acid instead of [4-(trifluoromethyl)phenyl]boronic acid and by an operation similar to that in Reference Example C-4.

MS (ESI) m/z 312 (M+H)$^+$

Reference Example C-12

Synthesis of 3-(aminomethyl)-1-isopropyl-5-[5-(trifluoromethyl)-2-pyridyl]pyridin-2-one hydrochloride (C-12)

(Step 1) Synthesis of 2-methoxy-5-[5-(trifluoromethyl)-2-pyridyl]pyridine-3-carbonitrile To 5-bromo-2-methoxypyridine-3-carbonitrile (300 mg, 1.41 mmol), bis(pinacolato)diboron (393 mg, 1.55 mmol), 1,1'-bis(diphenylphosphino)ferrocenedichloropalladium(II) (51.5 mg, 0.0704 mmol) and potassium acetate (415 mg, 4.23 mmol) was added 1,4-dioxane (2.4 mL), and the mixture was stirred with heating by using a microwave reactor at, 120° C. for 30 min. To the reaction mixture were added 2-bromo-5-(trifluoromethyl)pyridine (318 mg, 1.41 mmol), 1,1'-bis(diphenylphosphino)ferrocenedichloropalladium(II) (51.5 mg, 0.0704 mmol) and 1 mol/L aqueous sodium carbonate solution (2.4 mL), and the mixture was stirred with heating by using a microwave reactor at 100° C. for 30 min. To the reaction mixture was added ethyl acetate, the mixture was washed with water, and the organic layer was dried over sodium sulfate. The desiccant was filtered off, the solvent was evaporated and the obtained residue was purified by silica gel column chromatography (hexane/ethyl acetate) to give the title compound (370 mg, 1.32 mmol, 94%).

MS (ESI) m/z 280 (M+H)$^+$ (Step 2) Synthesis of [2-methoxy-5-[5-(trifluoromethyl)-2-pyridyl]-3-pyridyl]methanamine ditrifluoroacetate To a solution of the compound (426 mg, 1.53 mmol) obtained in step 1 in acetic acid (30 mL) was added 10% palladium/carbon (85 mg), and the mixture was stirred under a hydrogen atmosphere at normal pressure at room temperature for 14 hr. The catalyst was filtered off and the filtrate was concentrated under reduced pressure. The obtained residue was purified by high performance liquid chromatography (water-acetonitrile, each containing 0.1% trifluoroacetic acid) to give the title compound (276 mg, 0.539 mmol, 35%).

MS (ESI) m/z 284 (M+H)$^+$ (Step 3) Synthesis of 3-(aminomethyl)-1-isopropyl-5-[5-(trifluoromethyl)-2-pyridyl]pyridin-2-one hydrochloride (C-12)

To the compound (276 mg, 0.539 mmol) obtained in step 2 was added 20% hydrogen bromide/acetic acid solution (5 mL), and the mixture was stirred at room temperature for 5 hr. The reaction mixture was concentrated under reduced pressure. To the obtained residue were added acetonitrile (5 mL), triethylamine (0.226 mL, 1.62 mmol) and di-tert-butyl dicarbonate (118 mg, 0.539 mmol), and the mixture was stirred at room temperature overnight. The reaction mixture was concentrated under reduced pressure, the obtained residue was dissolved in N,N-dimethylformamide (5 mL), cesium carbonate (352 mg, 1.08 mmol) and 2-iodopropane (0.107 mL, 1.08 mmol) were added and the mixture was stirred at room temperature overnight. To the reaction mixture was added ethyl acetate, the mixture was washed with water, and the organic layer was dried over sodium sulfate. The desiccant was filtered off and the filtrate was concentrated under reduced pressure. The obtained residue was purified by silica gel column chromatography (hexane/ethyl acetate). To the obtained compound was added 4 mol/L hydrochloric acid (1,4-dioxane solution, 2 mL) and the mixture was stirred at room temperature overnight. The reaction mixture was concentrated under reduced pressure to give the title compound (27.4 mg, 0.0788 mmol, 15%).

MS (ESI) m/z 312 (M+H)$^+$

Reference Example C-13

Synthesis of 5-(aminomethyl)-1-isopropyl-3-[6-(trifluoromethyl)-3-pyridyl]pyridin-2-one hydrochloride (C-13)

The title compound was obtained (yield 7%) using [6-(trifluoromethyl)-3-pyridyl]boronic acid instead of [4-(trifluoromethyl)phenyl]boronic acid and by an operation similar to that in Reference Example C-5.

MS (ESI) m/z 312 (M+H)$^+$

Reference Example C-14

Synthesis of 5-(aminomethyl)-1-isopropyl-3-[5-(trifluoromethyl)-2-pyridyl]pyridin-2-one hydrochloride (C-14)

(Step 1) Synthesis of 6-methoxy-5-[5-(trifluoromethyl)-2-pyridyl]pyridine-3-carbonitrile The title compound was obtained (yield 74%) using 5-bromo-6-methoxy-pyridine-3-carbonitrile instead of 5-bromo-2-methoxypyridine-3-carbonitrile and by an operation similar to that in Reference Example C-12, step 1.

MS (ESI) m/z 280 (M+H)$^+$ (Step 2) Synthesis of 5-(aminomethyl)-1-isopropyl-3-[5-(trifluoromethyl)-2-pyridyl]pyridin-2-one hydrochloride (C-14)

The title compound was obtained (yield 8%) using the compound obtained in step 1 instead of 6-methoxy-5-[4-(trifluoromethyl)phenyl]pyridine-3-carbonitrile and by an operation similar to that in Reference Example C-5, step 2.

MS (ESI) m/z 312 (M+H)$^+$

The structural formulas of the Example compounds are shown in Table 3, and the property values are shown in Table 4.

TABLE 3

| Ex. No. | Structural formula | Compound name |
|---|---|---|
| 1 | 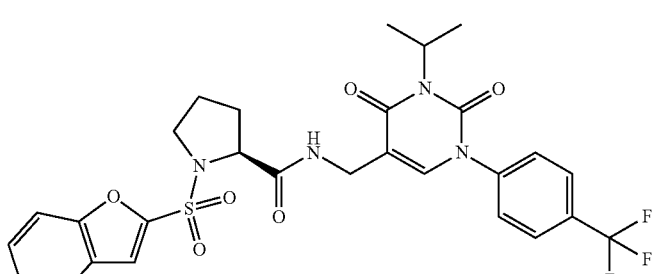 | (2S)-1-(benzofuran-2-ylsulfonyl)-N-[[3-isopropyl-2,4-dioxo-1-[4-(trifluoromethyl)phenyl]pyrimidin-5-yl]methyl]pyrrolidine-2-carboxamide |

TABLE 3-continued

| Ex. No. | Structural formula | Compound name |
| --- | --- | --- |
| 2 | | (2S)-1-(benzofuran-2-ylsulfonyl)-N-[[3-ethyl-2,4-dioxo-1-[4-(trifluoromethyl)phenyl]pyrimidin-5-yl]methyl]pyrrolidine-2-carboxamide |
| 3 | | (2S)-1-(5-fluorobenzofuran-2-yl)sulfonyl-N-[[3-isopropyl-2,4-dioxo-1-[4-(trifluoromethyl)phenyl]-pyrimidin-5-yl]methyl]pyrrolidine-2-carboxamide |
| 4 | | (2S)-1-(5-fluorobenzofuran-2-yl)sulfonyl-N-[[3-ethyl-2,4-dioxo-1-[4-(trifluoromethyl)phenyl]pyrimidin-5-yl]methyl]pyrrolidine-2-carboxamide |
| 5 | | (2S)-1-(5-fluorobenzofuran-2-yl)sulfonyl-N-[[3-methyl-2,4-dioxo-1-[4-(trifluoromethyl)phenyl]-pyrimidin-5-yl]methyl]pyrrolidine-2-carboxamide |
| 6 | | (2S)-2-[(5-fluorobenzofuran-2-yl)sulfonylamino]-N-[[3-methyl-2,4-dioxo-1-[4-(trifluoromethyl)phenyl]-pyrimidin-5-yl]methyl]propanamide |

TABLE 3-continued

| Ex. No. | Structural formula | Compound name |
|---|---|---|
| 7 | | (2S,3S)-1-(benzofuran-2-ylsulfonyl)-3-hydroxy-N-[[3-isopropyl-2,4-dioxo-1-[4-(trifluoromethyl)phenyl]-pyrimidin-5-yl]methyl]pyrrolidine-2-carboxamide |
| 8 | | (2S,3S)-1-(5-fluorobenzofuran-2-yl)sulfonyl-3-hydroxy-N-[[3-isopropyl-2,4-dioxo-1-[4-(trifluoromethyl)phenyl]pyrimidin-5-yl]methyl]pyrrolidine-2-carboxamide |
| 9 | | (2S)-1-(benzofuran-2-ylsulfonyl)-N-[[2,4-dioxo-3-tetrahydropyran-4-yl-1-[4-(trifluoromethyl)phenyl]-pyrimidin-5-yl]methyl]pyrrolidine-2-carboxamide |
| 10 | | (2S)-1-(4-fluorobenzofuran-2-yl)sulfonyl-N-[[3-isopropyl-2,4-dioxo-1-[4-(trifluoromethyl)phenyl]-pyrimidin-5-yl]methyl]pyrrolidine-2-carboxamide |
| 11 | | (2S)-1-[(5-chloro-2-thienyl)sulfonyl]-N-[[3-isopropyl-2,4-dioxo-1-[4-(trifluoromethyl)phenyl]-pyrimidin-5-yl]methyl]pyrrolidine-2-carboxamide |

TABLE 3-continued

| Ex. No. | Structural formula | Compound name |
|---|---|---|
| 12 | | (2S)-1-(4-fluorophenyl)sulfonyl-N-[[3-isopropyl-2,4-dioxo-1-[4-(trifluoromethyl)phenyl]pyrimidin-5-yl]methyl]pyrrolidine-2-carboxamide |
| 13 | | (2S)-1-(benzofuran-2-ylsulfonyl)-N-[[1-isopropyl-6-oxo-5-[4-(trifluoromethyl)phenyl]-3-pyridyl]methyl]pyrrolidine-2-carboxamide |
| 14 | | (2S)-1-(benzofuran-2-ylsulfonyl)-N-[[6-oxo-1-[4-(trifluoromethyl)phenyl]-3-pyridyl]methyl]pyrrolidine-2-carboxamide |
| 15 | | (2S)-1-(benzofuran-2-ylsulfonyl)-N-[[1-isopropyl-2-oxo-5-[4-(trifluoromethyl)phenyl]-3-pyridyl]methyl]pyrrolidine-2-carboxamide |
| 16 | | (2S)-1-(5-fluorobenzofuran-2-yl)sulfonyl-N-[[3-isopropyl-2,4-dioxo-1-[4-(trifluoromethyl)phenyl]-pyrimidin-5-yl]methyl]-2,5-dihydropyrrole-2-carboxamide |

TABLE 3-continued

| Ex. No. | Structural formula | Compound name |
|---|---|---|
| 17 | | (2S)-4,4-difluoro-1-(5-fluorobenzofuran-2-yl)sulfonyl-N-[[3-isopropyl-2,4-dioxo-1-[4-(trifluoromethyl)phenyl]pyrimidin-5-yl]methyl]pyrrolidine-2-carboxamide |
| 18 | | (2S)-1-(5-fluorobenzofuran-2-yl)sulfonyl-N-[[3-isopropyl-2,4-dioxo-1-[4-(trifluoromethyl)phenyl]-pyrimidin-5-yl]methyl]azetidine-2-carboxamide |
| 19 | | (2S)-1-(benzothiophen-2-ylsulfonyl)-N-[[3-isopropyl-2,4-dioxo-1-[4-(trifluoromethyl)phenyl]-pyrimidin-5-yl]methyl]pyrrolidine-2-carboxamide |
| 20 | | (2S)-1-(5-fluorobenzofuran-2-yl)sulfonyl-N-[[1-isopropyl-6-oxo-5-[4-(trifluoromethyl)phenyl]-3-pyridyl]methyl]pyrrolidine-2-carboxamide |
| 21 | | (2S)-1-(5-fluorobenzofuran-2-yl)sulfonyl-N-[[1-isopropyl-2-oxo-5-[4-(trifluoromethyl)phenyl]-3-pyridyl]methyl]pyrrolidine-2-carboxamide |

TABLE 3-continued

| Ex. No. | Structural formula | Compound name |
| --- | --- | --- |
| 22 | | (2S)-1-(5-fluorobenzofuran-2-yl)sulfonyl-N-[[6-oxo-1-[4-(trifluoromethyl)phenyl]-3-pyridyl]methyl]pyrrolidine-2-carboxamide |
| 23 | | (2S)-1-fro[3,2-c]pyridin-2-ylsulfonyl-N-[[3-isopropyl-2,4-dioxo-1-[4-(trifluoromethyl)phenyl]-pyrimidin-5-yl]methyl]pyrrolidine-2-carboxamide |
| 24 | | (2S)-2-[(5-fluorobenzofuran-2-yl)sulfonylamino]-N-[[1-isopropyl-4-methyl-2,6-dioxo-3-[4-(trifluoromethyl)phenyl]pyrimidin-5-yl]methyl]propanamide |
| 25 | | (2S)-N-[[3-isopropyl-2,4-dioxo-1-[4-(trifluoromethyl)phenyl]pyrimidin-5-yl]methyl]-1-(5-methylbenzofuran-2-yl)sulfonyl-pyrrolidine-2-carboxamide |
| 26 | | 1-[(5-fluorobenzofuran-2-yl)sulfonylamino]-N-[[1-isopropyl-4-methyl-2,6-dioxo-3-[4-(trifluoromethyl)phenyl]pyrimidin-5-yl]methyl]-cyclopropanecarboxamide |

TABLE 3-continued

| Ex. No. | Structural formula | Compound name |
| --- | --- | --- |
| 27 | | (2S)-1-fro[3,2-c]pyridin-2-ylsulfonyl-N-[[1-isopropyl-2-oxo-5-[4-(trifluoromethyl)phenyl]-3-pyridyl]methyl]pyrrolidine-2-carboxamide |
| 28 | | (2S)-1-(benzofuran-2-ylsulfonyl)-N-[[1-isopropyl-2-oxo-5-[6-(trifluoromethyl)-3-pyridyl]-3-pyridyl]methyl]pyrrolidine-2-carboxamide |
| 29 | | (2S)-1-(benzofuran-2-ylsulfonyl)-N-[[3-isopropyl-2,4-dioxo-1-[6-(trifluoromethyl)-3-pyridyl]pyrimidin-5-yl]methyl]pyrrolidine-2-carboxamide |
| 30 | | (2S)-1-(5-fluorobenzofuran-2-yl)sulfonyl-N-[[3-isopropyl-2,4-dioxo-1-[6-(trifluoromethyl)-3-pyridyl]pyrimidin-5-yl]methyl]pyrrolidine-2-carboxamide |
| 31 | | (2S,3S)-1-(5-fluorobenzofuran-2-yl)sulfonyl-3-hydroxy-N-[[3-isopropyl-2,4-dioxo-1-[6-(trifluoromethyl)-3-pyridyl]pyrimidin-5-yl]methyl]pyrrolidine-2-carboxamide |

TABLE 3-continued

| Ex. No. | Structural formula | Compound name |
| --- | --- | --- |
| 32 | | (2S)-1-fro[3,2-c]pyridin-2-ylsulfonyl-N-[[3-isopropyl-2,4-dioxo-1-[6-(trifluoromethyl)-3-pyridyl]pyrimidin-5-yl]methyl]pyrrolidine-2-carboxamide |
| 33 | | (2S)-1-(benzofuran-2-ylsulfonyl)-N-[[3-isopropyl-2,4-dioxo-1-[5-(trifluoromethyl)-2-pyridyl]pyrimidin-5-yl]methyl]pyrrolidine-2-carboxamide |
| 34 | | (2S)-1-(5-fluorobenzofuran-2-yl)sulfonyl-N-[[3-isopropyl-2,4-dioxo-1-[5-(trifluoromethyl)-2-pyridyl]pyrimidin-5-yl]methyl]pyrrolidine-2-carboxamide |
| 35 | | (2S,3S)-1-(5-fluorobenzofuran-2-yl)sulfonyl-3-hydroxy-N-[[3-isopropyl-2,4-dioxo-1-[5-(trifluoromethyl)-2-pyridyl]pyrimidin-5-yl]methyl]pyrrolidine-2-carboxamide |
| 36 | | (2S)-1-fro[3,2-c]pyridin-2-ylsulfonyl-N-[[3-isopropyl-2,4-dioxo-1-[5-(trifluoromethyl)-2-pyridyl]pyrimidin-5-yl]methyl]pyrrolidine-2-carboxamide |

TABLE 3-continued

| Ex. No. | Structural formula | Compound name |
|---|---|---|
| 37 | | (2S)-1-(5-fluorobenzofuran-2-yl)sulfonyl-N-[[1-isopropyl-2-oxo-5-[6-(trifluoromethyl)-3-pyridyl]-3-pyridyl]methyl]pyrrolidine-2-carboxamide |
| 38 | | (2S)-1-(benzofuran-2-ylsulfonyl)-N-[[1-(4-fluorophenyl)-3-isopropyl-2,4-dioxo-pyrimidin-5-yl]methyl]pyrrolidine-2-carboxamide |
| 39 | | (2S)-1-(5-fluorobenzofuran-2-yl)sulfonyl-N-[[1-(4-fluorophenyl-3-isopropyl-2,4-dioxo-pyrimidin-5-yl]methyl]pyrrolidine-2-carboxamide |
| 40 | | (2S)-1-(benzofuran-2-ylsulfonyl)-N-[[1-(4-chlorophenyl)-3-isopropyl-2,4-dioxo-pyrimidin-5-yl]methyl]pyrrolidine-2-carboxamide |
| 41 | | (2S)-N-[[1-(4-chlorophenyl)-3-isopropyl-2,4-dioxo-pyrimidin-5-yl]methyl]-1-(5-fluorobenzofuran-2-yl)sulfonyl-pyrrolidine-2-carboxamide |

TABLE 3-continued

| Ex. No. | Structural formula | Compound name |
|---|---|---|
| 42 | | (2S)-1-(benzofuran-2-ylsulfonyl)-N-[[1-isopropyl-2-oxo-5-[5-(trifluoromethyl)-2-pyridyl]-3-pyridyl]methyl]pyrrolidine-2-carboxamide |
| 43 | | (2S)-1-(5-fluorobenzofuran-2-yl)sulfonyl-N-[[1-isopropyl-2-oxo-5-[5-(trifluoromethyl)-2-pyridyl]-3-pyridyl]methyl]pyrrolidine-2-carboxamide |
| 44 | | (2S)-1-(4-fluorobenzofuran-2-yl)sulfonyl-N-[[1-isopropyl-2-oxo-5-[4-(trifluoromethyl)phenyl]-3-pyridyl]methyl]pyrrolidine-2-carboxamide |
| 45 | | (2S)-1-(4-fluorobenzofuran-2-yl)sulfonyl-N-[[1-isopropyl-6-oxo-5-[4-(trifluoromethyl)phenyl]-3-pyridyl]methyl]pyrrolidine-2-carboxamide |
| 46 | | (2S)-1-fro[3,2-c]pyridin-2-ylsulfonyl-N-[[1-isopropyl-6-oxo-5-[4-(trifluoromethyl)phenyl]-3-pyridyl]methyl]pyrrolidine-2-carboxamide |

TABLE 3-continued

| Ex. No. | Structural formula | Compound name |
|---|---|---|
| 47 | | (2S,3S)-1-(5-fluorobenzofuran-2-yl)sulfonyl-3-hydroxy-N-[[1-isopropyl-6-oxo-5-[4-(trifluoromethyl)phenyl]-3-pyridyl]methyl]pyrrolidine-2-carboxamide |
| 48 | | (2S)-1-(benzofuran-2-ylsulfonyl)-N-[[1-isopropyl-6-oxo-5-[6-(trifluoromethyl)-3-pyridyl]-3-pyridyl]methyl]pyrrolidine-2-carboxamide |
| 49 | | (2S)-1-(5-fluorobenzofuran-2-yl)sulfonyl-N-[[1-isopropyl-6-oxo-5-[6-(trifluoromethyl)-3-pyridyl]-3-pyridyl]methyl]pyrrolidine-2-carboxamide |
| 50 | | (2S)-1-(benzofuran-2-ylsulfonyl)-N-[[1-isopropyl-6-oxo-5-[5-(trifluoromethyl)-2-pyridyl]-3-pyridyl]methyl]pyrrolidine-2-carboxamide |
| 51 | | (2S)-1-(5-fluorobenzofuran-2-yl)sulfonyl-N-[[1-isopropyl-6-oxo-5-[5-(trifluoromethyl)-2-pyridyl]-3-pyridyl]methyl]pyrrolidine-2-carboxamide |

TABLE 4

| Ex. No. | MS(ESI) m/z (M + H)+ | NMR |
|---|---|---|
| 1 | 605 | $^1$H NMR (400 MHz, DMSO-d$_6$) δ 8.38 (dd, J = 5.8, 5.8 Hz, 1H), 7.91-7.85 (m, 2H), 7.84-7.79 (m, 1H), 7.73 (dd, J = 8.4, 1.0 Hz, 1H), 7.69-7.62 (m, 3H), 7.60-7.51 (m, 2H), 7.41 (ddd, J = 7.7, 7.6, 0.9 Hz, 1H), 5.12 (hept, J = 6.9 Hz, 1H), 4.22 (dd, J = 8.0, 3.8 Hz, 1H), 4.09-3.95 (m, 2H), 3.58-3.48 (m, 1H), 3.35-3.31 (m, 1H), 1.95-1.79 (m, 3H), 1.66-1.55 (m, 1H), 1.42 (d, J = 6.9 Hz, 6H). |
| 2 | 591 | $^1$H NMR (400 MHz, DMSO-d$_6$) δ 8.39 (dd, J = 6.0, 5.8 Hz, 1H), 7.88 (d, J = 8.4 Hz, 2H), 7.84-7.79 (m, 1H), 7.73 (d, J = 8.4 Hz, 1H), 7.70-7.64 (m, 3H), 7.62 (s, 1H), 7.55 (ddd, J = 8.5, 7.2, 1.3 Hz, 1H), 7.45-7.38 (m, 1H), 4.22 (dd, J = 8.0, 3.8 Hz, 1H), 4.08 (dd, J = 16.0, 6.0 Hz, 1H), 4.05-3.98 (m, 1H), 3.92 (q, J = 7.0 Hz, 2H), 3.58-3.50 (m, 1H), 3.35-3.32 (m, 1H), 1.96-1.77 (m, 3H), 1.68-1.55 (m, 1H), 1.16 (t, J = 7.0 Hz, 3H). |
| 3 | 623 | $^1$H NMR (400 MHz, DMSO-d$_6$) δ 8.38 (dd, J = 5.8, 5.8 Hz, 1H), 7.88 (d, J = 8.4 Hz, 2H), 7.81-7.75 (m, 1H), 7.66 (d, J = 8.4 Hz, 2H), 7.64-7.60 (m, 2H), 7.58-7.56 (m, 1H), 7.42 (ddd, J = 9.3, 9.3, 2.8 Hz, 1H), 5.12 (hept, J = 6.9 Hz, 1H), 4.22 (dd, J = 8.2, 3.7 Hz, 1H), 4.10-3.94 (m, 2H), 3.60-3.55 (m, 1H), 3.40-3.28 (m, 1H), 1.97-1.76 (m, 3H), 1.67-1.55 (m, 1H), 1.42 (d, J = 6.9 Hz, 6H). |
| 4 | 609 | $^1$H NMR (400 MHz, DMSO-d$_6$) δ 8.39 (dd, J = 5.7, 5.7 Hz, 1H), 7.90-7.85 (m, 2H), 7.82-7.75 (m, 1H), 7.70-7.65 (m, 2H), 7.65-7.60 (m, 3H), 7.42 (ddd, J = 9.2, 9.2, 2.7 Hz, 1H), 4.22 (dd, J = 8.1, 3.8 Hz, 1H), 4.11-3.97 (m, 2H), 3.91 (q, J = 7.0 Hz, 2H), 3.55 (ddd, J = 9.4, 6.3, 4.8 Hz, 1H), 3.35-3.27 (m, 1H), 1.96-1.79 (m, 3H), 1.67-1.56 (m, 1H), 1.16 (t, J = 7.0 Hz, 3H). |
| 5 | 595 | $^1$H NMR (400 MHz, DMSO-d$_6$) δ 8.40 (dd, J = 4.9, 4.9 Hz, 1H), 7.89 (d, J = 8.5 Hz, 2H), 7.79 (dd, J = 9.3, 3.5 Hz, 1H), 7.66 (d, J = 8.5 Hz, 2H), 7.64-7.60 (m, 3H), 7.42 (ddd, J = 9.3, 9.2, 2.7 Hz, 1H), 4.22 (dd, J = 8.1, 3.8 Hz, 1H), 4.07 (dd, J = 15.6, 4.9 Hz, 1H), 4.01 (dd, J = 15.6, 4.9 Hz, 1H), 3.59-3.51 (m, 1H), 3.38-3.31 (m, 1H), 3.25 (s, 3H), 1.97-1.80 (m, 3H), 1.66-1.57 (m, 1H). |
| 6 | 569 | $^1$H NMR (400 MHz, DMSO-d$_6$) δ 8.78 (d, J = 8.2 Hz, 1H), 8.20 (t, J = 5.3 Hz, 1H), 7.90 (d, J = 8.4 Hz, 2H), 7.72 (dd, J = 9.0, 4.2 Hz, 1H), 7.66-7.61 (m, 3H), 7.57 (dd, J = 8.5, 2.7 Hz, 1H), 7.44 (d, J = 0.9 Hz, 1H), 7.35 (ddd, J = 9.2, 9.0, 2.7 Hz, 1H), 3.96 (dq, J = 8.2, 7.0 Hz, 1H), 3.87 (d, J = 5.3 Hz, 2H), 3.24 (s, 3H), 1.15 (d, J = 7.0 Hz, 3H). |
| 7 | 621 | $^1$H NMR (400 MHz, DMSO-d$_6$) δ 8.44 (dd, J = 5.8, 5.8 Hz, 1H), 7.90-7.85 (m, 2H), 7.81 (brd, J = 7.8 Hz, 1H), 7.69 (dd, J = 8.5, 1.0 Hz, 1H), 7.66 (d, J = 8.5 Hz, 2H), 7.62 (d, J = 0.9 Hz, 1H), 7.56 (d, J = 1.2 Hz, 1H), 7.53 (ddd, J = 8.5, 7.2, 1.3 Hz, 1H), 7.39 (ddd, J = 7.5, 7.2, 1.0 Hz, 1H), 5.11 (hept, J = 6.9 Hz, 1H), 4.12-3.96 (m, 4H), 3.65-3.59 (m, 1H), 3.50-3.45 (m, 1H), 2.01-1.88 (m, 1H), 1.70 (dd, J = 12.9, 6.2 Hz, 1H), 1.42 (d, J = 6.9 Hz, 6H). |
| 8 | 639 | $^1$H NMR (400 MHz, DMSO-d$_6$) δ 8.45 (dd, J = 5.8, 5.8 Hz, 1H), 7.88 (d, J = 8.5 Hz, 2H), 7.75 (dd, J = 9.1, 4.0 Hz, 1H), 7.66 (d, J = 8.3 Hz, 2H), 7.64-7.59 (m, 2H), 7.56 (s, 1H), 7.39 (ddd, J = 9.2, 9.2, 2.7 Hz, 1H), 5.11 (hept, J = 6.9 Hz, 2H), 4.14-3.96 (m, 4H), 3.62 (ddd, J = 8.6, 8.6, 1.8 Hz, 1H), 3.51-3.45 (m, 1H), 2.00-1.89 (m, 1H), 1.71 (dd, J = 12.8, 6.2 Hz, 1H), 1.42 (d, J = 6.9 Hz, 6H). |
| 9 | 647 | $^1$H NMR (400 MHz, DMSO-d$_6$) δ 8.38 (dd, J = 5.7, 5.7 Hz, 1H), 7.88 (d, J = 8.4 Hz, 2H), 7.84-7.80 (m, 1H), 7.75-7.70 (m, 1H), 7.69-7.63 (m, 3H), 7.59 (d, J = 1.2 Hz, 1H), 7.55 (ddd, J = 8.5, 7.3, 1.3 Hz, 1H), 7.41 (ddd, J = 8.0, 7.3, 0.9 Hz, 1H), 5.06-4.90 (m, 1H), 4.22 (dd, J = 8.0, 3.8 Hz, 1H), 4.11-3.90 (m, 4H), 3.60-3.49 (m, 1H), 3.45-3.38 (m, 1H), 3.30-3.20 (m, 2H), 2.66-2.52 (m, 2H), 1.97-1.79 (m, 3H), 1.67-1.48 (m, 3H). |
| 10 | 623 | $^1$H NMR (400 MHz, DMSO-d$_6$) δ 8.38 (t, J = 5.7 Hz, 1H), 7.87 (d, J = 8.4 Hz, 2H), 7.75 (d, J = 0.8 Hz, 1H), 7.72-7.53 (m, 5H), 7.32-7.22 (m, 1H), 5.12 (hept, J = 6.9 Hz, 1H), 4.22 (dd, J = 8.2, 3.8 Hz, 1H), 4.09-3.94 (m, 2H), 3.61-3.51 (m, 1H), 3.44-3.34 (m, 1H), 2.02-1.78 (m, 3H), 1.70-1.57 (m, 1H), 1.42 (d, J = 6.9 Hz, 6H). |
| 11 | 605 | $^1$H NMR (400 MHz, DMSO-d$_6$) δ 8.35 (t, J = 5.8 Hz, 1H), 7.86 (d, J = 8.3 Hz, 2H), 7.65 (d, J = 8.3 Hz, 2H), 7.62 (d, J = 4.1 Hz, 1H), 7.56 (d, J = 1.2 Hz, 1H), 7.35 (d, J = 4.1 Hz, 1H), 5.11 (hept, J = 6.9 Hz, 1H), 4.10-3.94 (m, 3H), 3.52-3.42 (m, 1H), 3.25-3.15 (m, 1H), 1.92-1.77 (m, 3H), 1.67-1.54 (m, 1H), 1.42 (d, J = 6.9 Hz, 6H). |
| 12 | 583 | $^1$H NMR (400 MHz, DMSO-d$_6$) δ 8.33 (t, J = 5.8 Hz, 1H), 7.92-7.81 (m, 4H), 7.65 (d, J = 8.1 Hz, 2H), 7.60 (s, 1H), 7.49-7.40 (m, 2H), 5.12 (hept, J = 6.9 Hz, 1H), 4.09-3.96 (m, 3H), 3.44-3.35 (m, 1H), 3.19-3.09 (m, 1H), 1.87-1.69 (m, 3H), 1.56-1.46 (m, 1H), 1.42 (d, J = 6.9 Hz, 6H). |
| 13 | 588 | $^1$H NMR (400 MHz, DMSO-d$_6$) δ 8.65 (t, J = 5.9 Hz, 1H), 7.93 (d, J = 7.8 Hz, 2H), 7.86-7.80 (m, 1H), 7.77-7.69 (m, 5H), 7.65 (d, J = 2.4 Hz, 1H), 7.56 (ddd, J = 8.5, 7.3, 1.3 Hz, 1H), 7.46-7.38 (m, 1H), 5.19 (hept, J = 6.8 Hz, 1H), 4.27 (dd, J = 8.4, 3.6 Hz, 1H), 4.22 (dd, J = 15.0, 6.0 Hz, 1H), 4.17 (dd, J = 15.0, 5.7 Hz, 1H), 3.64-3.55 (m, 1H), 3.38-3.31 (m, 1H), 2.01-1.80 (m, 3H), 1.68-1.59 (m, 1H), 1.34 (d, J = 6.8 Hz, 3H), 1.34 (d, J = 6.8 Hz, 3H). |
| 14 | 546 | — |
| 15 | 588 | — |
| 16 | 621 | $^1$H NMR (400 MHz, DMSO-d$_6$) δ 8.52 (dd, J = 6.0, 5.4 Hz, 1H), 7.88 (d, J = 8.2 Hz, 2H), 7.77 (dd, J = 9.1, 3.9 Hz, 1H), 7.70-7.59 (m, 4H), 7.54 (s, 1H), 7.42 (ddd, J = 9.3, 9.1, 2.8 Hz, 1H), 5.95-5.89 (m, 1H), 5.75-5.68 (m, 1H), 5.12 (hept, J = 6.9 Hz, 1H), 5.05-4.97 (m, 1H), 4.39-4.28 (m, 1H), 4.28-4.19 (m, 1H), 4.08 (dd, J = 15.6, 6.0 Hz, 1H), 3.97 (dd, J = 15.6, 5.4 Hz, 1H), 1.42 (d, J = 6.9 Hz, 6H). |
| 17 | 659 | $^1$H NMR (400 MHz, DMSO-d$_6$) δ 8.60 (t, J = 5.7 Hz, 1H), 7.87 (d, J = 8.2 Hz, 2H), 7.78 (dd, J = 9.0, 4.1 Hz, 1H), 7.70 (d, J = 0.9 Hz, 1H), 7.69-7.63 (m, 3H), 7.61 (s, 1H), 7.44 (ddd, J = 9.2, 9.0, 2.7 Hz, 1H), 5.12 (hept, J = 6.9 Hz, 1H), 4.47 (dd, J = 8.7, 6.9 Hz, 1H), 4.03 (d, J = 5.7 Hz, 2H), 4.01-3.86 (m, 2H), 2.81-2.64 (m, 1H), 2.46-2.35 (m, 1H), 1.42 (d, J = 6.9 Hz, 6H). |
| 18 | 609 | $^1$H NMR (400 MHz, DMSO-d$_6$) δ 8.41 (dd, J = 6.0, 5.4 Hz, 1H), 7.91-7.80 (m, 3H), 7.74 (d, J = 0.9 Hz, 1H), 7.71-7.64 (m, 3H), 7.61 (s, 1H), 7.46 (ddd, J = 9.3, 9.0, 2.8 Hz, 1H), 5.12 (hept, J = 6.9 Hz, 1H), 4.56 (dd, J = 9.1, 7.5 Hz, 1H), 4.11 (dd, J = 15.4, 6.0 Hz, 1H), 4.02 (dd, J = 15.4, 5.4 Hz, 1H), 3.93-3.78 (m, 2H), 2.31-2.15 (m, 2H), 1.42 (d, J = 6.9 Hz, 6H). |

TABLE 4-continued

| Ex. No. | MS(ESI) m/z (M + H)+ | NMR |
|---|---|---|
| 19 | 621 | $^1$H NMR (400 MHz, DMSO-d$_6$) δ 8.38 (dd, J = 5.8, 5.7 Hz, 1H), 8.14-8.09 (m, 2H), 8.07-8.02 (m, 1H), 7.86 (d, J = 8.1 Hz, 2H), 7.67 (d, J = 8.1 Hz, 2H), 7.62-7.50 (m, 3H), 5.12 (hept, J = 6.9 Hz, 1H), 4.14-4.02 (m, 2H), 4.01 (dd, J = 15.4, 5.7 Hz, 1H), 3.60-3.49 (m, 1H), 3.31-3.24 (m, 1H), 1.88-1.75 (m, 3H), 1.63-1.51 (m, 1H), 1.43 (d, J = 6.9 Hz, 6H). |
| 20 | 606 | $^1$H NMR (400 MHz, DMSO-d$_6$) δ 8.63 (t, J = 6.0 Hz, 1H), 8.09 (d, J = 2.6 Hz, 1H), 7.85 (d, J = 8.2 Hz, 2H), 7.80 (dd, J = 9.1, 4.1 Hz, 1H), 7.76-7.71 (m, 3H), 7.70-7.68 (m, 1H), 7.64 (dd, J = 8.5, 2.7 Hz, 1H), 7.43 (td, J = 9.3, 2.8 Hz, 1H), 5.17 (hept, J = 6.8 Hz, 1H), 4.34 (dd, J = 8.2, 3.7 Hz, 1H), 4.22 (dd, J = 17.0, 6.2 Hz, 1H), 4.12 (dd, J = 16.9, 5.6 Hz, 1H), 3.65-3.67 (m, 1H), 3.46-3.36 (m, 1H), 2.06-1.84 (m, 3H), 1.74-1.58 (m, 1H), 1.41 (d, J = 6.8 Hz, 6H). |
| 21 | 606 | $^1$H NMR (400 MHz, DMSO-d$_6$) δ 8.65 (t, J = 5.9 Hz, 1H), 7.93 (d, J = 8.1 Hz, 2H), 7.80 (dd, J = 9.2, 4.1 Hz, 1H), 7.76-7.68 (m, 4H), 7.65 (d, J = 2.5 Hz, 1H), 7.63 (dd, J = 8.5, 2.6 Hz, 1H), 7.42 (td, J = 9.2, 2.8 Hz, 1H), 5.19 (hept, J = 6.8 Hz, 1H), 4.26 (dd, J = 8.4, 3.6 Hz, 1H), 4.23 (dd, J = 15.4, 6.0 Hz, 1H), 4.17 (dd, J = 15.0, 5.8 Hz, 1H), 3.63-3.56 (m, 1H), 3.38 (dt, J = 9.9, 6.8 Hz, 1H), 2.04-1.80 (m, 3H), 1.70-1.58 (m, 1H), 1.34 (d, J = 7.0 Hz, 3H), 1.33 (d, J = 6.9 Hz, 3H). |
| 22 | 564 | $^1$H NMR (400 MHz, DMSO-d$_6$) δ 8.58 (t, J = 5.9 Hz, 1H), 7.90 (d, J = 8.4 Hz, 2H), 7.80 (dd, J = 9.2, 4.1 Hz, 1H), 7.68-7.60 (m, 5H), 7.48 (dd, J = 9.5, 2.5 Hz, 1H), 7.42 (td, J = 9.2, 2.8 Hz, 1H), 6.54 (d, J = 9.5 Hz, 1H), 4.23 (dd, J = 8.2, 3.6 Hz, 1H), 4.11 (d, J = 5.9 Hz, 2H), 3.62-3.52 (m, 1H), 3.38 (dt, J = 9.8, 6.8 Hz, 3H), 2.01-1.78 (m, 3H), 1.70-1.58 (m, 1H). |
| 23 | 606 | $^1$H NMR (400 MHz, DMSO-d$_6$) δ 9.20 (d, J = 1.0 Hz, 1H), 8.71 (d, J = 6.0 Hz, 1H), 8.40 (t, J = 5.7 Hz, 1H), 7.93 (dt, J = 6.0, 1.1 Hz, 1H), 7.88 (d, J = 8.5 Hz, 2H), 7.82 (d, J = 1.0 Hz, 1H), 7.66 (d, J = 8.3 Hz, 2H), 7.58 (s, 1H), 5.12 (hept, J = 6.9 Hz, 1H), 4.24 (dd, J = 8.3, 3.7 Hz, 1H), 4.05 (dd, J = 15.5, 5.6 Hz, 1H), 3.98 (dd, J = 15.5, 5.6 Hz, 1H), 3.63-3.54 (m, 1H), 3.54-3.49 (m, 1H), 2.05-1.79 (m, 3H), 1.73-1.61 (m, 1H), 1.43 (d, J = 6.9 Hz, 6H). |
| 24 | 597 | $^1$H NMR (400 MHz, DMSO-d$_6$) δ 8.79 (d, J = 8.1 Hz, 1H), 8.20 (t, J = 5.5 Hz, 1H), 7.89 (d, J = 8.5 Hz, 2H), 7.73 (dd, J = 9.1, 4.0 Hz, 1H), 7.64 (d, J = 8.3 Hz, 2H), 7.60-7.51 (m, 2H), 7.44 (d, J = 0.8 Hz, 1H), 7.36 (td, J = 9.2, 2.7 Hz, 1H), 5.11 (hept, J = 6.9 Hz, 1H), 4.02-3.91 (m, 1H), 3.86 (d, J = 5.4 Hz, 2H), 1.41 (d, J = 6.9 Hz, 6H), 1.14 (d, J = 7.0 Hz, 3H). |
| 25 | 619 | $^1$H NMR (400 MHz, DMSO-d$_6$) δ 8.37 (t, J = 5.8 Hz, 1H), 7.90-7.84 (m, 2H), 7.66 (d, J = 8.3 Hz, 2H), 7.63-7.55 (m, 4H), 7.36 (dd, J = 8.6, 1.8 Hz, 1H), 5.12 (hept, J = 6.9 Hz, 1H), 4.20 (dd, J = 7.8, 4.0 Hz, 1H), 4.05 (dd, J = 15.8, 5.7 Hz, 1H), 3.99 (dd, J = 15.7, 5.2 Hz, 1H), 3.58-3.50 (m, 1H), 3.33 (dt, J = 9.5, 6.5 Hz, 1H), 2.42 (s, 3H), 1.93-1.77 (m, 3H), 1.58 (dd, J = 8.4, 3.8 Hz, 1H), 1.42 (d, J = 6.9 Hz, 6H). |
| 26 | 609 | $^1$H NMR (400 MHz, DMSO-d$_6$) δ 9.32 (s, 1H), 8.01 (t, J = 6.0 Hz, 1H), 7.90 (d, J = 8.2 Hz, 2H), 7.78 (ddd, J = 9.1, 4.1, 0.9 Hz, 1H), 7.67 (d, J = 8.2 Hz, 2H), 7.59 (dd, J = 8.5, 2.7 Hz, 1H), 7.56 (s, 1H), 7.50 (d, J = 0.9 Hz, 1H), 7.40 (ddd, J = 9.2, 9.1, 2.7 Hz, 1H), 5.12 (hept, J = 6.9 Hz, 1H), 3.93 (d, J = 6.0 Hz, 2H), 1.42 (d, J = 6.9 Hz, 6H), 1.23-1.15 (m, 2H), 0.91-0.84 (m, 2H), |
| 27 | 589 | $^1$H NMR (400 MHz, DMSO-d$_6$) δ 9.19 (d, J = 0.8 Hz, 1H), 8.70 (d, J = 5.9 Hz, 1H), 8.64 (dd, J = 6.2, 5.8 Hz, 1H), 8.09 (d, J = 2.6 Hz, 1H), 7.94-7.88 (m, 2H), 7.86 (d, J = 8.1 Hz, 2H), 7.74 (d, J = 8.1 Hz, 2H), 7.71-7.66 (m, 1H), 5.17 (hept, J = 6.8 Hz, 1H), 4.35 (dd, J = 8.5, 3.6 Hz, 1H), 4.21 (dd, J = 17.0, 6.2 Hz, 1H), 4.12 (dd, J = 17.0, 5.8 Hz, 1H), 3.68-3.58 (m, 1H), 3.45-3.38 (m, 1H), 2.11-1.85 (m, 3H), 1.77-1.63 (m, 1H), 1.41 (d, J = 6.8 Hz, 6H). |
| 28 | 589 | $^1$H NMR (400 MHz, DMSO-d$_6$) δ 9.05 (d, J = 2.3 Hz, 1H), 8.63 (dd, J = 6.3, 5.6 Hz, 1H), 8.29 (dd, J = 8.2, 1.9 Hz, 1H), 8.22 (d, J = 2.6 Hz, 1H), 7.92 (dd, J = 8.2, 0.8 Hz, 1H), 7.84 (ddd, J = 7.9, 1.3, 1.0 Hz, 1H), 7.79-7.71 (m, 3H), 7.56 (ddd, J = 8.5, 7.3, 1.3 Hz, 1H), 7.42 (ddd, J = 7.9, 7.3, 0.9 Hz, 1H), 5.18 (hept, J = 6.9 Hz, 1H), 4.33 (dd, J = 8.2, 3.8 Hz, 1H), 4.24 (dd, J = 17.1, 6.3 Hz, 1H), 4.12 (dd, J = 17.1, 5.6 Hz, 1H), 3.66-3.57 (m, 1H), 3.41-3.36 (m, 1H), 2.04-1.84 (m, 3H), 1.71-1.58 (m, 1H), 1.42 (d, J = 6.9 Hz, 6H). |
| 29 | 606 | $^1$H NMR (400 MHz, DMSO-d$_6$) δ 8.86 (d, J = 2.4 Hz, 1H), 8.38 (t, J = 5.8 Hz, 1H), 8.20 (dd, J = 8.4, 2.4 Hz, 1H), 8.08 (dd, J = 8.5, 0.7 Hz, 1H), 7.84-7.80 (m, 1H), 7.73 (dq, J = 8.4, 0.9 Hz, 1H), 7.67-7.63 (m, 2H), 7.55 (ddd, J = 8.5, 7.2, 1.3 Hz, 1H), 7.41 (ddd, J = 8.0, 7.3, 0.9 Hz, 1H), 5.11 (hept, J = 6.9 Hz, 1H), 4.23 (dd, J = 8.0, 3.8 Hz, 1H), 4.07 (dd, J = 16.3, 5.7 Hz, 1H), 4.00 (dd, J = 14.9, 5.1 Hz, 1H), 3.58-3.50 (m, 1H), 3.35 (dt, J = 9.6, 6.6 Hz, 1H), 1.96-1.80 (m, 3H), 1.67-1.54 (m, 1H), 1.43 (d, J = 6.8 Hz, 6H). |
| 30 | 624 | $^1$H NMR (400 MHz, DMSO-d$_6$) δ 8.86 (d, J = 2.4 Hz, 1H), 8.39 (t, J = 5.8 Hz, 1H), 8.20 (dd, J = 8.5, 2.4 Hz, 1H), 8.08 (d, J = 8.4 Hz, 1H), 7.79 (dd, J = 9.2, 4.0 Hz, 1H), 7.68-7.59 (m, 3H), 7.42 (td, J = 9.2, 2.8 Hz, 1H), 5.12 (hept, J = 6.9 Hz, 1H), 4.23 (dd, J = 8.2, 3.6 Hz, 1H), 4.07 (dd, J = 15.6, 5.8 Hz, 1H), 4.00 (dd, J = 15.6, 5.6 Hz, 1H), 3.61-3.50 (m, 1H), 3.36 (dt, J = 9.6, 6.6 Hz, 1H), 2.00-1.79 (m, 3H), 1.68-1.56 (m, 1H), 1.43 (d, J = 6.9 Hz, 6H). |
| 31 | 640 | $^1$H NMR (400 MHz, DMSO-d$_6$) δ 8.86 (d, J = 2.4 Hz, 1H) 8.46 (t, J = 5.8 Hz, 1H), 8.20 (dd, J = 8.5, 2.4 Hz, 1H), 8.09 (d, J = 8.5 Hz, 1H), 7.75 (dd, J = 9.2, 4.0 Hz, 1H), 7.65-7.58 (m, 3H), 7.39 (td, J = 9.2, 2.8 Hz, 1H), 5.11 (hept, J = 6.8 Hz, 1H), 4.17-3.95 (m, 4H), 3.62 (t, J = 8.4 Hz, 1H), 3.50-3.39 (m, 1H), 1.95 (dtd, J = 12.4, 8.6, 4.2 Hz, 1H), (1.71 (dd, J = 13.0, 6.2 Hz, 1H), 1.43 (d, J = 6.9 Hz, 6H). |
| 32 | 607 | $^1$H NMR (400 MHz, DMSO-d$_6$) δ 9.25 (s, 1H), 8.86 (s, 1H), 8.75 (d, J = 6.1 Hz, 1H), 8.40 (t, J = 6.2 Hz, 1H), 8.20 (d, J = 8.5 Hz, 1H), 8.09 (d, J = 8.4 Hz, 1H), 8.01 (d, J = 6.1 Hz, 1H), 7.86 (s, 1H), 7.65 (s, 1H), 5.12 (hept, J = 6.2 Hz, 1H), 4.26 (dd, J = 8.6, 3.7 Hz, 1H), 4.06 (dd, J = 15.4, 5.8 Hz, 1H), 3.99 (dd, J = 15.6, 5.7 Hz, 1H), 3.65-3.51 (m, 1H), 3.44-3.33 (m, 1H), 2.04-1.79 (m, 3H), 1.74-1.60 (m, 1H), 1.43 (d, J = 6.9 Hz, 6H). |

TABLE 4-continued

| Ex. No. | MS(ESI) m/z (M + H)+ | NMR |
|---|---|---|
| 33 | 606 | ¹H NMR (400 MHz, DMSO-d₆) δ 8.95-8.92 (m, 1H), 8.47 (t, J = 5.8 Hz, 1H), 8.41 (dd, J = 8.8, 2.5 Hz, 1H), 8.03 (d, J = 8.6 Hz, 1H), 7.97-7.95 (m, 1H), 7.84-7.80 (m, 1H), 7.74 (dd, J = 8.4, 1.0 Hz, 1H), 7.68 (d, J = 0.9 Hz, 1H), 7.55 (ddd, J = 8.5, 7.2, 1.3 Hz, 1H), 7.45-7.38 (m, 1H), 5.14 (hept, J = 7.0 Hz, 1H), 4.26 (dd, J = 7.6, 3.8 Hz, 1H), 4.04 (d, J = 5.7 Hz, 2H) 3.57-3.51 (m, 1H) 3.36 (dt, J = 10.1, 6.6 Hz, 1H), 1.96-1.81 (m, 3H), 1.69-1.57 (m, 1H), 1.43 (d, J = 10.6, 6.9 Hz, 6H). |
| 34 | 624 | ¹H NMR (400 MHz, DMSO-d₆) δ 8.93 (brs, 1H), 8.47 (t, J = 5.8 Hz, 1H), 8.41 (dd, J = 8.7, 2.5 Hz, 1H), 8.03 (d, J = 8.6 Hz, 1H), 7.96 (s, 1H), 7.80 (dd, J = 9.2, 4.0 Hz, 1H), 7.67-7.60 (m, 2H), 7.42 (td, J = 9.3, 2.8 Hz, 1H), 5.14 (hept, J = 6.8 Hz, 1H), 4.26 (dd, J = 7.8, 3.5 Hz, 1H), 4.04 (d, J = 5.7 Hz, 2H), 3.55-3.52 (m, 1H), 3.36 (dt, J = 10.1, 6.6 Hz, 1H), 1.99-1.81 (m, 3H), 1.72-1.57 (m, 1H), 1.44 (d, J = 6.9 Hz, 6H). |
| 35 | 640 | ¹H NMR (400 MHz, DMSO-d₆) δ 8.95-8.91 (m, 1H), 8.54 (t, J = 5.8 Hz, 1H), 8.41 (dd, J = 8.7, 2.5 Hz, 1H), 8.03 (d, J = 8.6 Hz, 1H), 7.94 (brs, 1H), 7.76 (dd, J = 9.1, 4.1 Hz, 1H), 7.65-7.59 (m, 2H), 7.39 (td, J = 9.2, 2.8 Hz, 1H), 5.13 (hept, J = 6.8 Hz, 1H), 4.14 (d, J = 3.2 Hz, 1H), 4.08-4.01 (m, 3H), 3.65-3.59 (m, 1H), 3.52-3.42 (m, 1H), 2.04-1.91 (m, 1H), 1.74 (dd, J = 13.4, 6.4 Hz, 1H), 1.44 (d, J = 6.9 Hz, 6H). |
| 36 | 607 | ¹H NMR (400 MHz, DMSO-d₆) δ 9.20 (brs, 1H), 8.95-8.92 (m, 1H), 8.72 (d, J = 6.0 Hz, 1H), 8.49 (t, J = 5.8 Hz, 1H), 8.41 (dd, J = 8.8, 2.5 Hz, 1H), 8.03 (d, J = 8.6 Hz, 1H), 7.98-7.93 (m, 2H), 7.84 (d, J = 1.0 Hz, 1H), 5.13 (hept, J = 6.7 Hz, 1H), 4.28 (dd, J = 8.3, 3.5 Hz, 1H), 4.03 (d, J = 5.7 Hz, 2H), 3.63-3.54 (m, 1H), 3.39 (dt, J = 9.7, 6.9 Hz, 1H), 2.03-1.81 (m, 3H), 1.75-1.63 (m, 1H), 1.44 (d, J = 6.9 Hz, 6H). |
| 37 | 607 | ¹H NMR (400 MHz, DMSO-d₆) δ 9.04 (d, J = 2.3 Hz, 1H), 8.64 (dd, J = 6.0, 5.7 Hz, 1H), 8.33-8.26 (m, 1H), 8.22 (d, J = 2.6 Hz, 1H), 7.93 (dd, J = 8.4, 0.8 Hz, 1H), 7.83-7.77 (m, 1H), 7.76-7.71 (m, 2H), 7.65 (dd, J = 8.4, 2.7 Hz, 1H), 7.43 (ddd, J = 9.3, 9.2, 2.7 Hz, 1H), 5.18 (hept, J = 6.8 Hz, 1H), 4.34 (dd, J = 8.3, 3.7 Hz, 1H), 4.24 (dd, J = 17.0, 6.0 Hz, 1H), 4.13 (dd, J = 17.0, 5.7 Hz, 1H), 3.67-3.56 (m, 1H), 3.45-3.36 (m, 1H), 2.08-1.84 (m, 3H), 1.72-1.61 (m, 1H), 1.42 (d, J = 6.8 Hz, 6H). |
| 38 | 555 | ¹H NMR (400 MHz, DMSO-d₆) δ 8.37 (t, J = 5.8 Hz, 1H), 7.82 (d, J = 7.8 Hz, 1H), 7.73 (d, J = 8.4 Hz, 1H), 7.65 (s, 1H), 7.55 (ddd, J = 8.5, 7.2, 1.4 Hz, 1H), 7.49 (s, 1H), 7.48-7.38 (m, 3H), 7.35-7.29 (m, 2H), 5.11 (hept, J = 6.3, 5.9 Hz, 1H), 4.22 (dd, J = 8.2, 3.7 Hz, 1H), 4.04 (dd, J = 15.8, 5.9 Hz, 1H), 3.98 (dd, J = 15.6, 5.5 Hz, 1H), 3.58-3.50 (m, 1H), 3.34 (dt, J = 9.5, 6.5 Hz, 1H), 1.95-1.78 (m, 3H), 1.66-1.54 (m, 1H), 1.41 (d, J = 6.9 Hz, 6H). |
| 39 | 573 | ¹H NMR (400 MHz, DMSO-d₆) δ 8.37 (t, J = 5.8 Hz, 1H), 7.79 (dd, J = 9.0, 4.2 Hz, 1H), 7.65-7.60 (m, 2H), 7.50-7.43 (m, 3H), 7.41 (td, J = 9.2, 2.8 Hz, 1H), 7.36-7.28 (m, 2H), 5.11 (hept, J = 7.2 Hz, 1H), 4.21 (dd, J = 8.2, 3.8 Hz, 1H), 4.04 (dd, J = 16.7, 5.9 Hz, 1H), 3.97 (dd, J = 15.2, 5.4 Hz, 1H), 3.59-3.50 (m, 1H), 3.35 (dt, J = 9.9, 6.7 Hz, 1H), 1.97-1.78 (m, 3H), 1.68-1.56 (m, 1H), 1.41 (d, J = 6.8 Hz, 6H). |
| 40 | 571 | ¹H NMR (400 MHz, DMSO-d₆) δ 8.38 (t, J = 5.8 Hz, 1H), 7.82 (d, J = 7.8 Hz, 1H), 7.74 (d, J = 8.4 Hz, 1H), 7.66 (d, J = 1.0 Hz, 1H), 7.58-7.52 (m, 3H), 7.50 (hrs, 1H), 7.47-7.38 (m, 3H), 5.11 (hept, J = 7.3 Hz, 1H), 4.22 (dd, J = 8.1, 3.8 Hz, 1H), 4.05 (dd, J = 15.6, 5.8 Hz, 1H), 3.98 (dd, J = 15.5, 5.6 Hz, 1H), 3.59-3.50 (m, 1H), 3.34 (dt, J = 9.7, 6.5 Hz, 1H), 1.96-1.78 (m, 3H), 1.67-1.54 (m, 1H), 1.41 (d, J = 6.9 Hz, 6H). |
| 41 | 589 | ¹H NMR (400 MHz, DMSO-d₆) δ 8.38 (t, J = 5.8 Hz, 1H), 7.79 (dd, J = 9.1, 4.0 Hz, 1H), 7.65-7.61 (m, 2H), 7.58-7.52 (m, 2H), 7.50 (brs, 1H), 7.46-7.38 (m, 3H), 5.11 (hept, J = 6.8 Hz, 1H), 4.22 (dd, J = 8.2, 3.7 Hz, 1H), 4.04 (dd, J = 15.6, 4.9 Hz, 1H), 3.97 (dd, J = 15.9, 5.5 Hz, 1H), 3.59-3.50 (m, 1H), 3.35 (dt, J = 9.8, 6.7 Hz, 1H), 1.98-1.78 (m, 3H), 1.67-1.55 (m, 1H), 1.41 (d, J = 6.9 Hz, 6H). |
| 42 | 589 | ¹H NMR (400 MHz, DMSO-d₆) δ 8.97-8.88 (m, 1H), 8.63 (dd, J = 6.1, 6.0 Hz, 1H), 8.51 (d, J = 2.5 Hz, 1H), 8.22 (ddd, J = 8.6, 2.4, 0.8 Hz, 1H), 8.12 (d, J = 8.6 Hz, 1H), 8.07-8.02 (m, 1H), 7.83 (ddd, J = 8.0, 1.4, 0.7 Hz, 1H), 7.79-7.71 (m, 2H), 7.58 (ddd, J = 8.6, 7.3, 1.4 Hz, 1H), 7.42 (ddd, J = 8.0, 7.3, 0.9 Hz, 1H), 5.17 (hept, J = 6.7 Hz, 1H), 4.36 (dd, J = 7.5, 3.9 Hz, 1H), 4.26-4.09 (m, 2H), 3.80-3.57 (m, 1H), 3.47-3.36 (m, 1H), 2.03-1.88 (m, 3H), 1.75-1.63 (m, 1H), 1.41 (d, J = 6.8 Hz, 6H). |
| 43 | 607 | ¹H NMR (400 MHz, DMSO-d₆) δ 8.95-8.89 (m, 1H), 8.63 (dd, J = 6.4, 6.0 Hz, 1H), 8.51 (d, J = 2.5 Hz, 1H), 8.22 (dd, J = 8.6, 2.1 Hz, 1H), 8.11 (d, J = 8.6 Hz, 1H), 8.03 (dd, J = 2.4, 1.3 Hz, 1H), 7.80 (dd, 7 = 9.2, 4.1 Hz, 1H), 7.72 (d, J = 0.9 Hz, 1H), 7.63 (dd, J = 8.5, 2.8 Hz, 1H), 7.42 (ddd, J = 9.3, 9.2, 2.8 Hz, 1H), 5.17 (hept, J = 6.8 Hz, 1H), 4.36 (dd, J = 7.8, 3.5 Hz, 1H), 4.25-4.08 (m, 2H), 3.68-3.58 (m, 1H), 3.54-3.48 (m, 1H), 2.05-1.85 (m, 3H), 1.79-1.65 (m, 1H), 1.41 (d, J = 6.8 Hz, 6H). |
| 44 | 606 | ¹H NMR (400 MHz, DMSO-d₆) δ 8.62 (dd, J = 6.1, 5.8 Hz, 1H), 8.09 (d, J = 2.6 Hz, 1H), 7.90-7.83 (m, 3H), 7.74 (d, J = 8.1 Hz, 2H), 7.73-7.67 (m, 1H), 7.66-7.54 (m, 2H), 7.27 (ddd, J = 9.6, 7.7, 1.2 Hz, 1H), 5.18 (hept, J = 6.8 Hz, 1H), 4.35 (dd, J = 8.3, 3.7 Hz, 1H), 4.21 (dd, J = 17.1, 6.1 Hz, 1H), 4.13 (dd, J = 17.1, 5.8 Hz, 1H), 3.66-3.57 (m, 1H), 3.48-3.39 (m, 1H), 2.06-1.85 (m, 3H), 1.73-1.61 (m, 1H), 1.41 (d, J = 6.8 Hz, 6H). |
| 45 | 606 | ¹H NMR (400 MHz, DMSO-d₆) δ 8.65 (t, J = 5.9 Hz, 1H), 7.93 (d, J = 7.9 Hz, 2H), 7.84 (d, J = 0.9 Hz, 1H), 7.77-7.69 (m, 3H), 7.68-7.53 (m, 3H), 7.27 (ddd, J = 9.7, 7.8, 1.0 Hz, 1H), 5.19 (hept, J = 6.8 Hz, 1H), 4.28 (dd, J = 8.4, 3.7 Hz, 1H), 4.28-4.12 (m, 2H), 3.60-3.56 (m, 1H), 3.53-3.35 (m, 1H), 2.05-1.80 (m, 3H), 1.70-1.60 (m, 1H), 1.34 (d, J = 6.8 Hz, 3H), 1.34 (d, J = 6.8 Hz, 3H). |
| 46 | 589 | ¹H NMR (400 MHz, DMSO-d₆) δ 9.20 (d, J = 1.0 Hz, 1H), 8.71 (d, J = 6.0 Hz, 1H), 8.66 (dd, J = 6.0, 5.7 Hz, 1H), 7.98-7.90 (m, 3H), 7.89 (d, J = 1.0 Hz, 1H), 7.74 (d, J = 8.7 Hz, 2H), 7.71 (d, J = 2.4 Hz, 1H), 7.65 (d, J = 2.4 Hz, 1H), 5.19 (hept, J = 6.8 Hz, 1H), 4.28 (dd, J = 8.6, 3.6 Hz, 1H), 4.22 (dd, J = 15.0, 6.0 Hz, 1H), 4.16 (dd, J = 15.0, 5.7 Hz, 1H), 3.63-3.58 (m, 1H), 3.44-3.36 (m, 1H), 2.06-1.96 (m, 1H), 1.95-1.80 (m, 2H), 1.74-1.63 (m, 1H), 1.34 (d, J = 6.8 Hz, 3H), 1.33 (d, J = 6.8 Hz, 3H). |

TABLE 4-continued

| Ex. No. | MS(ESI) m/z (M + H)+ | NMR |
|---|---|---|
| 47 | 622 | $^1$H NMR (400 MHz, DMSO-$d_6$) δ 8.74 (dd, J = 6.3, 5.8 Hz, 1H), 7.93 (d, J = 7.8 Hz, 2H), 7.80-7.71 (m, 3H), 7.69 (d, J = 2.5 Hz, 1H), 7.68-7.60 (m, 3H), 7.40 (ddd, J = 9.2, 9.2, 2.8 Hz, 1H), 5.19 (hept, J = 6.8 Hz, 1H), 4.25 (dd, J = 14.9, 6.3 Hz, 1H), 4.19-4.09 (m, 2H), 4.06 (s, 1H), 3.71-3.64 (m, 1H), 3.53-3.42 (m, 1H), 2.01-1.88 (m, 1H), 1.78-1.70 (m, 1H), 1.34 (d, J = 6.8 Hz, 6H). |
| 48 | 589 | $^1$H NMR (400 MHz, DMSO-$d_6$) δ 9.05 (d, J = 2.2 Hz, 1H), 8.66 (dd, J = 6.0, 5.7 Hz, 1H), 8.42 (dd, J = 8.2, 1.8 Hz, 1H), 7.94 (dd, J = 8.2, 0.8 Hz, 1H), 7.83 (ddd, J = 7.8, 1.2, 0.6 Hz, 1H), 7.80-7.72 (m, 4H), 7.56 (ddd, J = 8.4, 7.2, 1.2 Hz, 1H), 7.42 (ddd, J = 7.8, 7.2, 0.9 Hz, 1H), 5.19 (hept, J = (6.8 Hz, 1H), 4.31-4.20 (m, 2H), 4.18 (dd, J = 15.1, 5.7 Hz, 1H), 3.64-3.56 (m, 1H), 3.40-3.33 (m, 1H), 2.01-1.81 (m, 3H), 1.68-1.57 (m, 1H), 1.349 (d, J = 6.8 Hz, 3H), 1.346 (d, J = 6.8 Hz, 3H). |
| 49 | 607 | $^1$H NMR (400 MHz, DMSO-$d_6$) δ 9.05 (d, J = 2.1 Hz, 1H), 8.67 (dd, J = 6.0, 5.6 Hz, 1H), 8.41 (dd, J = 8.2, 1.9 Hz, 1H), 7.93 (d, J = 8.2 Hz, 1H), 7.84-7.75 (m, 3H), 7.70 (d, J = 0.9 Hz, 1H), 7.64 (dd, J = 8.5, 2.8 Hz, 1H), 7.43 (ddd, J = 9.2, 9.2, 2.8 Hz, 1H), 5.18 (hept, J = 6.8 Hz, 1H), 4.29-4.21 (m, 2H), 4.18 (dd, J = 14.9, 5.6 Hz, 1H), 3.64-3.55 (m, 1H), 3.42-3.33 (m, 1H), 2.05-1.80 (m, 3H), 1.70-1.58 (m, 1H), 1.34 (d, J = 6.6 Hz, 6H). |
| 50 | 589 | $^1$H NMR (400 MHz, DMSO-$d_6$) δ 9.00-8.95 (m, 1H), 8.81 (d, J = 8.5 Hz, 1H), 8.69 (t, J = 5.9 Hz, 1H), 8.42 (d, J = 2.6 Hz, 1H), 8.28-8.20 (m, 1H), 7.85 (d, J = 2.6 Hz, 1H), 7.82 (ddd, J = 7.8, 1.4, 0.9 Hz, 1H), 7.75 (dd, J = 8.5, 0.9 Hz, 1H), 7.72 (d, J = 0.9 Hz, 1H), 7.56 (ddd, J = 8.5, 7.3, 1.4 Hz, 1H), 7.42 (ddd, J = 8.0, 7.3, 0.9 Hz, 1H), 5.26 (hept, J = 6.8 Hz, 1H), 4.31-4.16 (m, 3H), 3.63-3.56 (m, 1H), 3.40-3.33 (m, 1H), 1.98-1.81 (m, 3H), 1.69-1.57 (m, 1H), 1.36 (d, J = 6.8 Hz, 6H). |
| 51 | 607 | $^1$H NMR (400 MHz, DMSO-$d_6$) δ 8.94-8.87 (m, 1H), 8.74 (d, J = 8.5 Hz, 1H), 8.63 (t, J = 5.9 Hz, 1H), 8.35 (d, J = 2.6 Hz, 1H), 8.17 (dd, J = 8.5, 2.3 Hz, 1H), 7.78 (d, J = 2.6 Hz, 1H), 7.74 (dd, J = 9.1, 4.0 Hz, 1H), 7.62 (d, J = 0.9 Hz, 1H), 7.56 (dd, J = 8.5, 2.8 Hz, 1H), 7.35 (ddd, J = 9.3, 9.1, 2.8 Hz, 1H), 5.19 (hept, J = 6.8 Hz, 1H), 4.25-4.09 (m, 3H), 3.57-3.49 (m, 1H), 3.36-3.25 (m, 1H), 1.95-1.73 (m, 3H), 1.66-1.52 (m, 1H), 1.29 (d, J = 6.8 Hz, 6H). |

Example 1

Synthesis of (2S)-1-(benzofuran-2-ylsulfonyl)-N-[[3-isopropyl-2,4-dioxo-1-[4-(trifluoromethyl)phenyl]pyrimidin-5-yl]methyl]pyrrolidine-2-carboxamide (1)

To B-1 (29 mg, 0.10 mmol), C-1 (36 mg, 0.10 mmol), WSC hydrochloride (24 mg, 0.12 mmol) and 1-hydroxy-7-azabenzotriazole (16 mg, 0.12 mmol) were added dichloromethane (1 mL) and triethylamine (20 µL, 0.15 mmol) and the mixture was stirred at room temperature for 2 hr. The reaction mixture was concentrated under reduced pressure and the obtained residue was purified by high performance liquid chromatography (water-acetonitrile, each containing 0.1% trifluoroacetic acid) to give the title compound (44 mg, 0.073 mmol, 73%).

MS (ESI) m/z 605 (M+H)+

$^1$H NMR (400 MHz, DMSO-$d_6$) δ 8.38 (dd, J=5.8, 5.8 Hz, 1H), 7.91-7.85 (m, 2H), 7.84-7.79 (m, 1H), 7.73 (dd, J=8.4, 1.0 Hz, 1H), 7.69-7.62 (m, 3H), 7.60-7.51 (m, 2H), 7.41 (ddd, J=7.7, 7.6, 0.9 Hz, 1H), 5.12 (hept, J=6.9 Hz, 1H), 4.22 (dd, J=8.0, 3.8 Hz, 1H), 4.09-3.95 (m, 2H), 3.58-3.48 (m, 1H), 3.35-3.31 (m, 1H), 1.95-1.79 (m, 3H), 1.66-1.55 (m, 1H), 1.42 (d, J=6.9 Hz, 6H).

Example 2 to Example 8 were synthesized by using the compounds described in Reference Examples and corresponding commercially available reagents and by an operation similar to that in Example 1.

Example 9

Synthesis of (2S)-1-(benzofuran-2-ylsulfonyl)-N-[[2,4-dioxo-3-tetrahydropyran-4-yl-1-[4-(trifluoromethyl)phenyl]pyrimidin-5-yl]methyl]pyrrolidine-2-carboxamide (9)

(Step 1) Synthesis of 5-(aminomethyl)-1-[4-(trifluoromethyl)phenyl]pyrimidine-2,4-dione hydrochloride The title compound was obtained (yield 34%) by an operation similar to that in Reference Example C-1 except step 2 which is an alkylation step using 2-iodopropane.
MS (ESI) m/z 286 (M+H)+

$^1$H NMR (300 MHz, DMSO-$d_6$) δ 11.9 (s, 1H), 8.23 (s, 3H), 8.14 (s, 1H), 7.91 (d, J=8.4 Hz, 2H), 7.71 (d, J=8.4 Hz, 2H), 3.72 (s, 2H).

(Step 2) Synthesis of tert-butyl N-[[2,4-dioxo-3-tetrahydropyran-4-yl-1-[4-(trifluoromethyl)phenyl]pyrimidin-5-yl]methyl]carbamate The compound (64 mg, 0.2 mmol) obtained in step 1 was dissolved in dichloromethane (2.0 mL), triethylamine (82 µL, 0.60 mmol) and di-tert-butyl dicarbonate (48 mg, 0.22 mmol) were added, and the mixture was stirred at room temperature for two nights. To the reaction mixture was added water, and the mixture was extracted with dichloromethane. The organic layer was washed with saturated brine, and dried over sodium sulfate. The desiccant was filtered off, and the solvent was evaporated. To a residue (46 mg, 0.12 mmol) weighed from the obtained residue (77 mg, 0.2 mmol) were added potassium carbonate (82 mg, 0.59 mmol), potassium iodide (2.0 mg, 0.012 mmol), N,N-dimethylformamide (1.5 mL) and 4-bromotetrahydropyran (33 µL, 0.30 mmol) and the mixture was stirred at 100° C. overnight. The reaction mixture was neutralized with 0.1% aqueous trifluoroacetic acid solution, and purified by high performance liquid chromatography (water-acetonitrile, each containing 0.1% trifluoroacetic acid) to give the title compound (5 mg, 0.011 mmol, 9.2%).

MS (ESI) m/z 470 (M+H)$^+$ (Step 3) Synthesis of (2S)-1-(benzofuran-2-ylsulfonyl)-N-[[2,4-dioxo-3-tetrahydropyran-4-yl-1-[4-(trifluoromethyl)phenyl]pyrimidin-5-yl]methyl]pyrrolidine-2-carboxamide (9)

To the compound (5 mg, 0.011 mmol) obtained in step 2 was added 4 mol/L hydrochloric acid/1,4-dioxane (1 mL), and the mixture was stirred at room temperature for 30 min, and concentrated under reduced pressure. To the obtained residue were added B-1 (5.8 mg, 0.020 mmol), WSC hydrochloride (4.5 mg, 0.024 mmol) and 1-hydroxy-7-azabenzotriazole (3.3 mg, 0.024 mmol), dichloromethane (1 mL) and triethylamine (4.0 μL, 0.029 mmol) and the mixture was stirred at room temperature for 1 hr. The reaction mixture was concentrated under reduced pressure and the obtained residue was purified by high performance liquid chromatography (water-acetonitrile, each containing 0.1% trifluoroacetic acid) to give the title compound (5.2 mg, 0.0080 mmol, 73%).

MS (ESI) m/z 647 (M+H)$^+$
1H NMR (400 MHz, DMSO-d$_6$) δ 8.38 (dd, J=5.7, 5.7 Hz, 1H), 7.88 (d, J=8.4 Hz, 2H), 7.84-7.80 (n, 1H), 7.75-7.70 (m, 1H), 7.69-7.63 (m, 3H), 7.59 (d, J=1.2 Hz, 1H), 7.55 (ddd, J=8.5, 7.3, 1.3 Hz, 1H), 7.41 (ddd, J=8.0, 7.3, 0.9 Hz, 1H), 5.06-4.90 (m, 1H), 4.22 (dd, J=8.0, 3.8 Hz, 1H), 4.11-3.90 (m, 4H), 3.60-3.49 (m, 1H), 3.45-3.38 (m, 1H), 3.30-3.20 (m, 2H), 2.66-2.52 (m, 2H), 1.97-1.79 (m, 3H), 1.67-1.48 (m, 3H).

Example 10 to Example 51 were synthesized by using the compounds described in Reference Examples and corresponding commercially available reagents and by an operation similar to that in Example 1.

Experimental Example 1

Measurement of TRPA1 Antagonist Activity

Human TRPA1 Expression Plasmid

Using cDNA encoding human TRPA1 (GenBank accession No. NM_007332) (manufactured by Kazusa DNA Research Institute, item No. FHC07217) as a template, primer 1 (SEQ ID NO: 1) and primer 2 (SEQ ID NO: 2), PCR by PfuUltra High-Fidelity DNA Polymerase (Stratagene) was performed, and full-length human TRPA1 gene was amplified.

```
primer 1:
                                    (SEQ ID NO: 1)
5'-AACTTTTAGTAAGCTTCGATCGCCATGAAG-3' primer 2:
                                    (SEQ ID NO: 2)
5'-GTACCGATCTAGAATTCGTTTTACTAAGGCTCAAG-3'
```

A recognition site (underlined) of restriction enzyme HindIII was added to the 5' end of human TRPA1 gene, and XbaI site (underlined) was added to the 3' end of human TRPA1 gene, and GTT of the template sequence was changed to termination codon TAG (bold). The obtained double stranded DNA was enzyme-digested with HindIII and XbaI, and introduced into a multicloning site of expression plasmid pcDNA3.1/zeo(+) (manufactured by Invitrogen) to give a human TRPA1 expression plasmid.

Cell Preparation

Human embryonic kidney-derived 293T cells were cultured in Dulbecco's Modified Eagle Medium containing 10% fetal bovine serum, 10 unit penicillin, and 10 μg streptomycin. One day before assay, 3×10$^6$ of 293T cells were plated on a petri dish having a diameter of 10 cm, and cultured in a CO$_2$ incubator for 24 hr. OPTI-MEM I Reduced Serum Media (Invitrogen) (600 μL), Mirus TransIT-293 (Mirus Bio) (18 μL), and human TRPA1 expression plasmid (6 μg) were mixed, the total amount of the mixture was added to the cells on the petri dish to allow for gene transfer. The cells were recovered about for 8 hr later, plated on a poly-D-lysine coated 384 well black/clear bottom plate at 12,000 cells/well, and cultured overnight.

Measurement of Intracellular Calcium Increase

The medium was removed from the 384 well plate, calcium indicator (Molecular Device, trade name: FLIPR Calcium4 Assay Kit) dissolved in HBSS (Thermo Fisher Scientific) (pH 7.2) containing 20 mM HEPES was added (38 μL/well), and the cells were stained in a CO$_2$ incubator for 1 hr. The 384 well plate was stood at room temperature for not less than 15 min, set on FDSS7000 (Hamamatsu Photonics K.K.), and a test substance solution was added at 10 μL/well. After 10 min, allylisothiocyanate solution (12 μL/well) was added, the relative fluorescence intensity was measured for 5 min after addition of the allylisothiocyanate solution.

Test Substance Preparation

Preparation of Test Substance Solution and Allylisothiocyanate Solution

A test substance solution was prepared to have a composition of HBSS (Thermo Fisher Scientific) (pH 7.2) containing 0.48% dimethyl sulfoxide, a test substance at 4.8-fold concentration of the evaluation concentration, 0.1% bovine serum albumin and 20 mM HEPES. An allylisothiocyanate solution was prepared to have a composition of HBSS (Thermo Fisher Scientific) (pH 7.2) containing 0.1% dimethyl sulfoxide, 100 μM allylisothiocyanate, 0.1% bovine serum albumin and 20 mM HEPES.

Calculation of Antagonist Activity

The activity rate of a test substance at each concentration was calculated, wherein the relative fluorescence intensity change of a well free of a test substance and containing allylisothiocyanate is 100% activity rate, and the relative fluorescence intensity change of a well free of a test substance and allylisothiocyanate is 0% activity rate. The inhibitory rate of a test substance at each concentration was calculated by subtracting the activity rate of the test substance from 100% activity rate, and the concentration of a test substance showing 50% inhibitory rate was calculated as IC50 from the sigmoid approximate curve by XLfit (idbs).

The results are shown in Table 5.

TABLE 5

| Example No. | hTRPA1 IC50 (μM) |
|---|---|
| 1 | 0.016 |
| 2 | 0.026 |
| 3 | 0.0073 |
| 4 | 0.011 |
| 5 | 0.021 |
| 6 | 0.54 |
| 7 | 0.22 |
| 8 | 0.064 |
| 9 | 0.14 |
| 10 | 0.025 |
| 11 | 0.033 |
| 12 | 0.12 |

TABLE 5-continued

| Example No. | hTRPA1 IC50 (μM) |
|---|---|
| 13 | 0.027 |
| 14 | 0.16 |
| 15 | 0.079 |
| 16 | 0.0036 |
| 17 | 0.046 |
| 18 | 0.0090 |
| 19 | 0.056 |
| 20 | 0.049 |
| 21 | 0.0089 |
| 22 | 0.060 |
| 23 | 0.020 |
| 24 | 0.042 |
| 25 | 0.42 |
| 26 | 0.25 |
| 27 | 0.093 |
| 28 | 0.18 |
| 29 | 0.030 |
| 30 | 0.010 |
| 31 | 0.38 |
| 32 | 0.57 |
| 33 | 0.044 |
| 34 | 0.018 |
| 35 | 0.16 |
| 36 | 0.20 |
| 37 | 0.031 |
| 38 | 0.24 |
| 39 | 0.10 |
| 40 | 0.085 |
| 41 | 0.024 |
| 42 | 0.079 |
| 43 | 0.023 |
| 44 | 0.44 |
| 45 | 0.086 |
| 46 | 0.098 |
| 47 | 0.23 |
| 48 | 0.21 |
| 49 | 0.045 |
| 50 | 0.11 |
| 51 | 0.081 |

Experimental Example 2

AITC-Induced Pain Behavior Evaluation Test

To evaluate the effectiveness of the test substance in vivo, an allylisothiocyanate (AITC)-induced pain behavior evaluation test may be performed using mice.

AITC is a selective agonist of the TRPA1 channel, and causes a pain behavior by TRPA1 activation when administered to animal. Therefore, the intensity of the TRPA1 antagonist action of the test substance in the living body can be evaluated by measuring the pain behavior after AITC administration.

1. Administration of Test Substance to Animal

As the animal, male ICR mice (6- to 8-week-old) are used. The mice are fasted on the previous day of the test. The test substance is intraperitoneally or orally administered for evaluation. In the case of intraperitoneal administration, the substance is administered 30 min before the AITC administration. In the case of oral administration, the substance is administered 60 min before the AITC administration.

2. AITC-Induced Pain Behavior Evaluation

AITC (0.1%) is subcutaneously administered to the sole of the left leg of mouse, and the time when the mouse shows a behavior of licking the sole of the leg (Licking time) in 5 min immediately after the AITC administration is measured.

3. Calculation of Inhibitory Rate

The licking time of the vehicle administration group in each test is taken as 100%, and the activity rate by administration of each test substance (Licking time of test substance administration/Licking time of vehicle administration group×100) is determined, and the numerical value obtained by subtracting the activity rate from 100 is calculated as an inhibitory rate.

By the above-mentioned method, it can be confirmed that the compound of the present invention has a superior TRPA1 antagonist activity, is superior pharmacokinetics, and shows superior efficacy in animal model.

Experimental Example 3

AITC-Induced Rat Blood Flow Evaluation Test

To evaluate the effectiveness of the test substance in vivo, allylisothiocyanate (AITC)-induced blood flow evaluation test was performed using rat.

AITC is a selective agonist of the TRPA1 channel, and causes an increase in the peripheral blood flow through TRPA1 activation when applied to animal. Therefore, the intensity of the TRPA1 antagonist action of the test substance in the living body can be evaluated by measuring the increase in the peripheral blood flow after AITC application.

1. Administration of Test Substance to Animal

As the animal, 9-11-week-old male SD rats were used. A test substance was orally administered 60 min before AITC application and evaluated. On the previous day, the blood flow was measured when vehicle was administered to the same individual.

2. Evaluation of AITC-Induced Blood Flow

Under isoflurane anesthesia, the rats were placed in a prone position and a laser was irradiated with a probe of a laser Doppler flowmeter (OMEGA FLOW FLO-N1 neuro science, inc) at a distance of 1 cm from the ear of the rat, and the blood flow was measured, which was recorded using Power lab. After confirmation of stable blood flow, 15 μL of AITC (1%) solution was applied to be spread on the ear of the rat and the blood flow was measured for 20 min.

3. Calculatuin of Inhibitory Rate

Mean blood flow for 10 seconds at each analysis time point (1, 5, 10, 15, 20 min) was calculated, and the amount of change from the blood flow before AITC application was calculated as AUC (Area under the curve). AUC (% of baseline) was determined by normalizing the value obtained by (mean of AUC after test substance administration/mean of AUC after vehicle administration to the same individual)×100 with the ratio of AUC obtained by vehicle administration for the both days. The inhibition ratio was determined by 100−AUC (% of baseline).

The results are shown in FIG. 1, Table 6.

TABLE 6

| Example No. | dose (mg/kg) | rat blood flow model (% inh.) |
|---|---|---|
| 1 | 0.3 | 45 |
| 1 | 1 | 56 |
| 1 | 3 | 58 |

INDUSTRIAL APPLICABILITY

The compounds of the present invention have a TRPA1 antagonist activity, and therefore, is utilizable for the prophylaxis and/or treatment of diseases involving TRPA1 (e.g., pain associated diseases, digestive tract diseases, lung diseases, bladder diseases, inflammatory diseases, dermatic diseases, and neurological diseases).

In view of this object, the compounds of the present invention show a certain level of blood concentration or bioavailability by oral administration, shows sustainability of the blood concentration, and is possibly utilizable as an oral preparation.

In addition, the compounds of the present invention show a certain level of stability in acidic or alkaline solutions and can be applied to various dosage forms.

Furthermore, the compounds of the present invention specifically inhibit TRPA1. That is, the compound of the present invention has selectivity to a molecular target, and can be used safely.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (I):

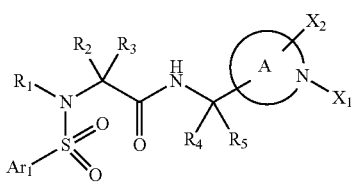

(I)

wherein ring A is a 6-membered, nitrogen-containing heterocycle substituted by 1 or 2 oxo groups;

$Ar_1$ is a $C_{6-10}$ aryl group optionally having substituent(s), a $C_{1-9}$ heteroaryl group optionally having substituent(s), or a $C_{3-7}$ cycloalkyl group optionally having substituent(s);

$R_1$ is hydrogen or a $C_{1-6}$ alkyl group optionally having substituent(s);

$R_2$ is hydrogen, a $C_{1-6}$ alkyl group optionally having substituent(s) or a $C_{2-6}$ alkenyl group optionally having substituent(s);

$R_3$ is hydrogen or a $C_{1-6}$ alkyl group;

$R_4$ is hydrogen or a $C_{1-6}$ alkyl group;

$R_5$ is hydrogen or a $C_{1-6}$ alkyl group;

$R_1$ and $R_2$ are optionally joined to form a nitrogen-containing ring optionally having substituent(s);

$R_2$ and $R_3$ are optionally joined to form cycloalkene or cycloalkane;

$R_4$ and $R_5$ are optionally joined to form cycloalkane;

one of $X_1$ and $X_2$ is one member selected from the following Group A, and the other is an alkyl group optionally having substituent(s), wherein said substituents are optionally joined to form a ring, or a hydrogen atom provided that when ring A is a ring having a pyridone skeleton, $X_1$ is not a hydrogen atom; and $X_1$ and $X_2$ are not hydrogen atoms at the same time;

wherein Group A is selected from the group consisting of hydrogen,
—Cy,
—C($R_{x1}R_{x2}$)-Cy,
—C($R_{x1}R_{x2}$)—C($R_{x3}R_{x4}$)-Cy,
—C($R_{x1}$)=C($R_{x2}$)-Cy,
—O-Cy,
—O—C($R_{x1}R_{x2}$)-Cy,
—C($R_{x1}R_{x2}$)—O-Cy,
—S(O)n-Cy,
—S(O)n-C($R_{x1}R_{x2}$)-Cy,
—C($R_{x1}R_{x2}$)—S(O)n-Cy,
—N($R_{x5}$)-Cy,
—N($R_{x5}$)—C($R_{x1}R_{x2}$)-Cy,
—C($R_{x1}R_{x2}$)—N($R_{x5}$)-Cy,
—C(O)—N($R_{x5}$)-Cy, —N(R$_{x5}$)—C(O)-Cy,
—S(O)m-N(R$_{x5}$)-Cy,
—N(R$_{x5}$)—S(O)m-Cy, and
—O—S(O)m-Cy wherein n is an integer of 0 to 2; m is 1 or 2; Cy is a saturated or unsaturated cyclic group optionally having substituent(s), optionally containing heteroatom (s); R$_{x1}$, R$_{x2}$, R$_{x3}$, R$_{x4}$, and R$_{x5}$ are the same or different and each is hydrogen, a C$_{1-6}$ alkyl group optionally having substituent(s), or a C$_{1-6}$ alkoxycarbonyl group optionally having substituent(s), or a pharmaceutically acceptable salt thereof.

2. The compound or salt according to claim 1, wherein the 6-membered, nitrogen-containing heterocycle substituted by 1 or 2 oxo groups is selected from the group consisting of oxopyridine, dioxopyridine, oxopyrimidine, and dioxopyrimidine.

3. The compound or salt according to claim 1, wherein:
R$_1$ is a hydrogen or a C$_{1-6}$ alkyl group optionally having substituent(s);
R$_2$ is a hydrogen or a C$_{1-6}$ alkyl group optionally having substituent(s);
R$_3$ is hydrogen;
R$_4$ is hydrogen or a C$_{1-6}$ alkyl group;
R$_5$ is hydrogen or a C$_{1-6}$ alkyl group;
R$_1$ and R$_2$ are optionally joined to form a nitrogen-containing ring optionally having substituent(s);
X$_1$ is
-Cy,
—C(R$_{x1}$R$_{x2}$)-Cy,
—C(R$_{x1}$R$_{x2}$)—C(R$_{x3}$R$_{x4}$)-Cy,
—C(R$_{x1}$)=C(R$_{x2}$)-Cy,
—O-Cy,
—O—C(R$_{x1}$R$_{x2}$)-Cy,
—C(R$_{x1}$R$_{x2}$)—O-Cy,
—S(O)n-Cy,
—S(O)n-C(R$_{x1}$R$_{x2}$)-Cy,
—C(R$_{x1}$R$_{x2}$)—S(O)n-Cy,
—N(R$_{x5}$)-Cy,
—N(R$_{x5}$)—C(R$_{x1}$R$_{x2}$)-Cy,
—C(R$_{x1}$R$_{x2}$)—N(R$_{x5}$)-Cy,
—C(O)—N(R$_{x5}$)-Cy,
—N(R$_{x5}$)—C(O)-Cy,
—S(O)m-N(R$_{x5}$)-Cy,
—N(R$_{x5}$)—S(O)m-Cy or
—O—S(O)m-Cy; and
X$_2$ is an alkyl group optionally having substituent(s), wherein said substituents are optionally joined to form a ring.

4. The compound or salt according to claim 1, wherein R$_1$ and R$_2$ are joined to form a nitrogen-containing ring optionally having substituent(s).

5. The compound or salt according to claim 1, wherein R$_1$ is hydrogen and R$_2$ is a C$_{1-6}$ alkyl group.

6. The compound or salt according to claim 1, wherein partial structure (a):

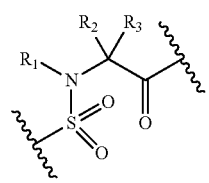

(a)

is a group of any of the following formulas:

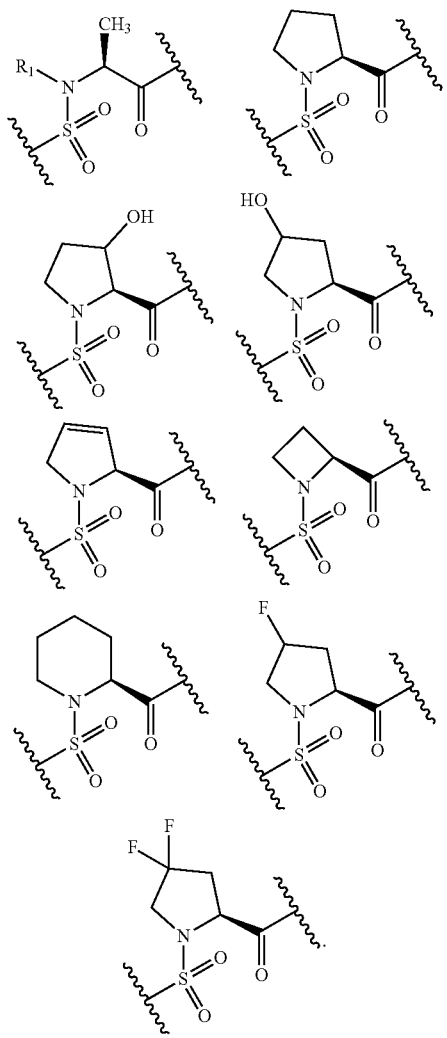

7. The compound or salt according to claim 1, wherein partial structure (b) containing ring A:

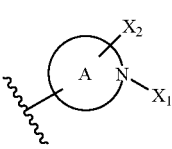

(b)

is a group of any of the following formulas:

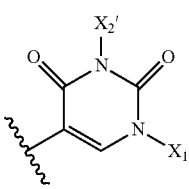

(i)

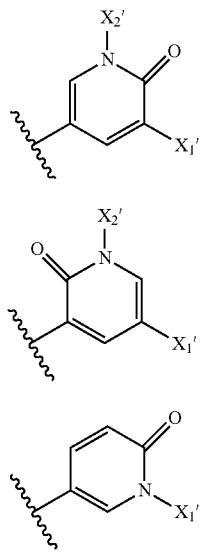

(ii)

(iii)

(v)

wherein
X$_1$' is one member selected from the following Group B; wherein Group B is selected from the group consisting of
-Cy,
—C(R$_{x1}$R$_{x2}$)-Cy,
—C(R$_{x1}$R$_{x2}$)—C(R$_{x3}$R$_{x4}$)-Cy,
—C(R$_{x1}$)═C(R$_{x2}$)-Cy,
—O-Cy,
—O—C(R$_{x1}$R$_{x2}$)-Cy,
—C(R$_{x1}$R$_{x2}$)—O-Cy,
—S(O)n-Cy,
—S(O)n-C(R$_{x1}$R$_{x2}$)-Cy,
—C(R$_{x1}$R$_{x2}$)—S(O)n-Cy,
—N(R$_{x5}$)-Cy,
—N(R$_{x5}$)—C(R$_{x1}$R$_{x2}$)-Cy,
—C(R$_{x1}$R$_{x2}$)—N(R$_{x5}$)-Cy,
—C(O)—N(R$_{x5}$)-Cy,
—N(R$_{x5}$)—C(O)-Cy,
—S(O)m-N(R$_{x5}$)-Cy,
—N(R$_{x5}$)—S(O)m-Cy, and
—O—S(O)m-Cy,
wherein n is an integer of 0 to 2; m is 1 or 2; Cy is a saturated or unsaturated cyclic group optionally having substituent(s), optionally containing heteroatom(s); R$_{x1}$, R$_{x2}$, R$_{x3}$, R$_{x4}$ and R$_{x5}$ are the same or different and each is a hydrogen, a C$_{1-6}$ alkyl group optionally having substituent(s) or a C$_{1-6}$ alkoxycarbonyl group optionally having substituent(s); and X$_2$' is an alkyl group optionally having substituent(s), wherein said substituents are optionally joined to form a ring.

8. The compound or salt according to claim 1, wherein Ar$_1$ is a C$_{6-10}$ aryl group having one or more substituents selected from the group consisting of a halogeno group, a halogenoC$_{1-6}$ alkyl group, a halogenoC$_{1-6}$ alkoxy group, and a C$_{1-6}$ alkyl group; or a C$_{1-9}$ heteroaryl group having one or more substituents selected from the group consisting of a halogeno group, a halogenoC$_{1-6}$ alkyl group, a halogenoC$_{1-6}$ alkoxy group and a C$_{1-6}$ alkyl group.

9. The compound or salt according to claim 7, wherein X$_1$' is -Cy, —O-Cy, —O—CH$_2$-Cy or —CH$_2$—CH$_2$-Cy.

10. The compound or salt according to claim 9, wherein Cy is benzene optionally having substituent(s), pyridine optionally having substituent(s), pyrimidine optionally having substituent(s), pyridazine optionally having substituent(s) or pyrazine optionally having substituent(s).

11. The compound or salt according to claim 9, wherein Cy is any of the groups shown below:

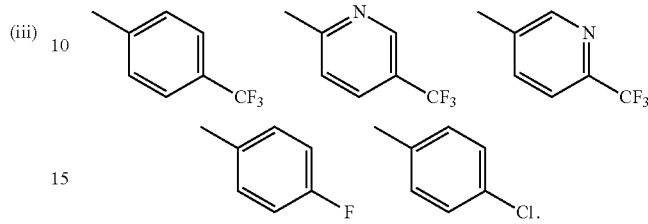

12. The compound or salt according to claim 1, wherein R$_4$ and R$_5$ are hydrogen;
the partial structure (b) containing ring A:

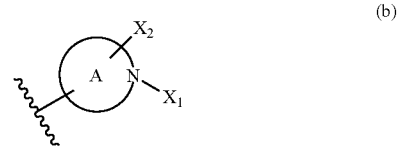

(b)

is a group represented by the following formula:

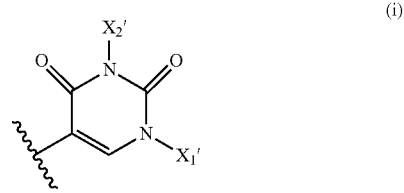

(i)

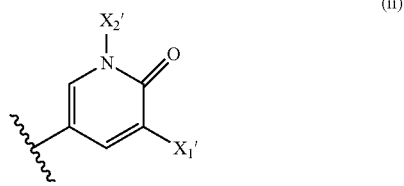

(ii)

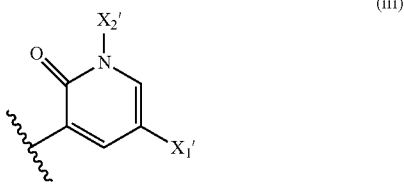

(iii)

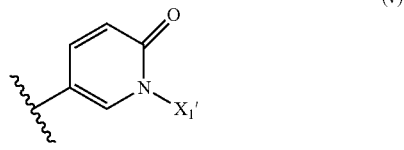

(v)

$X_1'$ is -Cy;

Cy is a group of any of the following formulas:

and $Ar_1$ is a group of any of the following formulas:

13. The compound or salt according to claim 1, wherein $R_4$ and $R_5$ are hydrogen;

the partial structure (b) containing ring A:

(b)

is a group represented by the following formula:

(i)

(ii)

(iii)

(v)

$X_1'$ is -Cy;

Cy is a group of any of the following formulas:

and $Ar_1$ is a group of any of the following formulas:

14. The compound or salr according to claim 1, wherein R$_4$ and R$_5$ are hydrogens;
the partial structure (b) containing ring A:

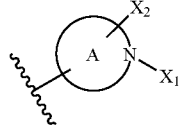
(b)

is a group represented by the following formula (i):

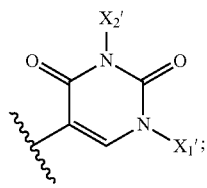
(i)

X$_1$' is -Cy;
Cy is a group of any of the following formulas:

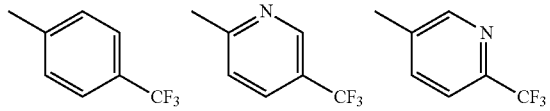

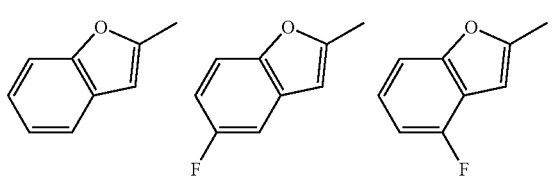

and
Ar$_1$ is a group of any of the following formulas:

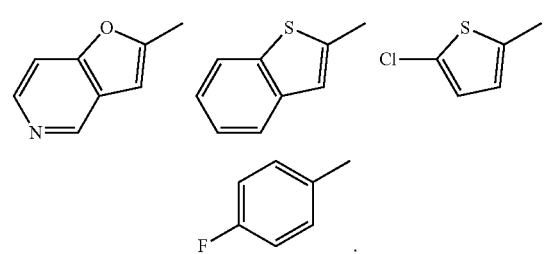

15. The compound or salt according to claim 1, wherein Ar$_1$ is a group of any of the following formulas:

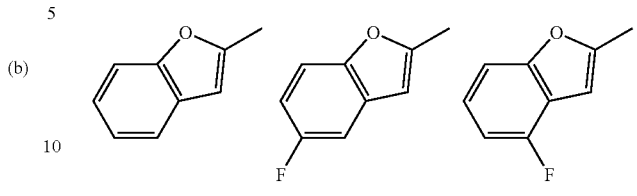

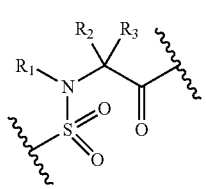
;

the partial structure (a):

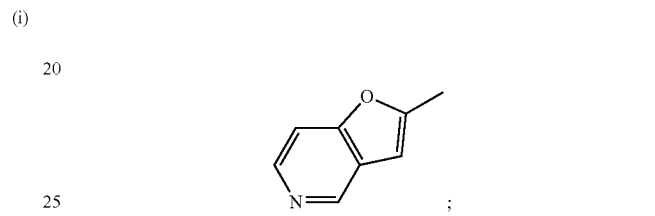
(a)

is a group of any of the following formulas:

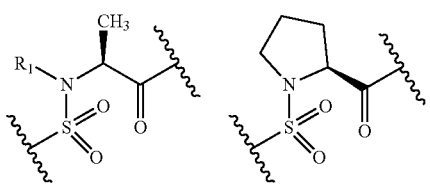

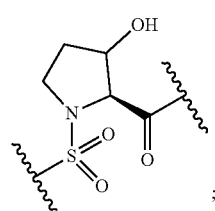
;

R₄ and R₅ are hydrogen;
the partial structure (b) containing ring A:
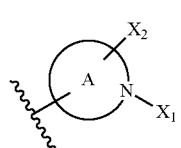
(b)
is a group represented by the following formula:
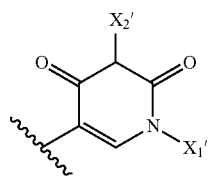
(i)
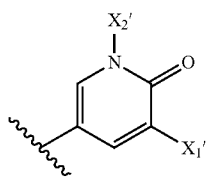
(ii)
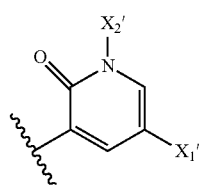
(iii)
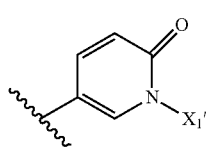
(v)
X₁' is -Cy; and
Cy is a group of any of the following formulas:
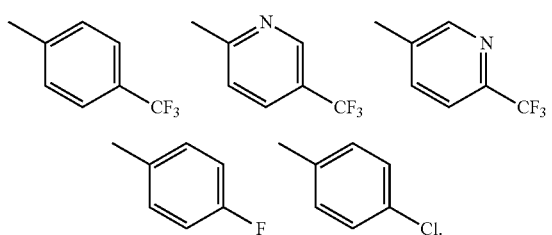
16. The compound or salt according to claim 1
Ar₁ is a group of any of the following formulas:
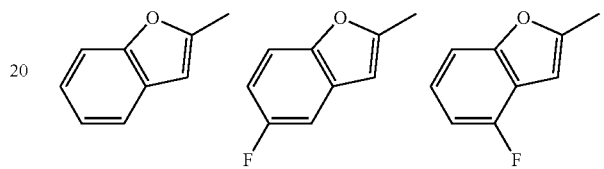
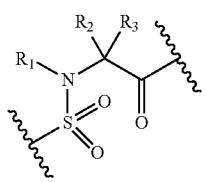
;
the partial structure (a):
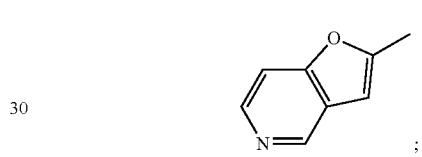
(a)
is a group of any of the following formulas:
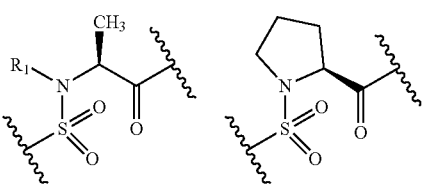
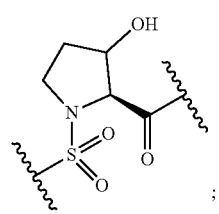
;

R$_4$ and R$_5$ are hydrogen;
the partial structure (b) containing ring A:
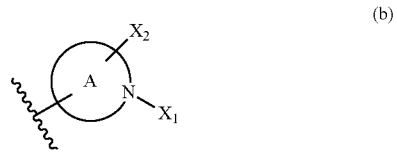
is a group represented by the following formula (i):
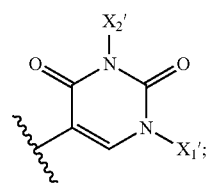
X$_1$' is -Cy; and
Cy is a group of any of the following formulas:
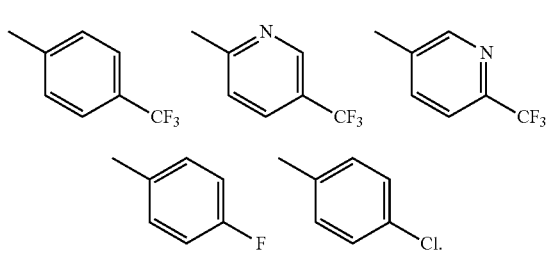
17. The compound or salt according to claim 1, which is represented by any of the following formulas:
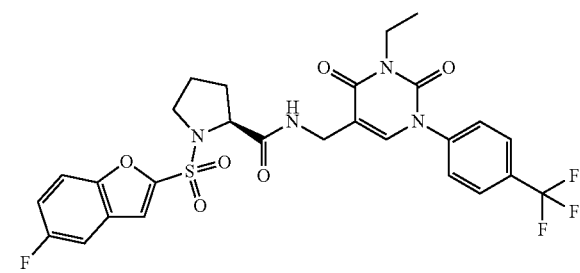
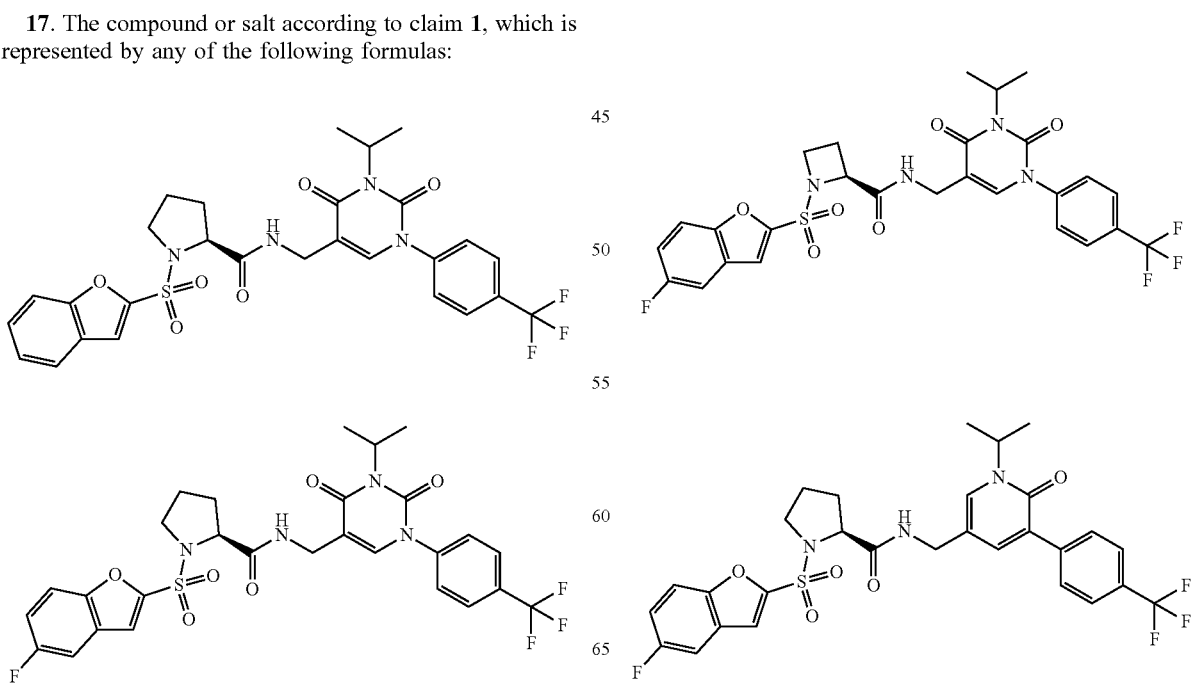

-continued

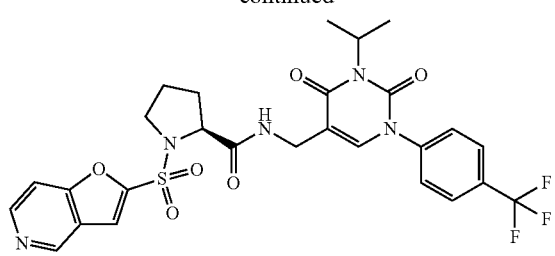

-continued

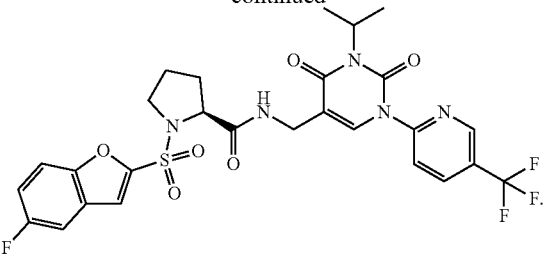

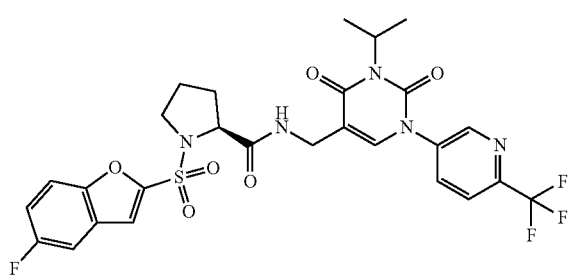

18. A method for the treatment of a disease involving TRPA1, comprising administering an effective amount of a compound or salt according to claim 1 to a subject in need thereof.

19. The method according to claim 18, wherein said disease involving TRPA1 is selected from the group consisting of chronic pain, acute pain, diabetic neuropathy, osteoarthritis, asthma, chronic cough, chronic obstructive pulmonary diseases, functional gastrointestinal disorder, erosive esophagitis, irritable bowel syndrome, inflammatory bowel disease, pancreatitis, anticancer agent-induced neuropathy, pruritus, and allergic dermatitis.

* * * * *

SEQUENCE LISTING

```
<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: synthetic primer 1

<400> SEQUENCE: 1
aactttagta agcttcgatc gccatgaag                                          29

<210> SEQ ID NO 2
<211> LENGTH: 34
<212> TYPE: DNA
<213> ORGANISM: Artificial Sequence
<220> FEATURE:
<223> OTHER INFORMATION: synthetic primer 2

<400> SEQUENCE: 2
gtaccgatct agaattcgtt tactaaggct caag                                    34
```